United States Patent
Matsumura

(10) Patent No.: US 11,331,390 B2
(45) Date of Patent: May 17, 2022

(54) OPHTHALMIC COMPOSITION

(71) Applicant: Rohto Pharmaceutical Co., Ltd., Osaka (JP)

(72) Inventor: Yasuko Matsumura, Osaka (JP)

(73) Assignee: ROHTO PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/094,919

(22) PCT Filed: Apr. 21, 2017

(86) PCT No.: PCT/JP2017/016017
§ 371 (c)(1),
(2) Date: Oct. 19, 2018

(87) PCT Pub. No.: WO2017/183714
PCT Pub. Date: Oct. 26, 2017

(65) Prior Publication Data
US 2019/0125877 A1    May 2, 2019

(30) Foreign Application Priority Data

| Apr. 22, 2016 | (JP) | ............................ JP2016-086451 |
| Apr. 22, 2016 | (JP) | ............................ JP2016-086456 |
| Apr. 13, 2017 | (JP) | ............................ JP2017-080069 |
| Apr. 13, 2017 | (JP) | ............................ JP2017-080072 |

(51) Int. Cl.

| A61K 47/26 | (2006.01) |
| A61K 9/00  | (2006.01) |
| A61K 31/045 | (2006.01) |
| A61K 31/14 | (2006.01) |
| A61K 31/355 | (2006.01) |
| A61K 47/44 | (2017.01) |
| A61K 47/10 | (2017.01) |
| C08J 5/00  | (2006.01) |
| A61K 47/18 | (2017.01) |
| A61K 47/12 | (2006.01) |
| A61K 47/02 | (2006.01) |
| A61K 47/22 | (2006.01) |

(52) U.S. Cl.
CPC ............ *A61K 47/26* (2013.01); *A61K 9/0048* (2013.01); *A61K 31/045* (2013.01); *A61K 31/14* (2013.01); *A61K 31/355* (2013.01); *A61K 47/02* (2013.01); *A61K 47/10* (2013.01); *A61K 47/12* (2013.01); *A61K 47/18* (2013.01); *A61K 47/44* (2013.01); *C08J 5/00* (2013.01); *A61K 47/186* (2013.01); *A61K 47/22* (2013.01); *C08J 2365/00* (2013.01)

(58) Field of Classification Search
CPC ............ C08J 5/00; C08J 2365/00; A61P 27/02
See application file for complete search history.

(56) References Cited

U.S. PATENT DOCUMENTS

| 5,077,033 | A | 12/1991 | Viegas et al. |
| 6,525,144 | B1 * | 2/2003 | Tanahashi ............. C08F 232/08 525/332.1 |
| 2002/0010193 | A1 * | 1/2002 | Doi ...................... A61K 9/0048 514/310 |
| 2003/0125498 | A1 * | 7/2003 | McCabe ................. A61L 27/18 528/25 |
| 2005/0247580 | A1 * | 11/2005 | Hamilton ............. B65D 75/326 206/5.1 |
| 2006/0063714 | A1 | 3/2006 | Jensen et al. |
| 2013/0331458 | A1 | 12/2013 | Miyano et al. |
| 2014/0308368 | A1 * | 10/2014 | Matsumura .............. A61K 9/08 424/642 |

FOREIGN PATENT DOCUMENTS

| EP | 2478906 A1 | 7/2012 |
| JP | 2003-306597 A | 10/2003 |
| JP | 2007-500244 A | 1/2007 |
| JP | 2009-196988 A | 9/2009 |
| JP | 2010-229159 A | 10/2010 |
| JP | 2010-274950 A | 12/2010 |
| JP | 2011-021002 A | 2/2011 |
| JP | 2012-006962 A | 1/2012 |

(Continued)

OTHER PUBLICATIONS

International Preliminary Report on Patentability and Written Opinion issued in corresponding International Patent Application No. PCT/JP2017/016017 dated Oct. 23, 2018.
International Search Report issued in corresponding International Patent Application No. PCT/JP2017/016017 dated May 30, 2017.
Extended European Search Report issued in corresponding European Patent Application No. 17786051.7 dated Dec. 17, 2019.

*Primary Examiner* — Savitha M Rao
*Assistant Examiner* — Andrew P Lee
(74) *Attorney, Agent, or Firm* — Morgan, Lewis & Bockius LLP

(57) ABSTRACT

The first aspect of the present invention relates to an ophthalmic composition comprising (A) one or more kinds selected from the group consisting of terpenoid, a tocopherol, and a benzyl ammonium compound and a salt thereof, wherein the ophthalmic composition is contained in a container in which a portion or the whole of a part coming into contact with the ophthalmic composition is formed from a resin containing a cyclic olefin.

The second aspect of the present invention relates to an ophthalmic composition comprising (A2) a surface active component and (B2) a buffer, wherein the ophthalmic composition is contained in a container in which a portion or the whole of a part coming into contact with the ophthalmic composition is formed from a resin containing a cyclic olefin.

10 Claims, No Drawings

(56) References Cited

FOREIGN PATENT DOCUMENTS

| | | |
|---|---|---|
| JP | 2012-086876 A | 5/2012 |
| JP | 2012-205821 A | 10/2012 |
| JP | 2014-214085 A | 11/2014 |
| TW | 201613602 A | 4/2016 |
| WO | 2004/112836 A1 | 12/2004 |
| WO | 2009/066511 A1 | 5/2009 |
| WO | 2010/079693 A1 | 7/2010 |
| WO | 2012/090985 A1 | 7/2012 |
| WO | 2013/065720 A1 | 5/2013 |
| WO | 2015/029924 A1 | 3/2015 |
| WO | 2015/156321 A1 | 10/2015 |
| WO | 2015/190483 A1 | 12/2015 |
| WO | 2016/047720 A1 | 3/2016 |

\* cited by examiner

OPHTHALMIC COMPOSITION

TECHNICAL FIELD

Hereinafter, the first aspect of the present invention and the second aspect of the present invention will be described in order.

The first aspect of the present invention relates to an ophthalmic composition.

BACKGROUND ART

Terpenoid, tocopherols and/or benzyl ammonium compounds such as benzalkonium may be blended into ophthalmic compositions (e.g., Patent Literatures 1 and 2).

Meanwhile, polypropylene, polyethylene, and polyethylene terephthalate containers and the like are widely used as containers that contain ophthalmic drug products (e.g., Patent Literature 3).

CITATION LIST

Patent Literature

Patent Literature 1: Japanese Unexamined Patent Publication No. 2011-21002
Patent Literature 2: Japanese Unexamined Patent Publication No. 2012-006962
Patent Literature 3: Japanese Unexamined Patent Publication No. 2009-196988

SUMMARY OF INVENTION

Technical Problem

The present inventor has found a new problem that when terpenoid, a tocopherol and/or a benzyl ammonium compound is contained in an ophthalmic composition, the dynamic contact angle to resins widely used is small, and wetting occurs easily. If wetting occurs easily to containers formed from these resins, liquid residues may be generated or liquid cutting may be deteriorated; thus there is a fear of inducing reduction in the quality and reduction in the use performance of the ophthalmic composition.

An object of the first aspect of the present invention is to provide an ophthalmic composition in which wetting to containers is suppressed while containing terpenoid, a tocopherol and/or a benzyl ammonium, compound.

Solution to Problem

The present inventor has found that in an ophthalmic composition containing (A) one or more kinds selected from the group consisting of terpenoid, a tocopherol, and a benzyl ammonium compound and a salt thereof, the dynamic contact angle is increased (i.e., wetting is suppressed) when a container formed from a resin containing a cyclic olefin is compared with containers formed from resins widely used.

Also, the present inventor has found a new problem that in the case where the ophthalmic composition containing the component (A) is contained in a container formed from a resin containing a cyclic olefin, aromaticity is reduced or odor is deteriorated during preservation, and found that in response to this, an ophthalmic composition further containing (B) a buffer, unexpectedly, suppresses change in smell, for example, by retaining the aromaticity or improving the odor.

The first aspect of the present invention is based on this finding and provides each of the following embodiments:

[1] An ophthalmic composition comprising
(A) one or more kinds selected from the group consisting of terpenoid, a tocopherol, and a benzyl ammonium compound and a salt thereof, wherein
the ophthalmic composition is contained in a container in which a portion or the whole of a part coming into contact with the ophthalmic composition is formed from a resin containing a cyclic olefin.
[2] The ophthalmic composition according to [1], wherein the resin forming the container further contains polyethylene.
[3] The ophthalmic composition according to [1] or [2], further comprising (B) a buffer.
[4] The ophthalmic composition according to any one of [1] to [3], wherein a total content of the component (A) is from 0.00001 to 1.0 w/v % based on the total amount of the ophthalmic composition.
[5] The ophthalmic composition according to any one of [1] to [4], wherein a total content of the component (B) is from 1 to 7000 parts by weight based on 1 part by weight of the total content of the component (A).
[6] The ophthalmic composition according to any one of [1] to [5], wherein pH of the ophthalmic composition is from 4.0 to 9.5.
[7] The ophthalmic composition according to any one of [1] to [6], wherein a content of water is 80 w/v % or more and less than 100 w/v % based on the total amount of the ophthalmic composition.
[8] The ophthalmic composition according to any one of [1] to [7], wherein a maximum value of light transmittance in a visible light region of wavelengths from 400 to 700 nm of the container formed from the resin containing a cyclic olefin is 50% or more.
[9] The ophthalmic composition according to any one of [1] to [8], wherein an amount of dropping per drop is from 1 to 99 μL.
[10] The ophthalmic composition according to any one of [1] to [9], wherein the number of uses is a small number or a single use.
[11] A method for imparting an effect of suppressing wetting to a resin containing a cyclic olefin to an ophthalmic composition, comprising
blending (A) one or more kinds selected from the group consisting of terpenoid, a tocopherol, and a benzyl ammonium compound and a salt thereof into the ophthalmic composition.
[12] A method for imparting an effect of suppressing change in smell to an ophthalmic composition, comprising blending (A) one or more kinds selected from the group consisting of terpenoid, a tocopherol, and a benzyl ammonium compound and a salt thereof, and (B) a buffer into the ophthalmic composition contained in a container formed from a resin containing a cyclic olefin.

Advantageous Effects of Invention

The ophthalmic composition of the first aspect of the present invention is contained in a container formed from a resin containing a cyclic olefin and therefore produces an effect of increasing the dynamic contact angle to the container (suppressing wetting) as compared with ophthalmic compositions contained in containers formed from resins widely used. This produces an effect of suppressing liquid residues of the ophthalmic composition and improving liquid cutting. Furthermore, this can suppress reduction in the quality and reduction in the use performance of the ophthalmic composition.

Moreover, the ophthalmic composition of the first aspect of the present invention, when further containing (B) a buffer, produces an effect of suppressing change in smell, for example, by retaining the aromaticity or improving the odor, even in the case where the ophthalmic composition containing the component (A) is contained in a container formed from a resin containing a cyclic olefin.

DESCRIPTION OF EMBODIMENTS

Hereinafter, embodiments for executing the first aspect of the present invention will be explained in detail. However, the first aspect of the present invention is not limited to the following embodiments.

Unless indicated otherwise herein, the unit "%" of content means "w/v %" and is synonymous with "g/100 mL". Unless indicated otherwise herein, the abbreviation "POE" means polyoxyethylene, and the abbreviation "POP" means polyoxypropylene.

[1. Ophthalmic Composition]

The ophthalmic composition according to the present embodiment contains (A) one or more kinds selected from the group consisting of terpenoid, a tocopherol, and a benzyl ammonium compound and a salt thereof (also simply referred to as "component (A)").

<Component (A)>

The terpenoid includes cyclic terpene and acyclic terpene and is not particularly limited as long as being a medically, pharmacologically (pharmaceutically) or physiologically acceptable one.

The cyclic terpene is terpenoid having at least one ring structure in the molecule. Examples of the cyclic terpene include menthol, carvone, anethole, eugenol, limonene, pinene, and their derivatives.

The acyclic terpene is terpenoid having no ring structure in the molecule. Examples of the acyclic terpene include geraniol, citronellol, linalool, linalyl acetate, and their derivatives.

In the first aspect of the present invention, essential oils containing the compounds described above may be used as the terpenoid. Examples of such essential oils include bergamot oil, peppermint oil, cool mint oil, spearmint oil, mentha oil, fennel oil, cinnamon oil, and rose oil.

The terpenoid may be any of a d form, an l form and a dl form, and examples include l-menthol, d-menthol, and dl-menthol.

However, there is a case where optical isomers are not present, depending on terpenoid, such as geraniol.

The terpenoid, preferably, does not contain camphor, borneol, menton, cineole or eucalyptus oil. As the terpenoid, menthol is preferred, and l-menthol is more preferred.

The terpenoid can also employ a commercially available one. The terpenoid may be used singly, or may be used in combination of two or more kinds thereof.

In the case of containing terpenoid as the component (A), it is preferred for the content of the terpenoid in the ophthalmic composition according to the present embodiment that the total content of the terpenoid should be, for example, from 0.00005 to 1 w/v % based on the total amount of the ophthalmic composition, it is more preferred to be from 0.0001 to 0.5 w/v %, it is still more preferred to be from 0.001 to 0.1 w/v %, it is yet still more preferred to be from 0.001 to 0.08 w/v %, it is particularly preferred to be from 0.002 to 0.07 w/v %, it is more particularly preferred to be from 0.002 to 0.06 w/v %, it is still more particularly preferred to be from 0.003 to 0.05 w/v %, and it is most preferred to be from 0.003 to 0.03 w/v %, in view of more significantly exerting the effect according to the first aspect of the present invention.

The tocopherol includes tocopherol and derivatives thereof. The tocopherol may be any of an α form, a β form, a γ form and a δ form and may be any of a d form, an l form and a dl form, and examples include d-α-tocopherol, dl-α-tocopherol, β-tocopherol, γ-tocopherol, and δ-tocopherol. Examples of the derivative of the tocopherol include tocopherol acetate, tocopherol nicotinate, and tocopherol succinate.

As the tocopherol, tocopherol acetate is preferred, and d-α-tocopherol acetate is more preferred.

The tocopherol can also employ a commercially available one. The tocopherol may be used singly, or may be used in combination of two or more kinds thereof.

In the case of containing a tocopherol as the component (A), it is preferred for the content of the tocopherol in the ophthalmic composition according to the present embodiment that the total content of the tocopherol should be, for example, from 0.00001 to 1.0 w/v % based on the total amount of the ophthalmic composition, it is more preferred to be from 0.0005 to 0.5 w/v %, it is still more preferred to be from 0.0005 to 0.1 w/v %, it is yet still more preferred to be from 0.0005 to 0.05 w/v %, it is particularly preferred to be from 0.001 to 0.04 w/v %, it is more particularly preferred to be from 0.003 to 0.03 w/v %, and it is still more particularly preferred to be from 0.006 to 0.03 w/v %, in view of more significantly exerting the effect according to the first aspect of the present invention.

The benzyl ammonium compound is a quaternary ammonium compound having a benzyl group. Examples of the benzyl ammonium compound include benzalkonium and benzethonium. Examples of the salt of the benzyl ammonium compound include benzalkonium chloride and benzethonium chloride.

As the benzyl ammonium compound or the salt thereof, benzalkonium or a salt thereof is preferred, and benzalkonium chloride is more preferred.

The benzyl ammonium compound or the salt thereof can also employ a commercially available one.

In the case of containing a benzyl ammonium compound or a salt thereof as the component (A), it is preferred for the content of the benzyl ammonium compound or the salt thereof in the ophthalmic composition according to the present embodiment that the total content of the benzyl ammonium compound or the salt thereof should be, for example, from 0.00001 to 0.5 w/v % based on the total amount of the ophthalmic composition, it is more preferred to be from 0.00005 to 0.1 w/v %, and it is still more preferred to be from 0.0001 to 0.02 w/v %, in view of more significantly exerting the effect according to the first aspect of the present invention.

The component (A) may be used singly, or may be used in combination of two or more kinds thereof.

The content of the component (A) in the ophthalmic composition according to the present embodiment is not particularly limited and is appropriately set depending on the kind of the component (A), the kind and content of an additional component to be blended, and the use and dosage form of the ophthalmic composition, etc. It is preferred for the content of the component (A) that the total content of the component (A) should be, for example, from 0.00001 to 1.0 w/v % based on the total amount of the ophthalmic composition, it is more preferred to be from 0.00005 to 0.8 w/v %, it is still more preferred to be from 0.0001 to 0.5 w/v %, it is yet still more preferred to be from 0.001 to 0.3 w/v %, it is particularly preferred to be from 0.001 to 0.25 w/v %, it is more particularly preferred to be from 0.001 to 0.20 w/v %, it is still more particularly preferred to be from 0.001 to 0.15 w/v %, it is yet still more particularly preferred to be from 0.001 to 0.12 w/v %, it is especially preferred to be from 0.001 to 0.08 w/v %, and it is most preferred to be from 0.001 to 0.06 w/v %, in view of more significantly exerting the effect according to the first aspect of the present invention.

<Component (B)>

It is preferred that the ophthalmic composition according to the present embodiment should further contain (B) a buffer (also simply referred to as "component (B)"). The ophthalmic composition further contains the component (B), whereby the effect according to the first aspect of the present invention is more significantly exerted. Furthermore, the ophthalmic composition further contains the component (B.) and thereby produces an effect of suppressing change in smell, for example, by retaining the aromaticity or improving the odor, even in the case where the ophthalmic composition containing the component (A) is contained in a container formed from a resin containing a cyclic olefin. The buffer includes inorganic buffers and organic buffers and is not particularly limited as long as being a medically, pharmacologically (pharmaceutically) or physiologically acceptable one.

The inorganic buffer is an inorganic acid-derived buffer. Examples of the inorganic buffer include boric acid buffers, phosphoric acid buffers, and carbonic acid buffers.

Examples of the boric acid buffer include boric acid and salts thereof (boric acid alkali metal salts, boric acid alkaline earth metal salts, etc.). Examples of the phosphoric acid buffer include phosphoric acid and salts thereof (phosphoric acid alkali metal salts, phosphoric acid alkaline earth metal salts, etc.). Examples of the carbonic acid buffer include carbonic acid and salts thereof (carbonic acid alkali metal salts, carbonic acid alkaline earth metal salts, etc.). As the boric acid buffer or the phosphoric acid buffer, a hydrate of borate salt or phosphoric salt may be used. More specific examples include, as the boric acid buffer, boric acid and salts thereof (sodium borate, potassium tetraborate, potassium metaborate, ammonium pentaborate, borax, etc.); as the phosphoric acid buffer, phosphoric acid and salts thereof (disodium hydrogenphosphate, sodium dihydrogen phosphate, potassium dihydrogen phosphate, trisodium monophosphate, tripotassium phosphate, calcium monohydrogen phosphate, monobasic calcium phosphate, etc.); and as the carbonic acid buffer, carbonic acid and salts thereof (sodium hydrogen carbonate, sodium carbonate, ammonium carbonate, potassium carbonate, calcium carbonate, potassium bicarbonate, magnesium carbonate, etc.).

The organic buffer is an organic acid- or organic base-derived buffer. Examples of the organic buffer include citric acid buffers, acetic acid buffers, Tris buffers, epsilon aminocaproic acid buffers, and AMPD buffers.

Examples of the citric acid buffer include citric acid and salts thereof (citric acid alkali metal salts, citric acid alkaline earth metal salts, etc.). Examples of the acetic acid buffer include acetic acid and salts thereof (acetic acid alkali metal salts, acetic acid alkaline earth metal salts, etc.). As the citric acid buffer or the acetic acid buffer, a hydrate of citrate salt or acetate salt may be used. More specific examples include: as the citric acid buffer, citric acid and salts thereof (sodium citrate, potassium citrate, calcium citrate, sodium dihydrogen citrate, disodium citrate, etc.); and as the acetic acid buffer, acetic acid and salts thereof (ammonium acetate, potassium acetate, calcium acetate, sodium acetate, etc.). Examples of the Tris buffer include trometamol and salts thereof (trometamol hydrochloride, etc.). Examples of the epsilon aminocaproic acid buffer include epsilon aminocaproic acid and salts thereof. Examples of the AMPD buffer include 2-amino-2-methyl-1,3-propanediol and salts thereof.

Among these buffers, boric acid buffers (e.g., a combination of boric acid and borax), phosphoric acid buffers (e.g., a combination of disodium hydrogenphosphate and sodium dihydrogen phosphate), and epsilon aminocaproic acid buffers (e.g., epsilon aminocaproic acid) are preferred.

The buffer can also employ a commercially available one. The buffer may be used singly, or may be used in combination of two or more kinds thereof.

The content of the component (B) in the ophthalmic composition according to the present embodiment is not particularly limited and is appropriately set depending on the kind of the component (B), the kind and content of an additional component to be blended, and the use and dosage form of the ophthalmic composition, etc. It is preferred for the content of the component (B) that the total content of the component (B) should be, for example, from 0.0001 to 9 w/v % based on the total amount of the ophthalmic composition, it is more preferred to be from 0.001 to 9 w/v %, it is still more preferred to be from 0.005 to 8 w/v %, it is yet still more preferred to be from 0.01 to 8 w/v %, and it is particularly preferred to be from 0.01 to 6 w/v %, in view of more significantly exerting the effect according to the first aspect of the present invention.

The content ratio of the component (B) to the component (A) in the ophthalmic composition according to the present embodiment is not particularly limited and is appropriately set depending on the kinds of the component (A) and the component (B), the kind and content of an additional component to be blended, and the use and dosage form of the ophthalmic composition, etc. It is preferred for the content ratio of the component (B) to the component (A) that the total content of the component (B) should be, for example, from 1 to 7000 parts by weight based on 1 part by weight of the total content of the component (A) contained in the ophthalmic composition according to the present embodiment, it is more preferred to be from 5 to 4000 parts by weight, it is still more preferred to be from 10 to 2000 parts by weight, it is yet still more preferred to be from 10 to 1000 parts by weight, it is particularly preferred to be from 10 to 600 parts by weight, it is more particularly preferred to be from 10 to 400 parts by weight, it is still more particularly preferred to be from 20 to 300 parts by weight, it is yet still more particularly preferred to be from 20 to 200 parts by weight, it is especially preferred to be from 20 to 180 parts by weight, and it is most preferred to be from 20 to 150 parts by weight, in view of more significantly exerting the effect according to the first aspect of the present invention.

The ophthalmic composition according to the present embodiment may further contain a nonionic surfactant. The ophthalmic composition further contains the nonionic surfactant, whereby the effect according to the first aspect of the present invention is more significantly exerted.

Specific examples of the nonionic surfactant include: POE sorbitan fatty acid esters such as monolaurate POE (20) sorbitan (polysorbate 20), monopalmitate POE (20) sorbitan (polysorbate 40), monostearate acid POE (20) sorbitan (polysorbate 60), tristearate POE (20) sorbitan (polysorbate 65), and monooleate POE (20) sorbitan (polysorbate 80); POE hydrogenated castor oils such as POE (5) hydrogenated castor oil (polyoxyethylene hydrogenated castor oil 5), POE

(10) hydrogenated castor oil (polyoxyethylene hydrogenated castor oil 10), POE (20) hydrogenated castor oil (polyoxyethylene hydrogenated castor oil 20), POE (30) hydrogenated castor oil (polyoxyethylene hydrogenated castor oil 30), POE (40) hydrogenated castor oil (polyoxyethylene hydrogenated castor oil 40), POE (60) hydrogenated castor oil (polyoxyethylene hydrogenated castor oil 60), POE (80) hydrogenated castor oil (polyoxyethylene hydrogenated castor oil 80), and POE (100) hydrogenated castor oil (polyoxyethylene hydrogenated castor oil 100); POE castor oils such as POE (3) castor oil (polyoxyethylene castor oil 3), POE (10) castor oil (polyoxyethylene castor oil 10), POE (35) castor oil (polyoxyethylene castor oil 35), and POE (70) castor oil (polyoxyethylene castor oil 70); POE alkyl ethers such as POE (9) lauryl ether; POE-POP alkyl ethers such as POE (20) POP (4) cetyl ether; POE-POP glycols such as POE (20) POP (20) glycol (Pluronic L44), POE (42) POP (67) glycol (Poloxamer 403, Pluronic P123), POE (54) POP (39) glycol (Poloxamer 235, Pluronic P85), POE (120) POP (40) glycol (Pluronic F87), POE (160) POP (30) glycol (Poloxamer 188, Pluronic F68), POE (196) POP (67) glycol (Poloxamer 407, Pluronic F127), and POE (200) POP (70) glycol; and polyethylene glycol monostearates such as polyoxyl 10 stearate and polyoxyl 40 stearate. Note that the numbers in brackets for the compounds listed above represent addition mol numbers.

As the nonionic surfactant, POE sorbitan fatty acid esters, polyoxyethylene hydrogenated castor oils, polyoxyethylene castor oils, POE-POP glycols and polyethylene glycol monostearates are preferred, and polysorbate 80 and polyoxyethylene hydrogenated castor oil 60 are more preferred.

The nonionic surfactant can also employ a commercially available one. The nonionic surfactant may be used singly, or may be used in combination of two or more kinds thereof.

The content of the nonionic surfactant in the ophthalmic composition according to the present embodiment is not particularly limited and is appropriately set depending on the kind of the nonionic surfactant, the kind and content of an additional component to be blended, and the use and dosage form of the ophthalmic composition, etc. It is preferred for the content of the nonionic surfactant that the total content of the nonionic surfactant should be, for example, from 0.00001 to 10 w/v % based on the total amount of the ophthalmic composition, it is more preferred to be from 0.0001 to 8 w/v %, it is still more preferred to be from 0.001 to 5 w/v %, it is yet still more preferred to be from 0.01 to 4 w/v %, it is particularly preferred to be from 0.01 to 3 w/v %, it is more particularly preferred to be from 0.01 to 2 w/v %, it is still more particularly preferred to be from 0.01 to 1.5 w/v %, it is yet still more particularly preferred to be from 0.01 to 0.8 w/v %, it is especially preferred to be from 0.01 to 0.6 w/v %, and it is most preferred to be from 0.01 to 0.5 w/v %, in view of more significantly exerting the effect according to the first aspect of the present invention.

The ophthalmic composition according to the present embodiment may further contain one or more kinds of components selected from the group consisting of a vitamin (except for tocopherols), an antioxidant, an oil, a preservative (except for benzyl ammonium compounds or salts thereof), a polysaccharide, a vinyl compound, an amino acid, and a polyalcohol. These components are not particularly limited as long as being medically, pharmacologically (pharmaceutically) or physiologically acceptable ones.

The vitamin can be appropriately selected from known vitamins and used. Specific examples of the vitamin include: lipid soluble vitamins such as vitamin A (retinal, retinol, retinoic acid, carotene, dehydroretinal, lycopene, etc.), and their derivatives, and their salts; and water soluble vitamins such as vitamin B 1, vitamin B2 (flavin adenine dinucleotide), niacin (nicotinic acid and nicotinamide), pantothenic acid, panthenol, vitamin B6 (pyridoxine, pyridoxalisol, and pyridoxamine), biotin, folic acid, and vitamin B12 (cyanocobalamin, hydroxocobalamin, methylcobalamin, and adenosylcobalamin), and their salts. Specific examples of the salt of the vitamin include flavin adenine dinucleotide sodium, pyridoxine hydrochloride, calcium pantothenate, and sodium pantothenate. Specific examples of the derivative of the vitamin include retinol acetate and retinol palmitate.

As the vitamin, cyanocobalamin, flavin adenine dinucleotide, panthenol, pyridoxine, retinol and their derivatives, and their salts are preferred, and cyanocobalamin, flavin adenine dinucleotide sodium, panthenol, pyridoxine hydrochloride, and retinol palmitate are more preferred.

The vitamin can also employ a commercially available one. The vitamin may be used singly, or may be used in combination of two or more kinds thereof.

The antioxidant is a compound that suppresses harmful reaction in which oxygen is involved, and a salt thereof. The antioxidant can be appropriately selected from known antioxidants and used.

Specific examples of the antioxidant include butylhydroxyanisole, dibutylhydroxytoluene, ascorbic acid and their salts.

As the antioxidant, butylhydroxyanisole, dibutylhydroxytoluene, and their salts are preferred, and butylhydroxyanisole and dibutylhydroxytoluene are more preferred.

The antioxidant can also employ a commercially available one. The antioxidant may be used singly, or may be used in combination of two or more kinds thereof.

The oil includes vegetable-derived vegetable oils, animal-derived animal oils, and natural or synthetic mineral oils. The oil can be appropriately selected from known oils and used.

Specific examples of the oil include: vegetable oils such as soybean oil, rice oil, rapeseed oil, cottonseed oil, sesame oil, safflower oil, almond oil, castor oil, olive oil, cacao oil, camellia oil, sunflower oil, palm oil, flax oil, perilla oil, shea oil, coconut oil, jojoba oil, grapeseed oil, and avocado oil; animal oils such as beeswax, lanoline (purified lanoline, etc.), orange roughy oil, squalane and horse oil; and mineral oils such as Vaseline (white Vaseline and yellow Vaseline, etc.) and liquid paraffine.

As the oil, sesame oil, castor oil, beeswax, lanoline, Vaseline and liquid paraffine are preferred.

The oil can also employ a commercially available one. The oil may be used singly, or may be used in combination of two or more kinds thereof.

The preservative is a compound having bactericidal activity or bacteriostatic activity, and a salt thereof. The preservative can be appropriately selected from known preservatives or antibacterial agents and used.

Specific examples of the preservative include quaternary ammonium compounds (chlorhexidine, alexidine, polyhexanide), alkylpolyaminoethylglycine, benzoic acid, chlorobutanol, sorbic acid, dehydroacetic acid, paraben (e.g., parahydroxybenzoic acid esters such as methyl parahydroxybenzoate, ethyl parahydroxybenzoate, propyl parahydroxybenzoate, and butyl parahydroxybenzoate), oxyquinoline, phenylethyl alcohol, benzyl alcohol, polyquaterniums, Glokill (manufactured by Rhodia, product name), zinc, sulfisoxazole, sulfadimidine and sulfamethoxazole, and their salts.

Specific examples of the salt of the preservative include hydrochloric-acid alkyldiaminoethylglycine, sodium benzoate, chlorhexidine gluconate, potassium sorbate, sodium dehydroacetate, oxyquinoline sulfate, polyhexanide hydrochloride, polidronium chloride, zinc chloride, sulfisomidine sodium and sulfamethoxazole sodium.

As the preservative, quaternary ammonium compounds, alkylpolyaminoethylglycine, chlorobutanol, sorbic acid, paraben, phenylethyl alcohol and zinc are preferred, and polyhexamethylene biguanide, chlorhexidine gluconate, potassium sorbate, alexidine, polyhexanide hydrochloride, chlorobutanol, potassium sorbate, paraben, phenylethyl alcohol and zinc chloride are more preferred.

The preservative can also employ a commercially available one. The preservative may be used singly, or may be used in combination of two or more kinds thereof.

The polysaccharide includes dextran, acidic polysaccharides, cellulose-based polymer compounds and their salts. The polysaccharide can be appropriately selected from known polysaccharides and used.

Specific examples of the dextran include dextran 40 and dextran 70.

The acidic polysaccharide is a polysaccharide having an acidic group. Specific examples of the acidic polysaccharide include: acidic mucopolysaccharides such as hyaluronic acid, chondroitin sulfate, chitosan, heparin, heparan, alginic acid, and their derivatives (e.g., acetylated forms); and xanthan gum and gellan gum.

As the cellulose-based polymer compound, cellulose, and polymer compounds in which a hydroxyl group of cellulose is replaced with other functional groups can be used. Examples of the functional group that replaces the hydroxyl group of cellulose include a methoxy group, an ethoxy group, a hydroxymethoxy group, a hydroxyethoxy group, a hydroxypropoxy group, a carboxymethoxy group and a carboxyethoxy group. Specific examples of the cellulose-based polymer compound include methylcellulose, ethylcellulose, hydroxyethylcellulose, hydroxymethylcellulose, hydroxypropylcellulose, hydroxypropylmethylcellulose (hypromellose), carboxymethylcellulose, and carboxyethylcellulose.

As the polysaccharide, dextran, acidic polysaccharides, cellulose-based polymer compounds and their salts are preferred, dextran, acidic polysaccharides, hydroxyethylcellulose, hydroxypropylmethylcellulose, carboxymethylcellulose and their salts are more preferred, dextran, acidic mucopolysaccharides, xanthan gum, gellan gum, hydroxyethylcellulose, hydroxypropylmethylcellulose, carboxymethylcellulose and their salts are still more preferred, and dextran, chondroitin sulfate, hyaluronic acid, xanthan gum, gellan gum, hydroxyethylcellulose, hydroxypropylmethylcellulose, carboxymethylcellulose and their salts are particularly preferred.

The polysaccharide can also employ a commercially available one. The polysaccharide may be used singly, or may be used in combination of two or more kinds thereof.

The vinyl compound includes vinyl-based polymer compounds and their salts. The vinyl compound can be appropriately selected from known vinyl compounds and used.

Specific examples of the vinyl compound include vinyl alcohol-based polymers such as polyvinyl alcohol (completely or partially saponification products), vinylpyrrolidone-based polymers such as polyvinylpyrrolidone and carboxyvinyl polymers, and their salts.

As the vinyl compound, polyvinyl alcohol, polyvinylpyrrolidone, carboxyvinyl polymers and their salts are preferred, polyvinyl alcohol, polyvinylpyrrolidone, carboxyvinyl polymers and salts thereof are more preferred, polyvinyl alcohol, polyvinylpyrrolidone K17, polyvinylpyrrolidone K25, polyvinylpyrrolidone K30, polyvinylpyrrolidone K90, carboxyvinyl polymers and their salts are still more preferred, and polyvinyl alcohol, polyvinylpyrrolidone K30, polyvinylpyrrolidone K90, carboxyvinyl polymers and salts thereof are particularly preferred.

The vinyl compound can also employ a commercially available one. The vinyl compound may be used singly, or may be used in combination of two or more kinds thereof.

The amino acid is a compound having an amino group and a carboxyl group in the molecule, and a derivative thereof, and their salts. The amino acid can be appropriately selected from known amino acids and used.

Examples of the amino acid include amino acids and salts thereof, and amino acid derivatives and salts thereof. Specific examples of the amino acid and the salt thereof include: monoamino monocarboxylic acids such as glycine, alanine, aminobutyric acid, and aminovaleric acid; monoamino dicarboxylic acids such as aspartic acid and glutamic acid; diamino monocarboxylic acids such as arginine and lysine; and their salts. Specific examples of the amino acid derivative and the salt thereof include amino acid derivatives such as aminoethylsulfonic acid (taurine), and salts thereof. The amino acid may be any of a D form, an L form, and a DL form.

As the amino acid, monoamino dicarboxylic acids, amino acid derivatives, and their salts are preferred, glycine, aspartic acid, glutamic acid, arginine, taurine and their salts are more preferred, and glycine, potassium aspartate, magnesium aspartate, sodium glutamate, arginine and taurine are still more preferred.

The amino acid can also employ a commercially available one. The amino acid may be used singly, or may be used in combination of two or more kinds thereof.

The polyalcohol is an alcohol having two or more hydroxy groups in the molecule, and a salt thereof. The polyalcohol can be appropriately selected from known polyalcohols and used.

Examples of the polyalcohol include: aliphatic polyalcohols (aliphatic alcohols having two or more hydroxy groups in the molecule) such as glycerin, propylene glycol, ethylene glycol, diethylene glycol, and polyethylene glycol (300, 400, 4000, 6000); sugar alcohols such as glucose, lactose, maltose, fructose, sorbitol, maltitol, mannitol, xylitol, and trehalose; and their salts.

As the polyalcohol, aliphatic polyalcohols and sugar alcohols are preferred, and glycerin, propylene glycol, polyethylene glycol, sorbitol and mannitol are more preferred.

The polyalcohol can also employ a commercially available one. The polyalcohol may be used singly, or may be used in combination of two or more kinds thereof.

The pH of the ophthalmic composition according to the present embodiment is not particularly limited as long as being within the range that is medically, pharmacologically (pharmaceutically) or physiologically acceptable. The pH of the ophthalmic composition according to the present embodiment can be, for example, from 4.0 to 9.5, and it is preferred to be from 4.0 to 9.0, it is more preferred to be from 4.5 to 9.0, it is still more preferred to be from 4.5 to 8.5, and it is yet still more preferred to be from 5.0 to 8.5.

If necessary, the ophthalmic composition according to the present embodiment can be adjusted to an osmotic pressure ratio within the range that is acceptable to biological bodies. The appropriate osmotic pressure ratio may be appropriately set depending on the use, dosage form, use method, etc. of the ophthalmic composition, but can be, for example, from 0.4 to 5.0, and it is preferred to be from 0.6 to 3.0, it is more preferred to be from 0.8 to 2.2, and it is still more preferred to be from 0.8 to 2.0. The osmotic pressure ratio is a ratio of an osmotic pressure of a sample to 286 mOsm (osmotic pressure of a 0.9 w/v % sodium chloride aqueous solution) based on the Japanese Pharmacopoeia, 16th version, and the osmotic pressure is measured with reference to the osmometry deteituination described in the Japanese Pharmacopoeia (cryoscopic method). Note that the standard solution for osmotic pressure ratio measurement (0.9 w/v % sodium chloride aqueous solution) is prepared by drying sodium chloride (The Japanese Pharmacopoeia standard reagent) at 500 to 650° C. for 40 to 50 minutes, thereafter allowing it to cool in a desiccator (silica gel), accurately weighing 0.900 g thereof, and dissolving it in purified water to accurately make up a volume of 100 mL, or alternatively, a commercially available standard solution for osmotic pressure ratio measurement (0.9 w/v % sodium chloride aqueous solution) can be used.

The viscosity of the ophthalmic composition according to the present embodiment is not particularly limited as long as being within the range that is medically, pharmacologically (pharmaceutically) or physiologically acceptable. It is preferred for the viscosity of the ophthalmic composition according to the present embodiment that the viscosity at 20° C. measured with, for example, a rotational viscometer (RE550 viscometer, manufactured by Azuma Industry Co., Ltd., rotor; 1° 34' x R24) should be from 0.01 to 10000 mPa·s, it is more preferred to be from 0.05 to 8000 mPa·s, and it is still more preferred to be from 0.1 to 1000 mPa·s.

The ophthalmic composition according to the present embodiment may contain an appropriate amount of a combination of components selected from various pharmacologically active components and physiologically active components, in addition to the components described above, without impairing the effect of the first aspect of the present invention. The components are not particularly limited, and examples include active components in ophthalmic drugs described in Standards of Production and Sale of OTC Drugs 2012 (supervised by SOCIETY FOR REGULATORY SCIENCE OF MEDICAL PRODUCTS). Specific examples of the components used for ophthalmic drugs include components as follows:

antihistamine drugs: e.g., iproheptine, diphenhydramine hydrochloride, chlorpheniramine maleate, ketotifen fumarate, olopatadine hydrochloride, and levocabastine hydrochloride;

antiallergic drugs: e.g., disodium cromoglycate, tranilast, pemirolast potassium, and acitazanolast;

steroid drugs: e.g., fluticasone propionate, fluticasone furoate, mometasone furoate, beclometasone dipropionate, and flunisolide;

anti-inflammatory drugs: e.g., glycyrrhetinic acid, dipotassium glycyrrhizate, pranoprofen, methyl salicylate, glycol salicylate, allantoin, tranexamic acid, berberine, azulene sodium sulfonate, lysozyme chloride, zinc sulfate, zinc lactate, and licorice;

decongestants: tetrahydrozoline hydrochloride, tetrahydrozoline nitrate, naphazoline hydrochloride, naphazoline nitrate, epinephrine, epinephrine hydrochloride, ephedrine hydrochloride, phenylephrine hydrochloride, methylephedrine dl-hydrochloride, etc.;

ocular muscle regulating drugs: e.g., cholinesterase inhibitors having an active center similar to that of acetylcholine, specifically, neostigmine methylsulfate, tropicamide, helenien, atropine sulfate, etc.;

astringent drugs: e.g., hydrozincite, zinc lactate, and zinc sulfate;

local anesthetics: e.g., lidocaine and procaine; and others: rebamipide, etc.

In the ophthalmic composition according to the present embodiment, one or more kinds appropriately selected from various additives may be concomitantly used and contained in an appropriate amount in accordance with a conventional method depending on the use and dosage form thereof, without impairing the effect of the first aspect of the present invention. Examples of such additives include various additives described in Iyakuhin Tenkabutu Jiten 2007 (Encyclopedia of Pharmaceutical Excipients in English) (edited by Japan Pharmaceutical Excipients Council Japan). Examples of typical components include the following additives:

carriers: e.g., aqueous solvents such as water and hydrous ethanol;

chelating drugs: e.g., ethylenediamine diacetate (EDDA), ethylenediamine triacetic acid, ethylenediaminetetraacetate (EDTA), N-(2-hydroxyethyl)ethylenediamine-triacetic acid (HEDTA), and diethylenetriaminepentaacetic acid (DTPA);

bases: e.g., octyl dodecanol, titanium oxide, potassium bromide, and Plastibase;

pH adjusters: hydrochloric acid, acetic acid, sodium hydroxide, potassium hydroxide, calcium hydroxide, magnesium hydroxide, triethanolamine, diisopropanolamine, etc.;

stabilizers: sodium formaldehyde sulfoxylate (Rongalite), sodium bisulfite, sodium pyrosulfite, aluminum monostearate, glycerin monostearate, cyclodextrin, monoethanolamine, etc.;

anionic surfactants: polyoxyethylene alkyl ether phosphates, polyoxyethylene alkyl ether sulfates, alkylbenzenesulfonates, alkylsulfates, N-acyltaurine salts, etc.; and amphoteric surfactants: lauryl dimethylaminoacetic acid betaine, etc.

In the case where the ophthalmic composition according to the present embodiment contains water, it is preferred for the content of the water that the content of the water should be, for example, 80 w/v % or more and less than 100 w/v % based on the total amount of the ophthalmic composition, it is more preferred to be 85 w/v % or more and 99.5 w/v % or less, and it is still more preferred to be 90 w/v % or more and 99.2 w/v % or less, in view of more significantly exerting the effect according to the first aspect of the present invention.

The water used in the ophthalmic composition according to the present embodiment can be a medically, pharmacologically (pharmaceutically) or physiologically acceptable one. Examples of such water include distilled water, water, purified water, sterile purified water, water for injection, and distilled water for injection. These definitions are based on the Japanese Pharmacopoeia, 16th version.

The ophthalmic composition according to the present embodiment can be prepared by adding and mixing the desired amount of the component (A), and other components, if necessary, so as to have the desired concentration. For example, it can be prepared by dissolving or dispersing these components in purified water to be adjusted to a predetermined pH and osmotic pressure, and sterilizing the resultant by filter sterilization or the like.

The ophthalmic composition according to the present embodiment can take various dosage forms depending on the intended use. Examples of the dosage form include liquid drugs, gel drugs, and semi solid drugs (ointments, etc.).

The ophthalmic composition according to the present embodiment can be used as, for example, eye drops (also referred to as ophthalmic solutions or ophthalmic drugs, and further, the eye drops include eye drops that can be instilled into eyes during use of contact lenses), artificial tears, eye washes (also referred to as collyriums or eye lotions, and further, the eye washes include eye washes that can wash eyes during use of contact lenses), and compositions for contact lenses [solutions for wearing a contact lens, compositions for contact lens care (contact lens disinfecting solutions, contact lens storage solutions, contact lens cleaning solutions, contact lens cleaning and storage solutions), etc.]. Note that the "contact lens" includes hard contact lenses and soft contact lenses (ionic and non-ionic lenses are both included and silicone hydro gel contact lenses and non-silicone hydro-gel contact lenses are both included).

In the case where the ophthalmic composition according to the present embodiment is eye drops, the dosage and administration thereof are not particularly limited as long as exerting effects and being a dosage and administration with less adverse reactions, and examples include a method of using by applying eye drop four times a day at 1 to 2 drops per dose, and a method of using by applying eye drop five to six times a day at 2 to 3 drops per dose, in the case of adults (15 years old or over) and children at age 7 or over.

<Container>

The ophthalmic composition according to the present embodiment is provided after being contained in a container in which a portion or the whole of a part coming into contact with the ophthalmic composition is formed from a resin containing a cyclic olefin (also simply referred to as "cyclic olefin-containing resin").

Examples of the cyclic olefin-containing resin include resins containing a cyclic olefin polymer (also simply referred to as "COP-containing resins"), and resins containing a cyclic olefin copolymer (also simply referred to as "COC-containing resins"). The cyclic olefin-containing resin is preferably a COC-containing resin in view of more significantly exerting the effect according to the first aspect of the present invention.

The COP-containing resin is not particularly limited as long as containing a polymer of one kind of cyclic olefin homopolymerized or a polymer of two or more kinds of cyclic olefins copolymerized, or a hydrogenation product thereof. The COP-containing resin preferably contains a ring-opened polymer of the cyclic olefin or a hydrogenation product thereof Also, the COP-containing resin preferably contains a non-crystalline polymer.

The COC-containing resin is not particularly limited as long as containing a polymer of a cyclic olefin and an acyclic olefin copolymerized, or a hydrogenation product thereof.

Examples of the cyclic olefin include monocyclic or polycyclic cycloalkanes having a vinyl group, monocyclic or polycyclic cycloalkenes, and their derivatives. The cyclic olefin is preferably norbornene, tetracyclododecene, and their derivatives. Examples of the acyclic olefin include a-olefins such as ethylene, propylene, 1-butene, 1-pentene, and 1-hexene.

As the COP-containing resin, a resin containing a polymer of a cyclic olefin having a norbornene skeleton, or a hydrogenation product thereof is preferred in view of more significantly exerting the effect according to the first aspect of the present invention. As the COC-containing resin, a resin containing a polymer of norbornene and ethylene copolymerized is preferred in view of more significantly exerting the effect according to the first aspect of the present invention. Note that an additional monomer may be contained, in the polymer of a cyclic olefin and an acyclic olefin copolymerized, as a constituent of this polymer.

In the cyclic olefin-containing resin, for example, an additional polymer such as polyethylene (PE; high-density polyethylene (HDPE), low-density polyethylene (LDPE), linear low-density polyethylene (LLDPE)), polypropylene (PP), polycarbonate, a (meth)acrylic acid-based polymer, polystyrene (PS), polyethylene naphthalate (PEN), polyethylene terephthalate (PET), and polyarylate may be contained. It is preferred that the cyclic olefin-containing resin should further contain polyethylene (PE) and/or polypropylene (PP), in view of more significantly exerting the effect according to the first aspect of the present invention. In the case where the cyclic olefin-containing resin contains polyethylene (PE) and/or polypropylene (PP), it is preferred that the content of the polyethylene (PE) and/or the polypropylene (PP) should be from 0.001 to 50% by weight based on the total amount of the cyclic olefin-containing resin, it is more preferred to be from 0.01 to 45% by weight, it is still more preferred to be from 0.05 to 40% by weight, it is yet still more preferred to be from 0.1 to 35% by weight, it is particularly preferred to be from 0.5 to 30% by weight, it is more particularly preferred to be from 1 to 25% by weight, it is still more particularly preferred to be from 2 to 20% by weight, and it is most preferred to be from 5 to 15% by weight. In the case where the cyclic olefin-containing resin contains polyethylene (PE) and/or polypropylene (PP), it is preferred that the content of the polyethylene (PE) and/or the polypropylene (PP) should be 10% by weight or more based on the weight of the whole container, it is more preferred to be 15% by weight or more, it is still more preferred to be 20% by weight or more, it is yet still more preferred to be 25% by weight or more, it is particularly preferred to be 30% by weight or more, it is more particularly preferred to be 35% by weight or more, it is still more particularly preferred to be 38% by weight or more, and it is most preferred to be 40% by weight or more. In the case where the cyclic olefin-containing resin contains polyethylene (PE) and/or polypropylene (PP), it is preferred that the content of the polyethylene (PE) and/or the polypropylene (PP) should be 95% by weight or less based on the weight of the whole container, it is more preferred to be 90% by weight or less, it is still more preferred to be 85% by weight or less, it is yet still more preferred to be 80% by weight or less, it is particularly preferred to be 75% by weight or less, it is more particularly preferred to be 70% by weight or less, it is still more particularly preferred to be 65% by weight or less, and it is most preferred to be 60% by weight or less.

It is preferred for the cyclic olefin-containing resin according to the present embodiment that the content of the polymer of a cyclic olefin and an acyclic olefin copolymerized should be from 55 to 98% by weight based on the total amount of the cyclic olefin-containing resin, it is more preferred to be from 60 to 98% by weight, it is still more preferred to be from 65 to 98% by weight, it is yet still more preferred to be from 70 to 98% by weight, it is particularly preferred to be from 75 to 98% by weight, it is more particularly preferred to be from 80 to 98% by weight, it is still more particularly preferred to be from 85 to 98% by weight, and it is most preferred to be from 90 to 95% by weight. It is preferred for the cyclic olefin-containing resin according to the present embodiment that the content of the polymer of a cyclic olefin and an acyclic olefin copolymerized should be 10% by weight or more based on the weight of the whole container, it is more preferred to be 15% by weight or more, it is still more preferred to be 20% by weight or more, it is yet still more preferred to be 25% by weight or more, it is particularly preferred to be 30% by weight or more, it is more particularly preferred to be 35% by weight or more, it is still more particularly preferred to be 40% by weight or more, and it is most preferred to be 45% by weight or more. It is preferred for the cyclic olefin-containing resin according to the present embodiment that the content of the polymer of a cyclic olefin and an acyclic olefin copolymerized should be 95% by weight or less based on the weight of the whole container, it is more preferred to be 90% by weight or less, it is still more preferred to be 85% by weight or less, it is yet still more preferred to be 80% by weight or less, it is particularly preferred to be 75% by weight or less, it is more particularly preferred to be 70% by weight or less, it is still more particularly preferred to be 65% by weight or less, and it is most preferred to be 60% by weight or less.

The cyclic olefin-containing resin may contain additives such as a stabilizer and a modifier. The cyclic olefin copolymer-containing resin may be reinforced by containing a reinforcing agent such as glass fiber.

The cyclic olefin-containing resin can employ a commercially available one without particular limitations. Examples of the commercially available product of the COP-containing resin include ZEONEX(R) (manufactured by Zeon Corp.) and ZEONOR(R) (manufactured by Zeon Corp.). Examples of the commercially available product of the COC-containing resin include TOPAS(R) (manufactured by Polyplastics Co., Ltd.) and APEL(R) (manufactured by Mitsui Chemicals, Inc.).

The kind of the cyclic olefin-containing resin container can be a container generally used in the ophthalmic field and specifically, can be, for example, a container for eye drops, a container for eye washes, a container for containing solutions for wearing a contact lens, and a container for containing solutions for contact lens care (including a container for containing contact lens cleaning solutions, a container for containing contact lens storage solutions, a container for containing contact lens disinfecting solutions, a container for containing contact lens multi-purpose solutions, and the like). It is preferred that the kind of the cyclic olefin-containing resin container should be a container for eye drops, a container for containing solutions for wearing a contact lens, or a container for containing solutions for contact lens care. Note that the "contact lens" includes hard contact lenses and soft contact lenses (ionic and non-ionic lenses are both included and silicone hydro gel contact lenses and non-silicone hydro-gel contact lenses are both included). Examples of the part coming into contact with the ophthalmic composition in these containers include inside plugs, nozzles, and container inner surface (innermost layer in the case where the container has a structure consisting of a plurality of layers).

In the cyclic olefin-containing resin container according to the present embodiment, a portion or the whole of a part coming into contact with the ophthalmic composition is formed from the cyclic olefin-containing resin. For example, in the case where the cyclic olefin-containing resin container is a container having a nozzle, only the nozzle part may be formed from the cyclic olefin-containing resin, a containment part, etc. other than the nozzle may be formed from the cyclic olefin-containing resin, or the whole container may be formed from the cyclic olefin-containing resin.

Although a portion of the part coming into contact with the ophthalmic composition can be formed from the cyclic olefin-containing resin, it is preferred for the cyclic olefin-containing resin container that the whole of the part coming into contact with the ophthalmic composition should be formed from the cyclic olefin-containing resin, in view of still more significantly exerting the effect according to the first aspect of the present invention. in the case where a portion of the container is formed from the cyclic olefin-containing resin, the kind of a resin forming the other parts is not particularly limited, but one or more kinds of polymers selected from the group consisting of, for example, polyethylene terephthalate (PET), polystyrene (PS), acrylonitrile-butadiene-styrene (ABS), polycarbonate, polyethylene (PE), polypropylene (PP), polymethyl methacrylate, an ethylene-vinyl acetate copolymer and an ethylene-vinyl alcohol copolymer may be contained as a constituent.

The shape and capacity of the cyclic olefin-containing resin container are not particularly limited and can be appropriately set depending on the use. The cyclic olefin-containing resin container may be a container in which the composition in an amount of multiple (e.g., 25 or more) uses is contained, may be a container in which the composition in an amount of a small number of (e.g., 2 or more and less than 25) uses is contained, or may be a container in which the composition in an amount of a single use is contained.

In the case where the cyclic olefin-containing resin container is a container that contains eye drops or a solution for wearing a contact lens, the capacity can be, for example, 0.01 mL or larger and 50 mL or smaller, and it is preferred to be 0.05 mL or larger and 40 mL or smaller, and it is more preferred to be 0.1 mL or larger and 25 mL or smaller. In the case where the cyclic olefin-containing resin container is a container that contains eye drops or a solution for wearing a contact lens and is a container in which the number of uses is a small number (e.g., 2 or larger and less than 25) or a single use, the capacity can be, for example, 0.01 mL or larger and 7 mL or smaller, and it is preferred to be 0.05 mL or larger and 6 mL or smaller, it is more preferred to be 0.1 mL or larger and 5 mL or smaller, it is still more preferred to be 0.1 mL or larger and 3 mL or smaller, it is yet still more preferred to be 0.2 mL or larger and 2 mL or smaller, and it is particularly preferred to be 0.2 mL or larger and 1 mL or smaller. In the case where the cyclic olefin-containing resin container is a container that contains an eye wash or a solution for contact lens care, the capacity can be, for example, 40 mL or larger and 600 mL or smaller, and it is preferred to be 45 mL or larger and 550 mL or smaller. In the case where the cyclic olefin-containing resin container is a container that contains an eye wash or a solution for contact lens care and is a container in which the number of uses is a small number (e.g., 2 or larger and less than 25) or a single use, the capacity can be, for example, 10 mL or larger and 150 mL or smaller, and it is preferred to be 10 mL or larger and 130 mL or smaller.

The cyclic olefin-containing resin container may be a container with a composition containment part and a bung hole integrally formed, or may be a container having a nozzle. In the case where the cyclic olefin-containing resin container is a container that contains eye drops or a solution for wearing a contact lens and is a container in which the number of uses is a small number (e.g., 2 or larger and less than 25) or a single use; and the capacity is 0.1 mL or larger and 3 mL or smaller, it is preferred to be a container with a composition containment part and a bung hole integrally formed.

It is preferred that the cyclic olefin-containing resin container should be a container having transparency in view of being able to macroscopically observe the confirmation of foreign substances, the confirmation of a residual volume, etc. The cyclic olefin-containing resin container may be colorless or may be colored as long as having transparency. The cyclic olefin-containing resin container can be a container having transparency that secures internal visibility to the extent that the inside is macroscopically observable, and the entire surface of the container does not necessarily have to have uniform transparency as long as the internal visibility described above is secured in a part of the container. As the transparency, for example, the maximum value of light transmittance (hereinafter, also referred to as "maximum light transmittance") in a visible light region of wavelengths from 400 to 700 nm of the cyclic olefin-containing resin container can be 50% or more, and it is preferred to be 60% or more, it is more preferred to be 70% or more, and it is still more preferred to be 80% or more. The maximum light transmittance can be determined from each light transmittance obtained by using, for example, a microplate reader and measuring light transmittance at 10-nm intervals between wavelengths of 400 and 700 nm. Note that in the case where the inside plug part is formed from a cyclic olefin-containing resin and in the case where the maximum light transmittance cannot be measured due to its shape, size, etc., the maximum light transmittance can also be determined as to a commercially available cyclic olefin-containing resin similar thereto in transparency by macroscopic observation and regarded as the transparency of the inside plug. Alternatively, the transparency of the inside plug can also be confirmed by carrying out the Foreign Insoluble Matter Test specified by the Japanese Pharmacopoeia.

The thickness of the cyclic olefin-containing resin container can be from 0.01 to 3.0 mm, and it is preferred to be from 0.05 to 2.0 mm, it is more preferred to be from 0.1 to 1.5 mm, it is still more preferred to be from 0.1 to 1.2 mm, it is yet still more preferred to be from 0.1 to 1.0 mm, it is particularly preferred to be from 0.1 to 0.8 mm, it is more particularly preferred to be from 0.1 to 0.6 mm, it is still more particularly preferred to be from 0.1 to 0.5 mm, and it is most preferred to be from 0.1 to 0.4 mm, in view of more significantly exerting an effect of improving liquid cutting.

It is preferred that the amount of dropping per drop of the ophthalmic composition according to the present embodiment should be designed so as to be from 1 to 99 4, it is more preferred to be from 1 to 79 μL, it is still more preferred to be from 7 to 79 μL, it is yet still more preferred to be from 13 to 79 μt, and it is particularly preferred to be from 33 to 79 μL, in view of still more significantly exerting the effect according to the first aspect of the present invention.

For the ophthalmic composition according to the present embodiment, the capacity for the ophthalmic composition, the amount of dropping per drop, the size of the container, the shape of the inside plug, the shape of the bung hole, etc. can be appropriately designed such that the number of uses is a small number or a single use.

The ophthalmic composition according to the present embodiment may also be provided as an ophthalmic composition contained in a cyclic olefin-containing resin container. The first aspect of the present invention can also be interpreted as an ophthalmic product (eye drops, an eye wash, or a contact lens-related product, etc.) in which the ophthalmic composition of the first aspect of the present invention is contained in the cyclic olefin-containing resin container.

[2. Suppression of Wetting to Cyclic Olefin-Containing Resin]

The ophthalmic composition according to the present embodiment exhibits suppressed wetting to a resin containing a cyclic olefin. Thus, as one embodiment of the first aspect of the present invention, provided is a method for imparting an effect of suppressing wetting to a resin containing a cyclic olefin to an ophthalmic composition, comprising blending (A) one or more kinds selected from the group consisting of terpenoid, a tocopherol, and a benzyl ammonium compound and a salt thereof into the ophthalmic composition. As another embodiment of the first aspect of the present invention, provided is a method for suppressing wetting of an ophthalmic composition to a resin containing a cyclic olefin, comprising blending (A) one or more kinds selected from the group consisting of terpenoid, a tocopherol, and a benzyl ammonium compound and a salt thereof into the ophthalmic composition.

Note that, in the present embodiment, the kind and content, etc. of the component (A), the kinds and contents, etc. of other components, and the dosage form and use, etc. of the ophthalmic composition are as explained in [1. Ophthalmic Composition].

[3. Suppression of Change in Smell]

Provided that the ophthalmic composition contained in a container formed from a resin containing a cyclic olefin according to the present embodiment further contains the component (B), change in smell is suppressed, for example, by retaining the aromaticity or suppressing the odor. Thus, as one embodiment of the first aspect of the present invention, provided is a method for imparting an effect of suppressing change in smell to an ophthalmic composition, comprising blending (A) one or more kinds selected from the group consisting of terpenoid, a tocopherol, and a benzyl ammonium compound and a salt thereof, and (B) a buffer into the ophthalmic composition contained in a container formed from a resin containing a cyclic olefin. As another embodiment of the first aspect of the present invention, provided is a method for suppressing change in smell of an ophthalmic composition, comprising blending (A) one or more kinds selected from the group consisting of terpenoid, a tocopherol, and a benzyl ammonium compound and a salt thereof, and (B) a buffer into the ophthalmic composition contained in a container formed from a resin containing a cyclic olefin.

Note that, in the present embodiment, the kinds and contents, etc. of the component (A) and the component (B), the kinds and contents, etc. of other components, and the dosage form and use, etc. of the ophthalmic composition are as explained in [1. Ophthalmic Composition].

As one embodiment of the first aspect of the present invention, provided is a method for using an ophthalmic composition, the ophthalmic composition containing (A) one or more kinds selected from the group consisting of terpenoid, a tocopherol, and a benzyl ammonium compound and a salt thereof and contained in a container formed from a resin containing a cyclic olefin, wherein the number of uses is a small number or a single use. Note that, while suppression of liquid residues and improvement in liquid cutting are required for exerting the desired pharmacological effect, particularly, in a small number of uses or a single use, the ophthalmic composition containing (A) one or more kinds selected from the group consisting of terpenoid, a tocopherol, and a benzyl ammonium compound and a salt thereof according to the present embodiment is contained in a container Ruined from a resin containing a cyclic olefin and thereby produces an effect of suppressing liquid residues and improving liquid cutting.

[Examples of First Aspect of Present Invention]

Hereinafter, the first aspect of the present invention will be specifically explained based on Test Examples, however the first aspect of the present invention is not limited thereto.

[Testing Method: Method for Measuring Dynamic Contact Angle (Angle of Advance)]

The contact angle meter DM-501 (manufactured by Kyowa Interface Science Co., Ltd.) was used to measure the dynamic contact angle (angle of advance) of each test solution in accordance with the measurement procedure of the expansion and contraction method of the contact angle meter. The dynamic contact angle (angle of advance) is a contact angle when the interface between solid and liquid moves.

Specifically, each sheet-shaped container material (low-density polyethylene (LDPE), linear low-density polyethylene (LLDPE), polypropylene (PP), cyclic olefin copolymer (COC; TOPAS8007 (manufactured by Polyplastics Co., Ltd.)), or a resin containing two or more kinds thereof) of 0.2 mm in thickness was placed on the stage of the contact angle meter, and a test solution was placed in a dispenser. 1 μL of droplets of the test solution at room temperature was dropped onto each container material to form a hemispherical shape. Then, to the top of the hemispherical shape, the head of the liquid discharge unit of the dispenser was quickly attached. In the state, the test solution was continuously discharged at a discharge velocity of 6 μL/sec, and the shapes of the droplets were photographed from the side surface 15 times per 0.1 sec. In order to satisfy the same measurement conditions, test solutions to be paired in calculating the change rate of the dynamic contact angle employed each identical container material and were continuously measured under identical temperature conditions (at room temperature).

Then, the right and left contact angles were determined for each image using the analysis software FAMAS of the contact angle meter. Here, among angles formed by the tangent line drawn from the contact point P of the surface of each sheet-shaped container material of 0.2 mm in thickness, the test solution, and the air to the test solution and the tangent line drawn on the surface of each sheet-shaped container material, the contact angle means an angle at the side including the test solution. The two contact points P are present at the right and left sides for each of the droplets. As the droplets were expanded according to the discharge of the test solution, the contact angles changed and subsequently exhibited a behavior of becoming almost constant. Accordingly, the average of the right and left contact angles was calculated for each image; the averages were arranged in the order of photographing the images; five consecutive averages were selected; and the first average (average of the right and left contact angles in the image taken earliest among the five averages) when the standard deviation of the five averages firstly reached 2.0° or less was defined as the measurement value of the dynamic contact angle in this measurement. Note that regarding all the test solutions, after the standard deviation firstly reached 2.0° or less, no standard deviation larger than 2.0° was observed. In the case where the contact angle did not change in the course where the droplets were expanded, the measurement value of the dynamic contact angle was also obtained in accordance with the standard described above.

The procedure described above was repetitively performed three times as to each test solution, and the average of 3 measurement values obtained was regarded as the dynamic contact angle of the test solution. The standard deviation of the 3 measurement values was 2.0° or less in all the test solutions.

[Test Example 1: Dynamic Contact Angle (Angle of Advance) Evaluation (1)]

The test solution of each Test Example shown in Tables 1-1 to 1-3 was prepared by a conventional method. The unit of each component in Tables 1-1 to 1-3 is w/v %.

The dynamic contact angle of each test solution was determined (average of 3 measurement values) in accordance with the procedure shown in the testing method described above. Subsequently, the change rate of the dynamic contact angle of the test solution of Test Example with respect to the corresponding prescribed solution was calculated according to [Expression 1] given below. The calculated results are shown in Tables 1-1 to 1-3.

Change rate of the dynamic contact angle (%)={(dynamic contact angle of the test solution/dynamic contact angle of the corresponding prescribed solution)−1}×100   [Expression 1]

Note that the corresponding prescribed solution is a prescription in which the component (A) was excluded from the prescription of each test solution, and is Test Example 1-1 as to Test Example 1-2, Test Example 1-3 as to Test Example 1-4, Test Example 1-5 as to Test Example 1-6, Test Example 1-7 as to Test Example 1-8, Test Example 1-9 as to Test Example 1-10, Test Example 1-11 as to Test Example 1-12, Test Example 1-13 as to Test Examples 1-14 and 1-15, Test Example 1-16 as to Test Example 1-17, Test Example 1-18 as to Test Examples 1-19 to 1-22, Test Example 1-23 as to Test Examples 1-24 and 1-25, Test Example 1-26 as to Test Example 1-27, Test Example 1-28 as to Test Example 1-29, and Test Example 1-30 as to Test Example 1-31.

TABLE 1-1

|  | Test Example 1-1 | Test Example 1-2 | Test Example 1-3 | Test Example 1-4 | Test Example 1-5 | Test Example 1-6 |
|---|---|---|---|---|---|---|
| (A) l-Menthol | — | 0.005 | — | 0.005 | — | — |
| (A) Benzalkonium chloride | — | — | — | — | — | 0.001 |
| (A) d-α-Tocopherol acetate | — | — | — | — | — | — |
| Polysorbate 80 | — | — | — | — | — | — |
| Purified water | Balance | Balance | Balance | Balance | Balance | Balance |
| Container material | LDPE | LDPE | PP | PP | LDPE | LDPE |
| Change rate of dynamic contact angle (%) | — | −4.2% | — | −3.1% | — | −4.8% |

|  | Test Example 1-7 | Test Example 1-8 | Test Example 1-9 | Test Example 1-10 | Test Example 1-11 | Test Example 1-12 |
|---|---|---|---|---|---|---|
| (A) l-Menthol | — | — | — | — | — | — |
| (A) Benzalkonium chloride | — | 0.001 | — | — | — | — |
| (A) d-α-Tocopherol acetate | — | — | — | 0.0005 | — | 0.0005 |

TABLE 1-1-continued

| | | | | | | |
|---|---|---|---|---|---|---|
| Polysorbate 80 | — | — | 0.05 | 0.05 | 0.05 | 0.05 |
| Purified water | Balance | Balance | Balance | Balance | Balance | Balance |
| Container material | PP | PP | LDPE | LDPE | PP | PP |
| Change rate of dynamic contact angle (%) | — | −5.6% | — | −8.3% | — | −12.0% |

TABLE 1-2

| | Test Example 1-13 | Test Example 1-14 | Test Example 1-15 | Test Example 1-16 | Test Example 1-17 | Test Example 1-18 | Test Example 1-19 | Test Example 1-20 | Test Example 1-21 | Test Example 1-22 |
|---|---|---|---|---|---|---|---|---|---|---|
| (A) l-Menthol | — | 0.005 | 0.005 | 0.015 | 0.015 | — | — | — | — | — |
| (A) Benzalkonium chloride | — | — | — | — | — | — | 0.001 | 0.02 | 0.01 | 0.01 |
| Purified water | Balance | Balance | Balance | Balance | Balance | Balance | Balance | Balance | Balance | Balance |
| Container material | COC | COC | COC + LDPE 10% | COC | COC + LDPE 2% | COC | COC | COC + LDPE 10% | COC | COC + LDPE 2% |
| Change rate of dynamic contact angle (%) | — | 6.1% | 10.0% | — | 14.2% | — | 6.0% | 8.5% | 6.8% | 7.4% |

*: In Test Examples 1-15 and 1-20, a container material containing 90 w/w % of a cyclic olefin copolymer (COC) and 10 w/w % of low-density polyethylene (LDPE) was used.
**: In Test Examples 1-17 and 1-22, a container material containing 98 w/w % of a cyclic olefin copolymer (COC) and 2 w/w % of low-density polyethylene (LDPE) was used.

TABLE 1-3

| | Test Example 1-23 | Test Example 1-24 | Test Example 1-25 | Test Example 1-26 | Test Example 1-27 | Test Example 1-28 | Test Example 1-29 | Test Example 1-30 | Test Example 1-31 |
|---|---|---|---|---|---|---|---|---|---|
| (A) d-α-Tocopherol acetate | — | 0.0005 | 0.0005 | — | 0.05 | — | 0.01 | — | 0.01 |
| Polysorbate 80 | 0.05 | 0.05 | 0.05 | — | — | 0.2 | 0.2 | 0.04 | 0.04 |
| Polyoxyethylene hydrogenated castor oil 60 | — | — | — | 0.3 | 0.3 | — | — | — | — |
| Purified water | Balance | Balance | Balance | Balance | Balance | Balance | Balance | Balance | Balance |
| Container material | COC | COC | COC + LDPE 10% | COC | COC | COC + LDPE 10% | COC + LDPE 10% | COC | COC + LDPE 2% |
| Change rate of dynamic contact angle (%) | — | 7.9% | 10.0% | — | 11.2% | — | 14.8% | — | 10.9% |

*: In Test Examples 1-25, 1-28, and 1-29, a container material containing 90 w/w % of a cyclic olefin copolymer (COC) and 10 w/w % of low-density polyethylene (LDPE) was used.
**: In Test Example 1-31, a container material containing 98 w/w % of a cyclic olefin copolymer (COC) and 2 w/w % of low-density polyethylene (LDPE) was used.

As shown in Table 1-1, it is evident that when low-density polyethylene (LDPE) or polypropylene (PP) is used as a container material, the dynamic contact angle of the test solution containing the component (A) is smaller than the dynamic contact angle of the test solution containing no component (A). Specifically, it was revealed that the composition containing the component (A) has a problem that the dynamic contact angle to a resin containing low-density polyethylene (LDPE) or polypropylene (PP) is small and wetting occurs easily.

On the other hand, as shown in Tables 1-2 and 1-3, when a cyclic olefin copolymer (COC) is used as container material, the dynamic contact angle of the test solution containing the component (A) is larger than the dynamic contact angle of the test solution containing no component (A), and wetting to the container can be suppressed. When a resin further containing low-density polyethylene (LDPE) in addition to a cyclic olefin copolymer (COC)° is used as a container material, the dynamic contact angle is much larger, and wetting to the container can be further suppressed, as compared with a resin containing only a cyclic olefin copolymer (COC). Note that similar effects were also exhibited in the case of using, as a container material, a resin containing a cyclic olefin copolymer (COC) and polyethylene (PE), wherein the content of the polyethylene (PE) was larger than 10 w/w % and 50 w/w % or smaller.

[Test Example 2: Dynamic Contact Angle (Angle of Advance) Evaluation (2)]

The test solution of each Test Example shown in Table 1-4 and a prescribed solution corresponding to each Test Example were prepared by a conventional method. The unit of each component in Table 1-4 is w/v %. Note that the corresponding prescribed solution is a prescription in which components other than the component (A) were excluded from the prescription of each test solution, and the pH was adjusted with appropriate amounts of hydrochloric acid and sodium hydroxide (the balance was purified water). All the container materials were a cyclic olefin copolymer (COC).

The dynamic contact angle of the test solution of each Test Example was determined (average of 3 measurement values) in accordance with the procedure shown in the testing method described above. Subsequently, the change rate of the dynamic contact angle of the test solution of each Test Example with respect to the corresponding prescribed solution was calculated according to [Expression 2] given below.

Change rate of the dynamic contact angle (%)=
{(dynamic contact angle of the test solution of each Test Example/dynamic contact angle of the corresponding prescribed solution)−1}×100   [Expression 2]

The osmotic pressure ratios of the test solutions were determined as a ratio of an osmotic pressure of a test solution to 286 mOsm (osmotic pressure of a 0.9 w/v % sodium chloride aqueous solution) based on the Japanese Pharmacopoeia, 16th version. Specifically, it was measured on the basis of the osmometry determination described in the Japanese Pharmacopoeia (cryoscopic method). The standard solution for osmotic pressure ratio measurement (0.9 w/v % sodium chloride aqueous solution) employed a commercially available standard solution for osmotic pressure ratio measurement (0.9 w/v % sodium chloride aqueous solution).

TABLE 1-4

| | Test Example 2-1 | Test Example 2-2 | Test Example 2-3 | Test Example 2-4 | Test Example 2-5 | Test Example 2-6 | Test Example 2-7 | Test Example 2-8 | Test Example 2-9 | Test Example 2-10 |
|---|---|---|---|---|---|---|---|---|---|---|
| (A) l-Menthol | 0.02 | 0.02 | 0.02 | — | — | — | — | — | — | — |
| (A) d-α-Tocopherol acetate | — | — | — | 0.01 | 0.01 | 0.01 | — | — | — | — |
| (A) Benzalkonium chloride | — | — | — | — | — | — | 0.008 | 0.008 | 0.008 | 0.008 |
| (B) Boric acid | 0.9 | — | — | 2.69 | — | — | 1.8 | — | — | 1.2 |
| (B) Borax | 0.2 | — | — | 0.2 | — | — | 0.3 | — | — | 0.15 |
| (B) Sodium hydrogen phosphate | — | 1.2 | — | — | 0.7 | — | — | 1 | — | — |
| (B) Sodium dihydrogen phosphate | — | 0.25 | — | — | 1.66 | — | — | 0.2 | — | — |
| (B) Citric acid | — | — | 0.06 | — | — | 0.21 | — | — | 0.15 | — |
| (B) Sodium citrate | — | — | 3.3 | — | — | 2 | — | — | 1 | — |
| (B) Epsilon aminocaproic acid | — | — | — | — | — | — | — | — | — | 1.5 |
| Polysorbate 80 | — | — | — | 0.04 | 0.04 | 0.04 | — | — | — | — |
| Hydrochloric acid | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance |
| pH | 7.2 | 7.2 | 7.2 | 5.2 | 5.2 | 5.2 | 6.5 | 6.5 | 6.5 | 6.5 |
| Osmotic pressure ratio | 0.6 | 0.7 | 1.5 | 1.6 | 1.2 | 1.6 | 1.2 | 0.6 | 1 | 1.6 |
| Change rate of dynamic contact angle (%) | 10.6% | 9.8% | 2.0% | 10.1% | 11.0% | 1.6% | 8.3% | 6.8% | 2.5% | 13.4% |

As shown in Table 1-4, in the ophthalmic composition containing the component (A) and the component (B) in combination, the dynamic contact angle is larger, and wetting to the container can be suppressed, as compared with the test solution containing only the component (A). Note that similar effects were also exhibited in the case of using, as a container material, a resin containing a cyclic olefin copolymer (COC) and polyethylene (PE), wherein the content of the polyethylene (PE) was 50 w/w % or smaller.

[Test Example 3: Dynamic Contact Angle (Angle of Advance) Evaluation (3)]

The test solution of each Test Example shown in Tables 1-5 to 1-7 was prepared by a conventional method. The unit of each component in Tables 1-5 to 1-7 is w/v %. Note that the corresponding prescribed solution is a prescription in which the component (A) and ethanol were excluded from the prescription of each test solution. Note that the corresponding prescribed solution was Test Example 3-5 as to Test Example 3-6 to Test Example 3-8. All the container materials were a cyclic olefin copolymer (COC).

The dynamic contact angle of the test solution of each Test Example was determined (average of 3 measurement values) in accordance with the procedure shown in the testing method described above. Subsequently, the change rate of the dynamic contact angle of the test solution of each Test Example with respect to the corresponding prescribed solution was calculated according to [Expression 3] given below.

Change rate of the dynamic contact angle (%)=
{(dynamic contact angle of the test solution of each Test Example/dynamic contact angle of the corresponding prescribed solution)−1}×100   [Expression 3]

TABLE 1-5

| | Test Example 3-1 | Test Example 3-2 | Test Example 3-3 | Test Example 3-4 |
|---|---|---|---|---|
| (A) l-Menthol | 0.015 | 0.015 | 0.015 | 0.015 |
| Ethanol | 0.5 | 3 | 10 | 15 |
| Purified water | Balance | Balance | Balance | Balance |
| Change rate of dynamic contact angle (%) | 7.0% | 5.7% | 4.9% | 3.4% |

TABLE 1-6

| | Test Example 3-5 | Test Example 3-6 | Test Example 3-7 | Test Example 3-8 |
|---|---|---|---|---|
| (A) d-α-Tocopherol acetate | — | 0.008 | 0.008 | 0.008 |
| Polysorbate 80 | 0.1 | 0.1 | 0.1 | 0.1 |
| Ethanol | — | 0 | 4 | 15 |
| Purified water | Balance | Balance | Balance | Balance |
| Change rate of dynamic contact angle (%) | — | 18.9% | 18.4% | 1.6% |

TABLE 1-7

| | Test Example 3-9 | Test Example 3-10 | Test Example 3-11 | Test Example 3-12 |
|---|---|---|---|---|
| (A) Benzalkonium chloride | 0.01 | 0.01 | 0.01 | 0.01 |

TABLE 1-7-continued

|  | Test Example 3-9 | Test Example 3-10 | Test Example 3-11 | Test Example 3-12 |
|---|---|---|---|---|
| Ethanol | 0 | 2 | 10 | 15 |
| Purified water | Balance | Balance | Balance | Balance |
| Change rate of dynamic contact angle (%) | 6.8% | 6.5% | 6.0% | 3.6% |

As shown in Tables 1-5 to 1-7, in the test solution in which the content of water is 84.892% (w/v) or more, the dynamic contact angle is large, and wetting to the container can be suppressed. Note that similar effects were also exhibited in the case of using, as a container material, a resin containing a cyclic olefin copolymer (COC) and polyethylene (PE), wherein the content of the polyethylene (PE) was 50 w/w % or smaller.

[Test Example 4: Dynamic Contact Angle (Angle of Advance) Evaluation (4)]

The test solution of each Test Example shown in Tables 1-8 to 1-10 was prepared by a conventional method. The unit of each component in Tables 1-8 to 1-10 is w/v %. Note that the corresponding prescribed solution is a prescription in which the component (A) was excluded from the prescription of each test solution. All the container materials were a cyclic olefin copolymer (COC).

The dynamic contact angle of the test solution of each Test Example was determined (average of 3 measurement values) in accordance with the procedure shown in the testing method described above. However, the contact angle (average of the right and left contact angles) at the time when the solution was discharged in an amount of 10% of the amount of droplets dropped onto each container material was measured three times, and the average thereof was regarded as the dynamic contact angle of Test Example. The total of the amount of dropping and the amount of discharge, which is the amount of droplets when the dynamic contact angle was measured, is as shown as the amount of droplets in Tables 1-8 to 1-10. Subsequently, the change rate of the dynamic contact angle of the test solution of each Test Example with respect to the corresponding prescribed solution was calculated according to [Expression 4] given below.

Change rate of the dynamic contact angle (%)=
{(dynamic contact angle of the test solution of each Test Example/dynamic contact angle of the corresponding prescribed solution)−1}×100    [Expression 4]

TABLE 1-8

|  | Test Example 4-1 | Test Example 4-2 | Test Example 4-3 | Test Example 4-4 |
|---|---|---|---|---|
| (A) l-Menthol | 0.01 | 0.01 | 0.01 | 0.01 |
| Purified water | Balance | Balance | Balance | Balance |

TABLE 1-8-continued

|  | Test Example 4-1 | Test Example 4-2 | Test Example 4-3 | Test Example 4-4 |
|---|---|---|---|---|
| Amount of droplet (μl) | 7 | 33 | 59 | 79 |
| Change rate of dynamic contact angle (%) | 0.9% | 0.8% | 1.7% | 1.6% |

TABLE 1-9

|  | Test Example 4-5 | Test Example 4-6 | Test Example 4-7 | Test Example 4-8 | Test Example 4-9 |
|---|---|---|---|---|---|
| (A) d-α-Tocopherol acetate | 0.01 | 0.01 | 0.01 | 0.01 | 0.01 |
| Polysorbate 80 | 0.05 | 0.05 | 0.05 | 0.05 | 0.05 |
| Purified water | Balance | Balance | Balance | Balance | Balance |
| Amount of droplet (μl) | 13 | 33 | 59 | 79 | 99 |
| Change rate of dynamic contact angle (%) | 6.9% | 9.2% | 10.1% | 10.0% | 7.0% |

TABLE 1-10

|  | Test Example 4-10 | Test Example 4-11 | Test Example 4-12 | Test Example 4-13 |
|---|---|---|---|---|
| (A) Benzalkonium chloride | 0.015 | 0.015 | 0.015 | 0.015 |
| Purified water | Balance | Balance | Balance | Balance |
| Amount of droplet (μl) | 7 | 33 | 59 | 79 |
| Change rate of dynamic contact angle (%) | 2.4% | 3.1% | 2.8% | 2.9% |

As shown in Tables 1-8 and 1-10, in the test solution containing l-menthol as the component (A), and the test solution containing benzalkonium chloride, the dynamic contact angle of the test solution in which the amount of droplets is 79 μl or smaller is larger than that of the test solution containing no component (A), and wetting to the container can be suppressed.

As shown in Table 1-9, in the test solution containing d-α-tocopherol acetate as the component (A), the dynamic contact angle of the test solution in which the amount of droplets is 99 μl or smaller is larger than that of the test solution containing no component (A), and wetting to the container can be suppressed.

Note that similar effects were also exhibited in the case of using, as a container material, a resin containing a cyclic olefin copolymer (COC) and polyethylene (PE), wherein the content of the polyethylene (PE) was 50 w/w % or smaller.

[Test Example 5: Sensory Evaluation (1)]

The test solution of each Test Example shown in Table 1-11 was prepared by a conventional method and filled in 1 mL each in 5 mL glass ampules. The unit of each component in Table 1-11 is w/v %. Further, container material strips of 2 mm in width, 20 mm in length, and 0.2 mm in thickness were dipped therein one by one and immediately sealed hermetically. The container material was a cyclic olefin copolymer (COC; TOPAS8007 (manufactured by Polyplastics Co., Ltd.)). Then, heat treatment of still standing at 60° C. for 5 hours was performed in a thermostat. Thereafter, 20 μL of each test solution before and after the heat treatment was dropped onto the arms of four subjects sensitive to smell, spread in a circle of approximately 2 cm in diameter with their fingers, and evaluated by the VAS (visual analog scale) method after sniffing. Specifically, as to "aromaticity", the subjects pointed at one point on a straight line corresponding to the aroma of each test solution when "not felt" was defined as 0 mm and "very felt" was defined as 100 mm on both ends of the 100 mm straight line. The distance (mm) from the point of 0 mm was measured, and the average from the four subjects was calculated and regarded as the VAS value of the test solution. Subsequently, the value of change in VAS between before and after the heat treatment was calculated according to [Expression 5-1] given below. Thereafter, the aromaticity retention rate of the test solution of Test Example with respect to Test Example 5-1 in which the container material was not dipped was calculated according to [Expression 5-2] given below. The calculated results are shown in Table 1-11.

Value of change in VAS=VAS value of the test solution before the heat treatment−VAS value of the test solution after the heat treatment      [Expression 5-1]

Aromaticity retention rate (%)={1 − (value of change in VAS of each Test Example/value of change in VAS of Test Example 5-1)}×100      Expression 5-2]

as compared with Test Example 5-1 in which the COC-containing resin container material was not dipped in the test solution containing the component (A). Note that similar effects were also exhibited in the case of using, as a container material, a resin containing a cyclic olefin copolymer (COC) and polyethylene (PE), wherein the content of the polyethylene (PE) was 50 w/w or smaller.

[Test Example 6: Sensory Evaluation (2)]

The test solution of each Test Example shown in Table 1-12 was prepared by a conventional method and filled in 1 mL each in 5 mL glass ampules. The unit of each component in Table 1-12 is w/v Further, container material strips of 2 mm in width, 20 mm in length, and 0.2 mm in thickness were dipped therein one by one and immediately sealed hermetically. The container material was a cyclic olefin copolymer (COC; TOPAS8007 (manufactured by Polyplastics Co., Ltd.)) or a container material containing 90 w/w % of COC and 10 w/w % of low-density polyethylene (LDPE). Then, heat treatment of still standing at 70° C. for 2 days was performed in a thermostat. Thereafter, 20 μL of each test solution before and after the heat treatment was dropped onto the arms of four subjects sensitive to smell, spread in a circle of approximately 2 cm in diameter with their fingers, and evaluated by the VAS (visual analog scale) method after sniffing. Specifically, as to "odor", the subjects pointed at one point on a straight line corresponding to the odor of each test solution when "not felt" was defined as 0 mm and "very felt" was defined as 100 mm on both ends of the 100 mm straight line. The distance (mm) from the point of 0 mm was measured, and the average from the four subjects was calculated and regarded as the VAS value of the test solution.

TABLE 1-11

| | Test Example 5-1 | Test Example 5-2 | Test Example 5-3 | Test Example 5-4 | Test Example 5-5 | Test Example 5-6 | Test Example 5-7 | Test Example 5-8 |
|---|---|---|---|---|---|---|---|---|
| (A) l-Menthol | 0.04 | 0.04 | 0.04 | 0.04 | 0.04 | 0.04 | 0.04 | 0.04 |
| (B) Boric acid | — | — | 0.9 | — | — | — | — | — |
| (B) Borax | — | — | 0.1 | — | — | — | — | — |
| (B) Sodium hydrogen phosphate | — | — | — | 0.5 | — | — | — | — |
| (B) Sodium dihydrogen phosphate | — | — | — | 0.25 | — | — | — | — |
| (B) Citric acid | — | — | — | — | 0.02 | — | — | — |
| (B) Sodium citrate | — | — | — | — | 0.8 | — | — | — |
| (B) Epsilon aminocaproic acid | — | — | — | — | — | 0.5 | — | — |
| (B) Trometamol | — | — | — | — | — | — | 1 | — |
| (B) Sodium hydrogen carbonate | — | — | — | — | — | — | — | 0.5 |
| Hydrochloric acid | q.s | q.s | q.s | q.s | q.s | q.s | q.s | q.s |
| Sodium hydroxide | q.s | q.s | q.s | q.s | q.s | q.s | q.s | q.s |
| Purified water | Balance | Balance | Balance | Balance | Balance | Balance | Balance | Balance |
| pH | 7.7 | 7.7 | 7.7 | 7.7 | 7.7 | 7.7 | 7.7 | 7.7 |
| Container material | None | COC | COC | COC | COC | COC | COC | COC |
| Aromaticity retention rate (%) | — | −39% | 35% | 63% | 11% | 41% | 27% | 45% |

As shown in Table 1-11, in Test Example 5-2 in which the COC-containing resin container material was dipped in the test solution containing the component (A), the aromaticity retention rate was deteriorated as compared with Test Example 5-1 in which the COC-containing resin container material was not dipped in the test solution containing the component (A). On the other hand, in Test Example 5-3 to Test Example 5-8 containing the component (A) and the component (B), the aromaticity retention rate was improved Subsequently, the improvement rate of smell between before and after the heat treatment was calculated according to [Expression 6] given below. The calculated results are shown in Table 1-12.

Improvement rate of smell (%)={1−(VAS value of the test solution after the heat treatment/VAS value of the test solution before the heat treatment)}×100      [Expression 6]

TABLE 1-12

|  | Test Example 5-10 | Test Example 5-11 | Test Example 5-12 | Test Example 5-13 | Test Example 5-14 | Test Example 5-15 | Test Example 5-16 | Test Example 5-17 |
|---|---|---|---|---|---|---|---|---|
| (A) d-α-Tocopherol acetate | 0.05 | 0.05 | 0.05 | 0.05 | 0.05 | 0.05 | 0.05 | 0.05 |
| (B) Boric acid | — | 0.2 | — | — | — | — | — | — |
| (B) Borax | — | 0.07 | — | — | — | — | — | — |
| (B) Sodium hydrogen phosphate | — | — | 0.8 | — | — | — | — | — |
| (B) Sodium dihydrogen phosphate | — | — | 0.8 | — | — | — | — | — |
| (B) Citric acid | — | — | — | 0.01 | — | — | — | — |
| (B) Sodium citrate | — | — | — | 0.5 | — | — | — | — |
| (B) Epsilon aminocaproic acid | — | — | — | — | 4 | — | — | — |
| (B) Trometamol | — | — | — | — | — | 1.5 | — | — |
| (B) Sodium hydrogen carbonate | — | — | — | — | — | — | 1 | — |
| (B) Sodium acetate | — | — | — | — | — | — | — | 0.05 |
| Polysorbate 80 | 0.2 | 0.2 | 0.2 | 0.2 | 0.2 | 0.2 | 0.2 | 0.2 |
| Hydrochloric acid | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. |
| Purified water | Balance | Balance | Balance | Balance | Balance | Balance | Balance | Balance |
| pH | 7.0 | 7.0 | 7.0 | 7.0 | 7.0 | 7.0 | 7.0 | 7.0 |
| Improvement rate of smell (%) (container material: COC) | −250% | 19% | 66% | 50% | 6% | 60% | 40% | — |
| Improvement rate of smell (%) (container material: COC and LDPE) | −29% | 45% | 93% | 84% | 71% | 86% | 91% | 94% |

As shown in Table 1-12, in Test Example 5-10 containing the component (A), the odor was deteriorated after the heat treatment. On the other hand, in Test Example 5-11 to Test Example 5-17 containing the component (A) and the component (B), the smell was improved after the heat treatment. Note that similar effects were also exhibited in the case of using, as a container material, a resin containing a cyclic olefin copolymer (COC) and polyethylene (PE), wherein the content of the polyethylene (PE) was larger than 10 w/w % and 50 w/w % or smaller.

[Test Example 7: Dynamic Contact Angle (Angle of Advance) Evaluation (5)]

The test solution of each Test Example shown in Tables 1-13 to 1-16 was prepared by a conventional method. The unit of each component in Tables 1-13 to 1-16 is w/v %. The container material was a resin containing a cyclic olefin copolymer (COC; TOPAS8007 (manufactured by Polyplastics Co., Ltd.)), or a resin containing COC and low-density polyethylene (LDPE) or linear low-density polyethylene (LLDPE), and the unit of each constituent contained in the container material in Tables 1-13 to 1-16 is w/w %.

The dynamic contact angle of each test solution was determined (average of 3 measurement values) in accordance with the procedure shown in the testing method described above. Subsequently, the change rate of the dynamic contact angle of the test solution of Test Example with respect to the corresponding prescribed solution was calculated according to [Expression 7] given below. The calculated results are shown in Tables 1-13 to 1-16.

Change rate of the dynamic contact angle (%)= {(dynamic contact angle of the test solution/ dynamic contact angle of the corresponding prescribed solution)−1}×100    [Expression 7]

Note that the corresponding prescribed solution is Test Example 1-13 as to Test Examples 7-1 to 7-6, Test Example 7-7 as to Test Examples 7-8 and 7-9, Test Example 1-13 as to Test Examples 7-10 to 7-12, Test Example 7-13 as to Test Examples 7-14 to 7-17, Test Example 7-18 as to Test Examples 7-19 to 7-24, Test Example 7-25 as to Test Examples 7-26 to 7-28, and Test Example 7-29 as to Test Examples 7-30 to 7-32.

TABLE 1-13

|  |  | Test Example 7-1 | Test Example 7-2 | Test Example 7-3 | Test Example 7-4 | Test Example 7-5 | Test Example 7-6 | Test Example 7-7 | Test Example 7-8 | Test Example 7-9 |
|---|---|---|---|---|---|---|---|---|---|---|
| (A) l-Menthol |  | 0.004 | 0.004 | 0.004 | 0.004 | 0.004 | 0.004 | — | 0.004 | 0.004 |
| Polysorbate 80 |  | — | — | — | — | — | — | 0.2 | 0.2 | 0.2 |
| Purified water |  | Balance | Balance | Balance | Balance | Balance | Balance | Balance | Balance | Balance |
| Container material | COC | 100 | 70 | 50 | 90 | 70 | 55 | 70 | 70 | 70 |
|  | LDPE | — | 30 | 50 | — | — | — | 30 | 30 | — |
|  | LLDPE | — | — | — | 10 | 30 | 45 | — | — | 30 |
| Change rate of dynamic contact angle (%) |  | 5.5% | 11.1% | 14.0% | 11.6% | 14.6% | 17.4% | — | 12.1% | 16.6% |

TABLE 1-14

|  | Test Example 7-10 | Test Example 7-11 | Test Example 7-12 | Test Example 7-13 | Test Example 7-14 | Test Example 7-15 | Test Example 7-16 | Test Example 7-17 |
|---|---|---|---|---|---|---|---|---|
| (A) Benzalkonium chloride | 0.005 | 0.005 | 0.005 | — | — | — | — | — |
| (A) d-α-Tocopherol acetate | — | — | — | 0.005 | 0.005 | 0.005 | 0.005 | 0.005 |
| Polyoxyethylene hydrogenated castor oil 60 | — | — | — | 0.05 | 0.05 | 0.05 | 0.05 | 0.05 |
| Purified water | Balance | Balance | Balance | Balance | Balance | Balance | Balance | Balance |
| Container material  COC | 70 | 90 | 70 | 90 | 70 | 50 | 90 | 70 |
| LDPE | 30 | — | — | 10 | 30 | 50 | — | — |
| LLDPE | — | 10 | 30 | — | — | — | 10 | 30 |
| Change rate of dynamic contact angle (%) | 9.0% | 9.5% | 11.7% | — | 4.6% | 7.6% | 2.2% | 8.9% |

TABLE 1-15

|  | Test Example 7-18 | Test Example 7-19 | Test Example 7-20 | Test Example 7-21 | Test Example 7-22 | Test Example 7-23 | Test Example 7-24 |
|---|---|---|---|---|---|---|---|
| (A) l-Menthol | 0.01 | 0.01 | 0.01 | 0.01 | 0.01 | 0.01 | 0.01 |
| (B) Boric acid | — | 0.5 | 0.5 | 0.5 | 0.5 | 0.5 | 0.5 |
| (B) Borax | — | 0.05 | 0.05 | 0.05 | 0.05 | 0.05 | 0.05 |
| Hydrochloric acid | q.s. | q.s. | q.s. | q.s. | q.s. | q.s. | q.s. |
| Sodium hydroxide | q.s. | q.s. | q.s. | q.s. | q.s. | q.s. | q.s. |
| Purified water | Balance | Balance | Balance | Balance | Balance | Balance | Balance |
| pH | 7 | 7 | 7 | 7 | 7 | 7 | 7 |
| Container material  COC | 100 | 100 | 70 | 50 | 90 | 70 | 55 |
| LDPE | — | — | 30 | 50 | — | — | — |
| LLDPE | — | — | — | — | 10 | 30 | 45 |
| Change rate of dynamic contact angle (%) | — | 4.1% | 7.3% | 9.1% | 6.6% | 9.5% | 11.9% |

TABLE 1-16

|  | Test Example 7-25 | Test Example 7-26 | Test Example 7-27 | Test Example 7-28 | Test Example 7-29 | Test Example 7-30 | Test Example 7-31 | Test Example 7-32 |
|---|---|---|---|---|---|---|---|---|
| (A) Benzalkonium chloride | 0.005 | 0.005 | 0.005 | 0.005 | — | — | — | — |
| (A) d-α-Tocopherol acetate | — | — | — | — | 0.01 | 0.01 | 0.01 | 0.01 |
| (B) Trometamol | — | 0.2 | 0.2 | 0.2 | — | — | — | — |
| (B) Epsilon aminocaproic acid | — | — | — | — | — | 2 | 2 | 2 |
| Polyoxyethylene hydrogenated castor oil 60 | — | — | — | — | 0.05 | 0.05 | 0.05 | 0.05 |
| Hydrochloric acid | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. |
| Purified water | Balance | Balance | Balance | Balance | Balance | Balance | Balance | Balance |
| pH | 5 | 5 | 5 | 5 | 7 | 7 | 7 | 7 |
| Container material  COC | 100 | 100 | 70 | 70 | 100 | 100 | 70 | 70 |
| LDPE | — | — | 30 | — | — | — | 30 | — |
| LLDPE | — | — | — | 30 | — | — | — | 30 |
| Change rate of dynamic contact angle (%) | — | 4.5% | 7.3% | 8.6% | — | 3.7% | 7.0% | 8.6% |

When COC is used as a container material, the dynamic contact angle of the test solution containing the component (A) is larger than the dynamic contact angle of the test solution containing no component (A), and wetting to the container can be suppressed. When a resin further containing LDPE or LLDPE in addition to COC is used as a container material, the dynamic contact angle is much larger, and wetting to the container can be further suppressed, as compared with a resin containing only COC. The dynamic contact angle was yet much larger, particularly, for the resin containing COC and LLDPE.

[Test Example 8: Sensory Evaluation (3)]

The test solution of each Test Example shown in Table 1-17 was prepared by a conventional method and filled in 1 mL each in 5 mL glass ampules. The unit of each component in Table 1-17 is w/v %. Further, container material strips of 2 mm in width, 20 mm in length, and 0.2 mm in thickness were dipped therein one by one and immediately sealed hermetically. The container material was a resin containing a cyclic olefin copolymer (COC; TOPAS8007 (manufactured by Polyplastics Co., Ltd.)), or a resin containing COC and low-density polyethylene (LDPE) or linear low-density polyethylene (LLDPE), and the unit of each constituent contained in the container material in Table 1-17 is w/w %. Then, heat treatment of still standing at 60° C. for 5 hours was performed in a thermostat. Thereafter, 20 μL of each test solution before and after the heat treatment was dropped onto the arms of four subjects sensitive to smell, spread in a circle of approximately 2cm in diameter with their fingers, and evaluated by the VAS (visual analog scale) method after sniffing. Specifically, as to "aromaticity", the subjects pointed at one point on a straight line corresponding to the aroma of each test solution when "not felt" was defined as 0 mm and "very felt" was defined as 100 mm on both ends of the 100 mm straight line. The distance (mm) from the point of 0 mm was measured, and the average from the four subjects was calculated and regarded as the VAS value of the test solution. Subsequently, the value of change in VAS between before and after the heat treatment was calculated according to [Expression 8-1] given below. Thereafter, the aromaticity retention rate of the test solution of Test Example with respect to Test Example 8-1 in which the container material was not dipped was calculated according to [Expression 8-2] given below. The calculated results are shown in Table 1-17.

Value of change in VAS=VAS value of the test solution before the heat treatment−VAS value of the test solution after the heat treatment   [Expression 8-1]

Aromaticity retention rate (%)={1−(value of change in VAS of each Test Example/ value of change in VAS of Test Example 8-1)}×100   [Expression 8-2]

TABLE 1-17

|  | Test Example 8-1 | Test Example 8-2 | Test Example 8-3 | Test Example 8-4 | Test Example 8-5 | Test Example 8-6 | Test Example 8-7 |
|---|---|---|---|---|---|---|---|
| (A) l-Menthol | 0.02 | 0.02 | 0.02 | 0.02 | 0.02 | 0.02 | 0.02 |
| (B) Trometamol | — | — | 0.5 | 0.5 | 0.5 | 0.5 | 0.5 |
| Hydrochloric acid | q.s. | q.s. | q.s. | q.s. | q.s. | q.s. | q.s. |
| Sodium hydroxide | q.s. | q.s. | q.s. | q.s. | q.s. | q.s. | q.s. |
| Purified water | Balance | Balance | Balance | Balance | Balance | Balance | Balance |
| pH | 7.3 | 7.3 | 7.3 | 7.3 | 7.3 | 7.3 | 7.3 |
| Container material   COC | — | 100 | 100 | 70 | 50 | 70 | 55 |
| LDPE | — | — | — | 30 | 50 | — | — |
| LLDPE | — | — | — | — | — | 30 | 45 |
| Aromaticity retention rate (%) | — | −30% | 20% | 39% | 51% | 67% | 84% |

In Test Example 8-2 in which the COC-containing resin container material was dipped in the test solution containing the component (A), the aromaticity retention rate was deteriorated as compared with Test Example 8-1 in which the COC-containing resin container material was not dipped in the test solution containing the component (A). On the other hand, in Test Example 8-3 to Test Example 8-7 containing the component (A) and the component (B), the aromaticity retention rate was improved, as compared with Test Example 8-1 in which the COC-containing resin container material was not dipped in the test solution containing the component (A). In Test Example 8-4 to Test Example 8-7 using, as a container material, a resin containing COC and LDPE or COC and LLDPE, the aromaticity retention rate was further improved as compared with Test Example 8-1, and, particularly, when the resin containing COC and LLDPE is used as a container material, the aromaticity retention rate was yet further improved (Test Examples 8-6 and 8-7).

[Test Example 9: Sensory Evaluation (4)]

The test solution of each Test Example shown in Table 1-18 was prepared by a conventional method and filled in 1 mL each in 5 mL glass ampules. The unit of each component in Table 1-18 is w/v %. Further, container material strips of 2 mm in width, 20 mm in length, and 0.2 mm in thickness were dipped therein one by one and immediately sealed hermetically. The container material was a resin containing a cyclic olefin copolymer (COC; TOPAS8007 (manufactured by Polyplastics Co., Ltd.)), or a resin containing COC and low-density polyethylene (LDPE) or linear low-density polyethylene (LLDPE), and the unit of each constituent contained in the container material in Table 1-18 is w/w %. Then, heat treatment of still standing at 70° C. for 2 days was performed in a thermostat. Thereafter, 20 !L of each test solution before and after the heat treatment was dropped onto the arms of four subjects sensitive to smell, spread in a circle of approximately 2 cm in diameter with their fingers, and evaluated by the VAS (visual analog scale) method after sniffing. Specifically, as to "odor", the subjects pointed at one point on a straight line corresponding to the odor of each test solution when "not felt" was defined as 0 mm and "very felt" was defined as 100 mm on both ends of the 100 mm straight line. The distance (mm) from the point of 0 mm was measured, and the average from the four subjects was calculated and regarded as the VAS value of the test solution. Subsequently, the improvement rate of smell between before and after the heat treatment was calculated according to [Expression 9] given below. The calculated results are shown in Table 1-18.

Improvement rate of smell (%)=11−(VAS value of the test solution after the heat treatment/VAS value of the test solution before the heat treatment)}×100   [Expression 9]

TABLE 1-18

|  | Test Example 9-1 | Test Example 9-2 | Test Example 9-3 | Test Example 9-4 | Test Example 9-5 |
|---|---|---|---|---|---|
| (A) d-α-Tocopherol acetate | 0.01 | 0.01 | 0.01 | 0.01 | 0.01 |
| (B) Boric acid | — | 0.15 | 0.15 | 0.15 | 0.15 |

TABLE 1-18-continued

| | Test Example 9-1 | Test Example 9-2 | Test Example 9-3 | Test Example 9-4 | Test Example 9-5 |
|---|---|---|---|---|---|
| (B) Borax | — | 0.03 | 0.03 | 0.03 | 0.03 |
| Polyoxyethylene hydrogenated castor oil 60 | 1 | 1 | 1 | 1 | 1 |
| Hydrochloric acid | q.s. | q.s. | q.s. | q.s. | q.s. |
| Sodium hydroxide | q.s. | q.s. | q.s. | q.s. | q.s. |
| Purified water | Balance | Balance | Balance | Balance | Balance |
| pH | 6 | 6 | 6 | 6 | 6 |
| Container material COC | 100 | 100 | 70 | 70 | 55 |
| LDPE | — | — | 30 | — | — |
| LLDPE | — | — | — | 30 | 45 |
| Improvement rate of smell (%) | −25% | 8% | 16% | 38% | 48% |

In Test Example 9-1 containing the component (A), the odor was deteriorated after the heat treatment. On the other hand, in Test Examples 9-2 to 9-5 containing the component (A) and the component (B), the smell was improved after the heat treatment. In Test Example 9-3 to Test Example 9-5 using, as a container material, a resin containing COC and LDPE or COC and LLDPE, the smell was further improved as compared with Test Example 9-1, and particularly, when the resin containing COC and LLDPE is used as a container material, the smell was yet further improved (Test Examples 9-4 and 9-5).

From these results, the ophthalmic composition according to the present embodiment produces an effect of suppressing wetting; thus liquid residues are suppressed. This suppresses contamination attributed to mixing of bacteria or foreign substances, etc. and can achieve high sanitary quality required for delicate ocular mucosal tissues. Furthermore, the ophthalmic composition according to the present embodiment produces an effect of suppressing wetting; thus liquid cutting is improved. This can decrease variations in the amount of dropping required for the eyes, which are relatively small sites, or use in contact lenses. Moreover, the ophthalmic composition according to the present embodiment produces an effect of suppressing change in smell; thus, the generation of offensive smell by contact with a container can be suppressed.

The explanation about the first aspect of the present invention will now be completed, followed by the explanation about the second aspect of the present invention.

[Second Aspect of Present Invention]

The second aspect of the present invention relates to an ophthalmic composition.

[Background Art]

Surface active components may be blended into ophthalmic compositions (e.g., Patent Literature 2-1).

Meanwhile, polypropylene, polyethylene, and polyethylene terephthalate containers and the like are widely used as containers that contain ophthalmic drug products (e.g., Patent Literature 2-2).

[Citation List]
[Patent Literature]
[Patent Literature 2-1] Japanese Unexamined Patent Publication No. 2011-184463
[Patent Literature 2-2] Japanese Unexamined Patent Publication No. 2009-196988

[Summary of Second Aspect of Present Invention]
[Technical Problem of Second Aspect of Present Invention]

The present inventor has found a new problem that when a surface active component is contained in an ophthalmic composition, the dynamic contact angle to resins containing a cyclic olefin is small as compared with resins widely used, and wetting occurs easily. If wetting occurs easily to containers formed from these resins containing a cyclic olefin, liquid residues may be generated or liquid cutting may be deteriorated; thus there is a fear of inducing reduction in the quality and reduction in the use performance of the ophthalmic composition.

An object of the second aspect of the present invention is to provide an ophthalmic composition in which wetting to a container fanned from a resin containing a cyclic olefin is suppressed while containing a surface active component.

[Solution to Problem of Second Aspect of Present Invention]

The present inventor has found that in an ophthalmic composition containing (B2) a buffer in addition to (A2) a surface active component, the dynamic contact angle is increased (i.e., wetting is suppressed) even to a container formed from a resin containing a cyclic olefin.

Also, the present inventor has found a new problem that in the case where the ophthalmic composition containing one kind of component (A2) and the component (B2) is contained in a container formed from a resin containing a cyclic olefin, odor is deteriorated during preservation, and found that in response to this, an ophthalmic composition further containing one or more kinds of components (A2) different from the one kind of component (A2), unexpectedly, suppresses change in smell, for example, by improving the odor.

The second aspect of the present invention is based on this finding and provides each of the following embodiments:

[1] An ophthalmic composition comprising
(A2) a surface active component and (B2) a buffer, wherein
the ophthalmic composition is contained in a container in which a portion or the whole of a part coming into contact with the ophthalmic composition is formed from a resin containing a cyclic olefin.

[2] The ophthalmic composition according to [1], wherein the resin forming the container further contains polyethylene.

[3] The ophthalmic composition according to [1] or [2], wherein two or more kinds of the surface active component (A2) are contained.

[4] The ophthalmic composition according to any one of [1] to [3], wherein a total content of the component (A2) is from 0.00001 to 10 w/v % based on the total amount of the ophthalmic composition.

[5] The ophthalmic composition according to any one of [1] to [4], wherein a total content of the component (B2) is from 0.001 to 8000 parts by weight based on 1 part by weight of the total content of the component (A2).

[6] The ophthalmic composition according to any one of [1] to [5], wherein pH of the ophthalmic composition is from 4.0 to 9.5.

[7] The ophthalmic composition according to any one of [1] to [6], wherein a content of water is 80 w/v % or more and less than 100 w/v % based on the total amount of the ophthalmic composition.

[8] The ophthalmic composition according to any one of [1] to [7], wherein a maximum value of light transmittance in a visible light region of wavelengths from 400 to 700 nm of the container formed from the resin containing a cyclic olefin is 50% or more.

[9] The ophthalmic composition according to any one of [1] to [8], wherein an amount of dropping per drop is from 1 to 99 μL.

[10] The ophthalmic composition according to any one of [1] to [9], wherein the number of uses is a small number or a single use.

[11] A method for imparting an effect of suppressing wetting to a resin containing a cyclic olefin to an ophthalmic composition, comprising blending (A2) a surface active component and (B2) a buffer into the ophthalmic composition.

[12] A method for imparting an effect of suppressing change in smell to an ophthalmic composition, comprising blending two or more kinds of (A2) surface active components, and (B2) a buffer into the ophthalmic composition contained in a container formed from a resin containing a cyclic olefin.

[Advantageous Effects of Second Aspect of Present Invention]

The ophthalmic composition of the second aspect of the present invention contains (A2) a surface active component and (B2) a buffer in combination and therefore produces an effect of increasing the dynamic contact angle to a resin containing a cyclic olefin (suppressing wetting) as compared with ophthalmic compositions containing the component (A2) alone. This produces an effect of suppressing liquid residues and improving liquid cutting, even in the case of being contained in a container in which a portion or the whole of a part coming into contact with the ophthalmic composition is formed from a resin containing a cyclic olefin. Furthermore, this can suppress reduction in the quality and reduction in the use performance of the ophthalmic composition.

The ophthalmic composition of the second aspect of the present invention, when further containing one or more kinds of components (A2) different from one kind of component (A2), produces an effect of suppressing change in smell, for example, by improving the odor, even in the case where the ophthalmic composition containing the one kind of component (A2), and the component (B2) is contained in a container formed from a resin containing a cyclic olefin.

[Description of Embodiments of Second Aspect of Present Invention]

Hereinafter, embodiments for executing the second aspect of the present invention will be explained in detail. However, the second aspect of the present invention is not limited to the following embodiments.

Unless indicated otherwise herein, the unit "%" of content means "w/v %" and is synonymous with "g/100 mL". Unless indicated otherwise herein, the abbreviation "POE" means polyoxyethylene, and the abbreviation "POP" means polyoxypropylene.

[1. Ophthalmic composition]

The ophthalmic composition according to the present embodiment contains (A2) a surface active component (also simply referred to as "component (A2)") and (B2) a buffer (also simply referred to as "component (B2)").

<Component (A2)>

The surface active component includes nonionic surfactants and polyalcohols and is not particularly limited as long as being a medically, pharmacologically (pharmaceutically) or physiologically acceptable one.

Specific examples of the nonionic surfactant include: POE sorbitan fatty acid esters such as monolaurate POE (20) sorbitan (polysorbate 20), monopalmitate POE (20) sorbitan (polysorbate 40), monostearate acid POE (20) sorbitan (polysorbate 60), tristearate POE (20) sorbitan (polysorbate 65), and monooleate POE (20) sorbitan (polysorbate 80); POE hydrogenated castor oils such as POE (5) hydrogenated castor oil (polyoxyethylene hydrogenated castor oil 5), POE (10) hydrogenated castor oil (polyoxyethylene hydrogenated castor oil 10), POE (20) hydrogenated castor oil (polyoxyethylene hydrogenated castor oil 20), POE (30) hydrogenated castor oil (polyoxyethylene hydrogenated castor oil 30), POE (40) hydrogenated castor oil (polyoxyethylene hydrogenated castor oil 40), POE (60) hydrogenated castor oil (polyoxyethylene hydrogenated castor oil 60), POE (80) hydrogenated castor oil (polyoxyethylene hydrogenated castor oil 80), and POE (100) hydrogenated castor oil (polyoxyethylene hydrogenated castor oil 100); POE castor oils such as POE (3) castor oil (polyoxyethylene castor oil 3), POE (10) castor oil (polyoxyethylene castor oil 10), POE (35) castor oil (polyoxyethylene castor oil 35), and POE (70) castor oil (polyoxyethylene castor oil 70); POE alkyl ethers such as POE (9) lauryl ether; POE-POP alkyl ethers such as POE (20) POP (4) cetyl ether; POE-POP glycols such as POE (20) POP (20) glycol (Pluronic L44), POE (42) POP (67) glycol (Poloxamer 403, Pluronic P123), POE (54) POP (39) glycol (Poloxamer 235, Pluronic P85), POE (120) POP (40) glycol (Pluronic F87), POE (160) POP (30) glycol (Poloxamer 188, Pluronic F68), POE (196) POP (67) glycol (Poloxamer 407, Pluronic F127), and POE (200) POP (70) glycol; and polyethylene glycol monostearates such as polyoxyl 10 stearate and polyoxyl 40 stearate. Note that the numbers in brackets for the compounds listed above represent addition mol numbers.

As the nonionic surfactant, POE sorbitan fatty acid esters, polyoxyethylene hydrogenated castor oils, polyoxyethylene castor oils, POE-POP glycols and polyethylene glycol monostearates are preferred, and polysorbate 80 and polyoxyethylene hydrogenated castor oil 60 are more preferred.

The nonionic surfactant can also employ a commercially available one. The nonionic surfactant may be used singly, or may be used in combination of two or more kinds thereof.

The polyalcohol is an alcohol having two or more hydroxy groups in the molecule, and a salt thereof.

Examples of the polyalcohol include: aliphatic polyalcohols (aliphatic alcohols having two or more hydroxy groups in the molecule) such as glycerin, propylene glycol, ethylene glycol, diethylene glycol, and polyethylene glycol (300, 400, 4000, 6000); sugar alcohols such as glucose, lactose, maltose, fructose, sorbitol, maltitol, mannitol, xylitol, and trehalose; and their salts.

As the polyalcohol, aliphatic polyalcohols and sugar alcohols are preferred, and glycerin, propylene glycol, polyethylene glycol (particularly, 400, 4000), sorbitol and mannitol are more preferred.

The polyalcohol can also employ a commercially available one. The polyalcohol may be used singly, or may be used in combination of two or more kinds thereof.

The surface active component may employ the nonionic surfactant and the polyalcohol alone or in combination.

In the case where the ophthalmic composition according to the present embodiment contains two or more kinds of surface active components, the combination of the surface active components is not particularly limited, and examples include two or more kinds of surface active components selected from the group consisting of a POE sorbitan fatty acid ester, a polyoxyethylene hydrogenated castor oil, a polyoxyethylene castor oil, a POE-POP glycol, a polyethylene glycol monostearate, an aliphatic polyalcohol and a sugar alcohol, preferably, a combination of a POE sorbitan fatty acid ester and a polyoxyethylene hydrogenated castor oil, a POE sorbitan fatty acid ester and a polyoxyethylene castor oil, a POE sorbitan fatty acid ester and a POE-POP glycol, a POE sorbitan fatty acid ester and a polyethylene glycol monostearate, a POE sorbitan fatty acid ester and an aliphatic polyalcohol, a POE sorbitan fatty acid ester and a sugar alcohol, a polyoxyethylene hydrogenated castor oil and a polyoxyethylene castor oil, a polyoxyethylene hydrogenated castor oil and a POE-POP glycol, a polyoxyethylene hydrogenated castor oil and a polyethylene glycol monostearate, a polyoxyethylene hydrogenated castor oil and an aliphatic polyalcohol, a polyoxyethylene hydrogenated castor oil and a sugar alcohol, a POE-POP glycol and a polyethylene glycol monostearate, a POE-POP glycol and an aliphatic polyalcohol, a POE-POP glycol and a sugar alcohol, a polyethylene glycol monostearate and a polyoxyethylene castor oil, a polyethylene glycol monostearate and an aliphatic polyalcohol, a polyethylene glycol monostearate and a sugar alcohol, a POE sorbitan fatty acid ester and a polyoxyethylene hydrogenated castor oil and a POE-POP glycol, a polyethylene glycol monostearate and a POE-POP glycol and an aliphatic polyalcohol, a polyethylene glycol monostearate and an aliphatic polyalcohol and a polyoxyethylene castor oil, or a polyethylene glycol monostearate and a POE-POP glycol and a polyoxyethylene castor oil.

The content of the component (A2) in the ophthalmic composition according to the present embodiment is not particularly limited and is appropriately set depending on the kind of the component (A2), the kind and content of an additional component to be blended, and the use and dosage form of the ophthalmic composition, etc. It is preferred for the content of the component (A2) that the total content of the component (A2) should be, for example, from 0.00001 to 10 w/v % based on the total amount of the ophthalmic composition, it is more preferred to be from 0.0001 to 9 w/v %, it is still more preferred to be from 0.001 to 7 w/v %, it is yet still more preferred to be from 0.001 to 5 w/v %, it is particularly preferred to be from 0.01 to 4 w/v %, it is more particularly preferred to be from 0.01 to 3 w/v %, it is still more particularly preferred to be from 0.01 to 2 w/v %, it is especially preferred to be from 0.01 to 1.5 w/v %, it is more especially preferred to be from 0.01 to 0.8 w/v %, it is still more especially preferred to be from 0.01 to 0.6 w/v %, and it is most preferred to be from 0.01 to 0.5 w/v %, in view of more significantly exerting the effect according to the second aspect of the present invention.

<Component (B2)>

The buffer includes inorganic buffers and organic buffers and is not particularly limited as long as being a medically, pharmacologically (pharmaceutically) or physiologically acceptable one.

The inorganic buffer is an inorganic acid-derived buffer. Examples of the inorganic buffer include boric acid buffers, phosphoric acid buffers, and carbonic acid buffers.

Examples of the boric acid buffer include boric acid and salts thereof (boric acid alkali metal salts, boric acid alkaline earth metal salts, etc.). Examples of the phosphoric acid buffer include phosphoric acid and salts thereof (phosphoric acid alkali metal salts, phosphoric acid alkaline earth metal salts, etc.). Examples of the carbonic acid buffer include carbonic acid and salts thereof (carbonic acid alkali metal salts, carbonic acid alkaline earth metal salts, etc.). As the boric acid buffer or the phosphoric acid buffer, a hydrate of borate salt or phosphoric salt may be used. More specific examples include, as the boric acid buffer, boric acid and salts thereof (sodium borate, potassium tetraborate, potassium metaborate, ammonium pentaborate, borax, etc.); as the phosphoric acid buffer, phosphoric acid and salts thereof (disodium hydrogenphosphate, sodium dihydrogen phosphate, potassium dihydrogen phosphate, trisodium monophosphate, tripotassium phosphate, calcium monohydrogen phosphate, monobasic calcium phosphate, etc.); and as the carbonic acid buffer, carbonic acid and salts thereof (sodium hydrogen carbonate, sodium carbonate, ammonium carbonate, potassium carbonate, calcium carbonate, potassium bicarbonate, magnesium carbonate, etc.).

The organic buffer is an organic acid- or organic base-derived buffer. Examples of the organic buffer include citric acid buffers, acetic acid buffers, Tris buffers, epsilon aminocaproic acid buffers, and AMPD buffers.

Examples of the citric acid buffer include citric acid and salts thereof (citric acid alkali metal salts, citric acid alkaline earth metal salts, etc.). Examples of the acetic acid buffer include acetic acid and salts thereof (acetic acid alkali metal salts, acetic acid alkaline earth metal salts, etc.). As the citric acid buffer or the acetic acid buffer, a hydrate of citrate salt or acetate salt may be used. More specific examples include: as the citric acid buffer, citric acid and salts thereof (sodium citrate, potassium citrate, calcium citrate, sodium dihydrogen citrate, disodium citrate, etc.); and as the acetic acid buffer, acetic acid and salts thereof (ammonium acetate, potassium acetate, calcium acetate, sodium acetate, etc.). Examples of the Tris buffer include trometamol and salts thereof (trometamol hydrochloride, etc.). Examples of the epsilon aminocaproic acid buffer include epsilon aminocaproic acid and salts thereof. Examples of the AMPD buffer include 2-amino-2-methyl-1,3-propanediol and salts thereof.

Among these buffers, boric acid buffers (e.g., a combination of boric acid and borax), phosphoric acid buffers (e.g., a combination of disodium hydrogenphosphate and sodium dihydrogen phosphate), and epsilon aminocaproic acid buffers (e.g., epsilon aminocaproic acid) are preferred.

The buffer can also employ a commercially available one. The buffer may be used singly, or may be used in combination of two or more kinds thereof.

The content of the component (B2) in the ophthalmic composition according to the present embodiment is not particularly limited and is appropriately set depending on the kind of the component (B2), the kind and content of an additional component to be blended, and the use and dosage form of the ophthalmic composition, etc. It is preferred for the content of the component (B2) that the total content of the component (B2) should be, for example, from 0.0001 to 9 w/v % based on the total amount of the ophthalmic composition, it is more preferred to be from 0.001 to 9 w/v %, it is still more preferred to be from 0.005 to 8 w/v %, it is yet still more preferred to be from 0.01 to 8 w/v %, and it is particularly preferred to be from 0.01 to 6 w/v %, in view of more significantly exerting the effect according to the second aspect of the present invention.

The content ratio of the component (B2) to the component (A2) in the ophthalmic composition according to the present embodiment is not particularly limited and is appropriately set depending on the kinds of the component (A2) and the component (B2), the kind and content of an additional component to be blended, and the use and dosage form of the ophthalmic composition, etc. It is preferred for the content ratio of the component (B2) to the component (A2) that the total content of the component (B2) should be, for example, from 0.001 to 8000 parts by weight based on 1 part by weight of the total content of the component (A2) contained in the ophthalmic composition according to the present embodiment, it is more preferred to be from 0.01 to 4000 parts by weight, it is still more preferred to be from 0.05 to 1000 parts by weight, it is yet still more preferred to be from 0.05 to 700 parts by weight, it is particularly preferred to be from 0.1 to 400 parts by weight, it is more particularly preferred to be from 0.1 to 300 parts by weight, it is still more particularly preferred to be from 0.1 to 200 parts by weight, it is especially preferred to be from 0.1 to 150 parts by weight, and it is most preferred to be from 0.1 to 100 parts by weight, in view of more significantly exerting the effect according to the second aspect of the present invention.

The ophthalmic composition according to the present embodiment may further contain one or more kinds of components selected from the group consisting of a vitamin, an antioxidant, an oil, a preservative, a polysaccharide, a vinyl compound, an amino acid, and terpenoid. These components are not particularly limited as long as being medically, pharmacologically (pharmaceutically) or physiologically acceptable ones.

The vitamin can be appropriately selected from known vitamins and used. Specific examples of the vitamin include: lipid soluble vitamins such as vitamin E (d-α-tocopherol, dl-α-tocopherol, β-tocopherol, γ-tocopherol, δ-tocopherol, etc.), vitamin A (retinal, retinol, retinoic acid, carotene, dehydroretinal, lycopene, etc.), and their derivatives, and their salts; and water soluble vitamins such as vitamin B1, vitamin B2 (flavin adenine dinucleotide), niacin (nicotinic acid and nicotinamide), pantothenic acid, panthenol, vitamin 136 (pyridoxine, pyridoxalisol, and pyridoxamine), biotin, folic acid, and vitamin B12 (cyanocobalamin, hydroxocobalamin, methylcobalamin, and adenosylcobalamin), and their salts. Specific examples of the salt of the vitamin include flavin adenine dinucleotide sodium, pyridoxine hydrochloride, calcium pantothenate, and sodium pantothenate. Specific examples of the derivative of the vitamin include tocopherol acetate, retinol acetate, and retinol palmitate.

As the vitamin, cyanocobalamin, flavin adenine dinucleotide, panthenol, pyridoxine, retinal, tocopherol and their derivatives, and their salts are preferred, and cyanocobalamin, flavin adenine dinucleotide sodium, panthenol, pyridoxine hydrochloride, retinol palmitate, and tocopherol acetate are more preferred.

The vitamin can also employ a commercially available one. The vitamin may be used singly, or may be used in combination of two or more kinds thereof.

The antioxidant is a compound that suppresses harmful reaction in which oxygen is involved, and a salt thereof. The antioxidant can be appropriately selected from known antioxidants and used.

Specific examples of the antioxidant include butylhydroxyanisole, dibutylhydroxytoluene, ascorbic acid and their salts.

As the antioxidant, butylhydroxyanisole, dibutylhydroxytoluene, and their salts are preferred, and butylhydroxyanisole and dibutylhydroxytoluene are more preferred.

The antioxidant can also employ a commercially available one. The antioxidant may be used singly, or may be used in combination of two or more kinds thereof.

The oil includes vegetable-derived vegetable oils, animal-derived animal oils, and natural or synthetic mineral oils. The oil can be appropriately selected from known oils and used.

Specific examples of the oil include: vegetable oils such as soybean oil, rice oil, rapeseed oil, cottonseed oil, sesame oil, safflower oil, almond oil, castor oil, olive oil, cacao oil, camellia oil, sunflower oil, palm oil, flax oil, perilla oil, shea oil, coconut oil, jojoba oil, grapeseed oil, and avocado oil; animal oils such as beeswax, lanoline (purified lanoline, etc.), orange roughy oil, squalane and horse oil; and mineral oils such as Vaseline (white Vaseline and yellow Vaseline, etc.) and liquid paraffine.

As the oil, sesame oil, castor oil, beeswax, lanoline, Vaseline and liquid paraffine are preferred.

The oil can also employ a commercially available one. The oil may be used singly, or may be used in combination of two or more kinds thereof.

The preservative is a compound having bactericidal activity or bacteriostatic activity, and a salt thereof The preservative can be appropriately selected from known preservatives or antibacterial agents and used.

Specific examples of the preservative include quaternary ammonium compounds (benzalkonium, benzethonium, chlorhexidine, alexidine, polyhexanide), alkylpolyaminoethylglycine, benzoic acid, chlorobutanol, sorbic acid, dehydroacetic acid, paraben (e.g., parahydroxybenzoic acid esters such as methyl parahydroxybenzoate, ethyl parahydroxybenzoate, propyl parahydroxybenzoate, and butyl parahydroxybenzoate), oxyquinoline, phenylethyl alcohol, benzyl alcohol, polyquaterniums, Glokill (manufactured by Rhodia, product name), zinc, sulfisoxazole, sulfadimidine and sulfamethoxazole, and their salts.

Specific examples of the salt of the preservative include benzalkonium chloride, benzethonium chloride, chlorhexidine gluconate, hydrochloric-acid alkyldiaminoethylglycine, sodium benzoate, potassium sorbate, sodium dehydroacetate, oxyquinoline sulfate, polyhexanide hydrochloride, polidronium chloride, zinc chloride, sulfisomidine sodium and sulfamethoxazole sodium.

As the preservative, quaternary ammonium compounds, alkylpolyaminoethylglycine, chlorobutanol, sorbic acid, paraben, phenylethyl alcohol and zinc are preferred, and benzalkonium chloride, polyhexamethylene biguanide, chlorhexidine gluconate, potassium sorbate, alexidine, polyhexanide hydrochloride, chlorobutanol, potassium sorbate, paraben, phenylethyl alcohol and zinc chloride are more preferred.

The preservative can also employ a commercially available one. The preservative may be used singly, or may be used in combination of two or more kinds thereof.

The polysaccharide includes dextran, acidic polysaccharides, cellulose-based polymer compounds and their salts. The polysaccharide can be appropriately selected from known polysaccharides and used.

Specific examples of the dextran include dextran 40 and dextran 70.

The acidic polysaccharide is a polysaccharide having an acidic group. Specific examples of the acidic polysaccharide include: acidic mucopolysaccharides such as hyaluronic acid, chondroitin sulfate, chitosan, heparin, heparan, alginic acid, and their derivatives (e.g., acetylated forms); and xanthan gum and gellan gum.

As the cellulose-based polymer compound, cellulose, and polymer compounds in which a hydroxyl group of cellulose is replaced with other functional groups can be used. Examples of the functional group that replaces the hydroxyl group of cellulose include a methoxy group, an ethoxy group, a hydroxymethoxy group, a hydroxyethoxy group, a hydroxypropoxy group, a carboxymethoxy group and a carboxyethoxy group. Specific examples of the cellulose-based polymer compound include methylcellulose, ethylcellulose, hydroxyethylcellulose, hydroxymethylcellulose, hydroxypropylcellulose, hydroxypropylmethylcellulose (hypromellose), carboxymethylcellulose, and carboxyethylcellulose.

As the polysaccharide, dextran, acidic polysaccharides, cellulose-based polymer compounds and their salts are preferred, dextran, acidic polysaccharides, hydroxyethylcellulose, hydroxypropylmethylcellulose, carboxymethylcellulose and their salts are more preferred, dextran, acidic mucopolysaccharides, xanthan gum, gellan gum, hydroxyethylcellulose, hydroxypropylmethylcellulose, carboxymethylcellulose and their salts are still more preferred, and dextran, chondroitin sulfate, hyaluronic acid, xanthan gum, gellan gum, hydroxyethylcellulose , hydroxypropylmethylcellulose, carboxymethylcellulose and their salts are particularly preferred.

The polysaccharide can also employ a commercially available one. The polysaccharide may be used singly, or may be used in combination of two or more kinds thereof.

The vinyl compound includes vinyl-based polymer compounds and their salts. The vinyl compound can be appropriately selected from known vinyl compounds and used.

Specific examples of the vinyl compound include vinyl alcohol-based polymers such as polyvinyl alcohol (completely or partially saponification products), vinylpyrrolidone-based polymers such as polyvinylpyrrolidone and carboxyvinyl polymers, and their salts.

As the vinyl compound, polyvinyl alcohol, polyvinylpyrrolidone, carboxyvinyl polymers and their salts are preferred, polyvinyl alcohol, polyvinylpyrrolidone, carboxyvinyl polymers and salts thereof are more preferred, polyvinyl alcohol, polyvinylpyrrolidone K17, polyvinylpyrrolidone K25, polyvinylpyrrolidone K30, polyvinylpyrrolidone K90, carboxyvinyl polymers and their salts are still more preferred, and polyvinyl alcohol, polyvinylpyrrolidone K30, polyvinylpyrrolidone K90, carboxyvinyl polymers and salts thereof are particularly preferred.

The vinyl compound can also employ a commercially available one. The vinyl compound may be used singly, or may be used in combination of two or more kinds thereof.

The amino acid is a compound having an amino group and a carboxyl group in the molecule, and a derivative thereof, and their salts. The amino acid can be appropriately selected from known amino acids and used.

Examples of the amino acid include amino acids and salts thereof, and amino acid derivatives and salts thereof Specific examples of the amino acid and the salt thereof include: monoamino monocarboxylic acids such as glycine, alanine, aminobutyric acid, and aminovaleric acid; monoamino dicarboxylic acids such as aspartic acid and glutamic acid; diamino monocarboxylic acids such as arginine and lysine; and their salts. Specific examples of the amino acid derivative and the salt thereof include amino acid derivatives such as aminoethylsulfonic acid (taurine), and salts thereof The amino acid may be any of a D form, an L form, and a DL form.

As the amino acid, monoamino dicarboxylic acids, amino acid derivatives, and their salts are preferred, glycine, aspartic acid, glutamic acid, arginine, taurine and their salts are more preferred, and glycine, potassium aspartate, sodium glutamate, arginine and taurine are still more preferred.

The amino acid can also employ a commercially available one. The amino acid may be used singly, or may be used in combination of two or more kinds thereof.

The terpenoid includes cyclic terpene and acyclic terpene.

The cyclic terpene is terpenoid having at least one ring structure in the molecule. Examples of the cyclic terpene include menthol, menton, camphor, borneol (also called "Dryobalanops aromatics resin"), cineole, carvone, anethole, eugenol, limonene, pinene, and their derivatives.

The acyclic terpene is terpenoid having no ring structure in the molecule. Examples of the acyclic terpene include geraniol, citronellol, linalool, linalyl acetate, and their derivatives.

In the second aspect of the present invention, essential oils containing the compounds described above may be used as the terpenoid. Examples of such essential oils include eucalyptus oil, bergamot oil, peppermint oil, cool mint oil, spearmint oil, mentha oil, fennel oil, cinnamon oil, and rose oil.

The terpenoid may be any of a d form, an l form and a dl form, and examples include l-menthol, d-menthol, dl-menthol, dl-camphor, d-camphor, dl-borneol, and d-borneol. However, there is a case where optical isomers are not present, depending on terpenoid, such as geraniol or cineole.

As the terpenoid, menthol, camphor, and borneol, and essential oils containing any of them are preferred, and menthol, camphor, and borneol are more preferred.

The terpenoid can also employ a commercially available one. The terpenoid may be used singly, or may be used in combination of two or more kinds thereof.

The pH of the ophthalmic composition according to the present embodiment is not particularly limited as long as being within the range that is medically, pharmacologically (pharmaceutically) or physiologically acceptable. The pH of the ophthalmic composition according to the present embodiment can be, for example, from 4.0 to 9.5, and it is preferred to be from 4.0 to 9.0, it is more preferred to be from 4.5 to 9.0, it is still more preferred to be from 4.5 to 8.5, and it is yet still more preferred to be from 5.0 to 8.5.

If necessary, the ophthalmic composition according to the present embodiment can be adjusted to an osmotic pressure ratio within the range that is acceptable to biological bodies. The appropriate osmotic pressure ratio may be appropriately set depending on the use, dosage form, use method, etc. of the ophthalmic composition, but can be, for example, from 0.4 to 5.0, and it is preferred to be from 0.6 to 3.0, it is more preferred to be from 0.8 to 2.2, and it is still more preferred to be from 0.8 to 2.0. The osmotic pressure ratio is a ratio of an osmotic pressure of a sample to 286 mOsm (osmotic pressure of a 0.9 w/v % sodium chloride aqueous solution) based on the Japanese Pharmacopoeia, 16th version, and the osmotic pressure is measured with reference to the osmometry determination described in the Japanese Pharmacopoeia (cryoscopic method). Note that the standard solution for osmotic pressure ratio measurement (0.9 w/v % sodium chloride aqueous solution) is prepared by drying sodium chloride (The Japanese Pharmacopoeia standard reagent) at 500 to 650° C. for 40 to 50 minutes, thereafter allowing it to cool in a desiccator (silica gel), accurately weighing 0.900 g thereof, and dissolving it in purified water to accurately make up a volume of 100 mL, or alternatively, a commercially available standard solution for osmotic pressure ratio measurement (0.9 w/v % sodium chloride aqueous solution) can be used.

The viscosity of the ophthalmic composition according to the present embodiment is not particularly limited as long as being within the range that is medically, pharmacologically (pharmaceutically) or physiologically acceptable. It is preferred for the viscosity of the ophthalmic composition according to the present embodiment that the viscosity at 20° C. measured with, for example, a rotational viscometer (RE550 viscometer, manufactured by Azuma Industry Co., Ltd., rotor; 1° 34'×R24) should be from 0.01 to 10000 mPa·s, it is more preferred to be from 0.05 to 8000 mPa·s, and it is still more preferred to be from 0.1 to 1000 mPa·s.

The ophthalmic composition according to the present embodiment may contain an appropriate amount of a combination of components selected from various pharmacologically active components and physiologically active components, in addition to the components described above, without impairing the effect of the second aspect of the present invention. The components are not particularly limited, and examples include active components in ophthalmic drugs described in Standards of Production and Sale of OTC Drugs 2012 (supervised by SOCIETY FOR REGULATORY SCIENCE OF MEDICAL PRODUCTS). Specific examples of the components used for ophthalmic drugs include components as follows:

antihistamine drugs: e.g., iproheptine, diphenhydramine hydrochloride, chlorpheniramine maleate, ketotifen fumarate, olopatadine hydrochloride, and levocabastine hydrochloride;

antiallergic drugs: e.g., disodium cromoglycate, tranilast, pemirolast potassium, and acitazanolast;

steroid drugs: e.g., fluticasone propionate, fluticasone furoate, mometasone furoate, beclometasone dipropionate, and flunisolide;

anti-inflammatory drugs: e.g., glycyrrhetinic acid, dipotassium glycyrrhizate, pranoprofen, methyl salicylate, glycol salicylate, allantoin, tranexamic acid, ε-aminocaproic acid, berberine, azulene sodium sulfonate, lysozyme chloride, zinc sulfate, zinc lactate, and licorice;

decongestants: tetrahydrozoline hydrochloride, tetrahydrozoline nitrate, naphazoline hydrochloride, naphazoline nitrate, epinephrine, epinephrine hydrochloride, ephedrine hydrochloride, phenylephrine hydrochloride, methylephedrine dl-hydrochloride, etc.;

ocular muscle regulating drugs: e.g., cholinesterase inhibitors having an active center similar to that of acetylcholine, specifically, neostigmine methylsulfate, tropicamide, helenien, atropine sulfate, etc.;

astringent drugs: e.g., hydrozincite, zinc lactate, and zinc sulfate;

local anesthetics: e.g., lidocaine and procaine; and others: rebamipide, etc.

In the ophthalmic composition according to the present embodiment, one or more kinds appropriately selected from various additives may be concomitantly used and contained in an appropriate amount in accordance with a conventional method depending on the use and dosage form thereof, without impairing the effect of the second aspect of the present invention. Examples of such additives include various additives described in Iyakuhin Tenkabutu Jiten 2007 (Encyclopedia of Pharmaceutical Excipients in English) (edited by Japan Pharmaceutical Excipients Council Japan). Examples of typical components include the following additives:

carriers: e.g., aqueous solvents such as water and hydrous ethanol;

chelating drugs: e.g., ethylenediamine diacetate (EDDA), ethylenediamine triacetic acid, ethylenediaminetetraacetate (EDTA), N-(2-hydroxyethyl)ethylenediamine-triacetic acid (HEDTA), and diethylenetriaminepentaacetic acid (DTPA);

bases: e.g., octyl dodecanol, titanium oxide, potassium bromide, and Plastibase;

pH adjusters: hydrochloric acid, acetic acid, sodium hydroxide, potassium hydroxide, calcium hydroxide, magnesium hydroxide, triethanolamine, diisopropanolamine, etc.;

stabilizers: sodium formaldehyde sulfoxylate (Rongalite), sodium bisulfate, sodium pyrosulfite, aluminum monostearate, glycerin monostearate, cyclodextrin, monoethanolamine, etc.;

anionic surfactants: polyoxyethylene alkyl ether phosphates, polyoxyethylene alkyl ether sulfates, alkylbenzenesulfonates, alkylsulfates, N-acyltaurine salts, etc.; and amphoteric surfactants: lauryl dimethylaminoacetic acid betaine, etc.

In the case where the ophthalmic composition according to the present embodiment contains water, it is preferred for the content of the water that the content of the water should be, for example, 80 w/v % or more and less than 100 w/v % based on the total amount of the ophthalmic composition, it is more preferred to be 85 w/v % or more and 99.5 w/v % or less, and it is still more preferred to be 90 w/v % or more and 99.2 w/v % or less, in view of more significantly exerting the effect according to the second aspect of the present invention.

The water used in the ophthalmic composition according to the present embodiment can be a medically, pharmacologically (pharmaceutically) or physiologically acceptable one. Examples of such water include distilled water, water, purified water, sterile purified water, water for injection, and distilled water for injection. These definitions are based on the Japanese Pharmacopoeia, 16th version.

The ophthalmic composition according to the present embodiment can be prepared by adding and mixing the desired amounts of the component (A2) and the component (B2), and other components, if necessary, so as to have the desired concentration. For example, it can be prepared by dissolving or dispersing these components in purified water to be adjusted to a predetermined pH and osmotic pressure, and sterilizing the resultant by filter sterilization or the like.

The ophthalmic composition according to the present embodiment can take various dosage forms depending on the intended use. Examples of the dosage form include liquid drugs, gel drugs, and semi solid drugs (ointments, etc.).

The ophthalmic composition according to the present embodiment can be used as, for example, eye drops (also referred to as ophthalmic solutions or ophthalmic drugs, and further, the eye drops include eye drops that can be instilled into eyes during use of contact lenses), artificial tears, eye washes (also referred to as collyriums or eye lotions, and further, the eye washes include eye washes that can wash eyes during use of contact lenses), and compositions for contact lenses [solutions for wearing a contact lens, compositions for contact lens care (contact lens disinfecting solutions, contact lens storage solutions, contact lens cleaning solutions, contact lens cleaning and storage solutions), etc.]. Note that the "contact lens" includes hard contact lenses and soft contact lenses (ionic and non-ionic lenses are both included and silicone hydro gel contact lenses and non-silicone hydro-gel contact lenses are both included).

In the case where the ophthalmic composition according to the present embodiment is eye drops, the dosage and administration thereof are not particularly limited as long as exerting effects and being a dosage and administration with less adverse reactions, and examples include a method of using by applying eye drop four times a day at 1 to 2 drops per dose, and a method of using by applying eye drop five to six times a day at 2 to 3 drops per dose, in the case of adults (15 years old or over) and children at age 7 or over.

<Container>

The ophthalmic composition according to the present embodiment is provided after being contained in a container in which a portion or the whole of a part coming into contact with the ophthalmic composition is formed from a resin containing a cyclic olefin (also simply referred to as "cyclic olefin-containing resin").

Examples of the cyclic olefin-containing resin include resins containing a cyclic olefin polymer (also simply referred to as "COP-containing resins"), and resins containing a cyclic olefin copolymer (also simply referred to as "COC-containing resins"). The cyclic olefin-containing resin is preferably a COC-containing resin in view of more significantly exerting the effect according to the second aspect of the present invention.

The COP-containing resin is not particularly limited as long as containing a polymer of one kind of cyclic olefin homopolymerized or a polymer of two or more kinds of cyclic olefins copolymerized, or a hydrogenation product thereof. The COP-containing resin preferably contains a ring-opened polymer of the cyclic olefin or a hydrogenation product thereof. Also, the COP-containing resin preferably contains a non-crystalline polymer.

The COC-containing resin is not particularly limited as long as containing a polymer of a cyclic olefin and an acyclic olefin copolymerized, or a hydrogenation product thereof.

Examples of the cyclic olefin include monocyclic or polycyclic cycloalkanes having a vinyl group, monocyclic or polycyclic cycloalkenes, and their derivatives. The cyclic olefin is preferably norbornene, tetracyclododecene, and their derivatives. Examples of the acyclic olefin include α-olefins such as ethylene, propylene, 1-butene, 1-pentene, and 1-hexene.

As the COP-containing resin, a resin containing a polymer of a cyclic olefin having a norbornene skeleton, or a hydrogenation product thereof is preferred in view of more significantly exerting the effect according to the second aspect of the present invention. As the COC-containing resin, a resin containing a polymer of norbornene and ethylene copolymerized is preferred in view of more significantly exerting the effect according to the second aspect of the present invention. Note that an additional monomer may be contained, in the polymer of a cyclic olefin and an acyclic olefin copolymerized, as a constituent of this polymer.

In the cyclic olefin-containing resin, for example, an additional polymer such as polyethylene (PE; high-density polyethylene (HDPE), low-density polyethylene (LDPE), linear low-density polyethylene (LLDPE)), polypropylene (PP), polycarbonate, a (meth)acrylic acid-based polymer, polystyrene (PS), polyethylene naphthalate (PEN), polyethylene terephthalate (PET), and polyarylate may be contained. It is preferred that the cyclic olefin-containing resin should further contain polyethylene (PE) and/or polypropylene (PP), in view of more significantly exerting the effect according to the second aspect of the present invention. In the case where the cyclic olefin-containing resin contains polyethylene (PE) and/or polypropylene (PP), it is preferred that the content of the polyethylene (PE) and/or the polypropylene (PP) should be from 0.001 to 50% by weight based on the total amount of the cyclic olefin-containing resin, it is more preferred to be from 0.01 to 45% by weight, it is still more preferred to be from 0.05 to 40% by weight, it is yet still more preferred to be from 0.1 to 35% by weight, it is particularly preferred to be from 0.5 to 30% by weight, it is more particularly preferred to be from 1 to 25% by weight, it is still more particularly preferred to be from 2 to 20% by weight, and it is most preferred to be from 5 to 15% by weight. In the case where the cyclic olefin-containing resin contains polyethylene (PE) and/or polypropylene (PP), it is preferred that the content of the polyethylene (PE) and/or the polypropylene (PP) should be 10% by weight or more based on the weight of the whole container, it is more preferred to be 15% by weight or more, it is still more preferred to be 20% by weight or more, it is yet still more preferred to be 25% by weight or more, it is particularly preferred to be 30% by weight or more, it is more particularly preferred to be 35% by weight or more, it is still more particularly preferred to be 38% by weight or more, and it is most preferred to be 40% by weight or more. In the case where the cyclic olefin-containing resin contains polyethylene (PE) and/or polypropylene (PP), it is preferred that the content of the polyethylene (PE) and/or the polypropylene (PP) should be 95% by weight or less based on the weight of the whole container, it is more preferred to be 90% by weight or less, it is still more preferred to be 85% by weight or less, it is yet still more preferred to be 80% by weight or less, it is particularly preferred to be 75% by weight or less, it is more particularly preferred to be 70% by weight or less, it is still more particularly preferred to be 65% by weight or less, and it is most preferred to be 60% by weight or less.

It is preferred for the cyclic olefin-containing resin according to the present embodiment that the content of the polymer of a cyclic olefin and an acyclic olefin copolymerized should be from 55 to 98% by weight based on the total amount of the cyclic olefin-containing resin, it is more preferred to be from 60 to 98% by weight, it is still more preferred to be from 65 to 98% by weight, it is yet still more preferred to be from 70 to 98% by weight, it is particularly preferred to be from 75 to 98% by weight, it is more particularly preferred to be from 80 to 98% by weight, it is still more particularly preferred to be from 85 to 98% by weight, and it is most preferred to be from 90 to 95% by weight. It is preferred for the cyclic olefin-containing resin according to the present embodiment that the content of the polymer of a cyclic olefin and an acyclic olefin copolymerized should be 10% by weight or more based on the weight of the whole container, it is more preferred to be 15% by weight or more, it is still more preferred to be 20% by weight or more, it is yet still more preferred to be 25% by weight or more, it is particularly preferred to be 30% by weight or more, it is more particularly preferred to be 35% by weight or more, it is still more particularly preferred to be 40% by weight or more, and it is most preferred to be 45% by weight or more. It is preferred for the cyclic olefin-containing resin according to the present embodiment that the content of the polymer of a cyclic olefin and an acyclic olefin copolymerized should be 95% by weight or less based on the weight of the whole container, it is more preferred to be 90% by weight or less, it is still more preferred to be 85% by weight or less, it is yet still more preferred to be 80% by weight or less, it is particularly preferred to be 75% by weight or less, it is more particularly preferred to be 70% by weight or less, it is still more particularly preferred to be 65% by weight or less, and it is most preferred to be 60% by weight or less.

The cyclic olefin-containing resin may contain additives such as a stabilizer and a modifier. The cyclic olefin copolymer-containing resin may be reinforced by containing a reinforcing agent such as glass fiber.

The cyclic olefin-containing resin can employ a commercially available one without particular limitations. Examples of the commercially available product of the COP-containing resin include ZEONEX(R) (manufactured by Zeon Corp.) and ZEONOR(R) (manufactured by Zeon Corp.). Examples of the commercially available product of the COC-containing resin include TOPAS(R) (manufactured by Polyplastics Co., Ltd.) and APEL(R) (manufactured by Mitsui Chemicals, Inc.).

The kind of the cyclic olefin-containing resin container can be a container generally used in the ophthalmic field and specifically, can be, for example, a container for eye drops, a container for eye washes, a container for containing solutions for wearing a contact lens, and a container for containing solutions for contact lens care (including a container for containing contact lens cleaning solutions, a container for containing contact lens storage solutions, a container for containing contact lens disinfecting solutions, a container for containing contact lens multi-purpose solutions, and the like). It is preferred that the kind of the cyclic olefin-containing resin container should be a container for eye drops, a container for containing solutions for wearing a contact lens, or a container for containing solutions for contact lens care. Note that the "contact lens" includes hard contact lenses and soft contact lenses (ionic and non-ionic lenses are both included and silicone hydro gel contact lenses and non-silicone hydro-gel contact lenses are both included). Examples of the part coming into contact with the ophthalmic composition in these containers include inside plugs, nozzles, and container inner surface (innermost layer in the case where the container has a structure consisting of a plurality of layers).

In the cyclic olefin-containing resin container according to the present embodiment, a portion or the whole of a part coming into contact with the ophthalmic composition is formed from the cyclic olefin-containing resin. For example, in the case where the cyclic olefin-containing resin container is a container having a nozzle, only the nozzle part may be formed from the cyclic olefin-containing resin, a containment part, etc. other than the nozzle may be formed from the cyclic olefin-containing resin, or the whole container may be formed from the cyclic olefin-containing resin.

Although a portion of the part coming into contact with the ophthalmic composition can be formed from the cyclic olefin-containing resin, it is preferred for the cyclic olefin-containing resin container that the whole of the part coming into contact with the ophthalmic composition should be formed from the cyclic olefin-containing resin, in view of still more significantly exerting the effect according to the second aspect of the present invention. In the case where a portion of the container is formed from the cyclic olefin-containing resin, the kind of a resin forming the other parts is not particularly limited, but one or more kids of polymers selected from the group consisting of, for example, polyethylene terephthalate (PET), polystyrene (PS), acrylonitrile-butadiene-styrene (ABS), polycarbonate, polyethylene (PE), polypropylene (PP), polymethyl methacrylate, an ethylene-vinyl acetate copolymer and an ethylene-vinyl alcohol copolymer may be contained as a constituent.

The shape and capacity of the cyclic olefin-containing resin container are not particularly limited and can be appropriately set depending on the use. The cyclic olefin-containing resin container may be a container in which the composition in an amount of multiple (e.g., 25 or more) uses is contained, may be a container in which the composition in an amount of a small number of (e.g., 2 or more and less than 25) uses is contained, or may be a container in which the composition in an amount of a single use is contained.

In the case where the cyclic olefin-containing resin container is a container that contains eye drops or a solution for wearing a contact lens, the capacity can be, for example, 0.01 mL or larger and 50 mL or smaller, and it is preferred to be 0.05 mL or larger and 40 mL or smaller, and it is more preferred to be 0.1 mL or larger and 25 mL or smaller. In the case where the cyclic olefin-containing resin container is a container that contains eye drops or a solution for wearing a contact lens and is a container in which the number of uses is a small number (e.g., 2 or larger and less than 25) or a single use, the capacity can be, for example, 0.01 mL or larger and 7 mL or smaller, and it is preferred to be 0.05 mL or larger and 6 mL or smaller, it is more preferred to be 0.1 mL or larger and 5 mL or smaller, it is still more preferred to be 0.1 mL or larger and 3 mL or smaller, it is yet still more preferred to be 0.2 mL or larger and 2 mL or smaller, and it is particularly preferred to be 0.2 mL or larger and 1 mL or smaller. In the case where the cyclic olefin-containing resin container is a container that contains an eye wash or a solution for contact lens care, the capacity can be, for example, 40 mL or larger and 600 mL or smaller, and it is preferred to be 45 mL or larger and 550 mL or smaller. In the case where the cyclic olefin-containing resin container is a container that contains an eye wash or a solution for contact lens care and is a container in which the number of uses is a small number (e.g., 2 or larger and less than 25) or a single use, the capacity can be, for example, 10 mL or larger and 150 mL or smaller, and it is preferred to be 10 mL or larger and 130 mL or smaller.

The cyclic olefin-containing resin container may be a container with a composition containment part and a bung hole integrally formed, or may be a container having a nozzle. In the case where the cyclic olefin-containing resin container is a container that contains eye drops or a solution for wearing a contact lens and is a container in which the number of uses is a small number (e.g., 2 or larger and less than 25) or a single use; and the capacity is 0.1 mL or larger and 3 mL or smaller, it is preferred to be a container with a composition containment part and a bung hole integrally formed.

It is preferred that the cyclic olefin containing resin container should be a container having transparency in view of being able to macroscopically observe the confirmation of foreign substances, the confirmation of a residual volume, etc. The cyclic olefin-containing resin container may be colorless or may be colored as long as having transparency. The cyclic olefin-containing resin container can be a container having transparency that secures internal visibility to the extent that the inside is macroscopically observable, and the entire surface of the container does not necessarily have to have uniform transparency as long as the internal visibility described above is secured in a part of the container. As the transparency, for example, the maximum value of light transmittance (hereinafter, also referred to as "maximum light transmittance") in a visible light region of wavelengths from 400 to 700 nm of the cyclic olefin-containing resin container can be 50% or more, and it is preferred to be 60% or more, it is more preferred to be 70% or more, and it is still more preferred to be 80% or more. The maximum light transmittance can be determined from each light transmittance obtained by using, for example, a microplate reader and measuring light transmittance at 10-nm intervals between wavelengths of 400 and 700 nm. Note that in the case where the inside plug part is tinkled from a cyclic olefin-containing resin and in the case where the maximum light transmittance cannot be measured due to its shape, size, etc., the maximum light transmittance can also be determined as to a commercially available cyclic olefin-containing resin similar thereto in transparency by macroscopic observation and regarded as the transparency of the inside plug. Alternatively, the transparency of the inside plug can also be confirmed by carrying out the Foreign Insoluble Matter Test specified by the Japanese Pharmacopoeia.

The thickness of the cyclic olefin-containing resin container can be from 0.01 to 3.0 mm, and it is preferred to be from 0.05 to 2.0 mm, it is more preferred to be from 0.1 to 1.5 mm, it is still more preferred to be from 0.1 to 1.2 mm, it is yet still more preferred to be from 0.1 to 1.0 mm, it is particularly preferred to be from 0.1 to 0.8 mm, it is more particularly preferred to be from 0.1 to 0.6 mm, it is still more particularly preferred to be from 0.1 to 0.5 mm, and it is most preferred to be from 0.1 to 0.4 mm, in view of more significantly exerting an effect of improving liquid cutting.

It is preferred that the amount of dropping per drop of the ophthalmic composition according to the present embodiment should be designed so as to be from 1 to 99 µL, it is more preferred to be from 1 to 79 µL, it is still more preferred to be from 7 to 79 µL, and it is yet still more preferred to be from 13 to 79 µL, in view of still more significantly exerting the effect according to the second aspect of the present invention.

For the ophthalmic composition according to the present embodiment, the capacity for the ophthalmic composition, the amount of dropping per drop, the size of the container, the shape of the inside plug, the shape of the bung hole, etc. can be appropriately designed such that the number of uses is a small number or a single use.

The ophthalmic composition according to the present embodiment may also be provided as an ophthalmic composition contained in a cyclic olefin-containing resin container. The second aspect of the present invention can also be interpreted as an ophthalmic product (eye drops, an eye wash, or a contact lens-related product, etc.) in which the ophthalmic composition of the second aspect of the present invention is contained in the cyclic olefin-containing resin container.

[2. Suppression of Wetting to Cyclic Olefin-Containing Resin]

The ophthalmic composition according to the present embodiment exhibits suppressed wetting to a resin containing a cyclic olefin. Thus, as one embodiment of the second aspect of the present invention, provided is a method for imparting an effect of suppressing wetting to a resin containing a cyclic olefin to an ophthalmic composition, comprising blending (A2) a surface active component and (B2) a buffer into the ophthalmic composition. As another embodiment of the second aspect of the present invention, provided is a method for suppressing wetting of an ophthalmic composition to a resin containing a cyclic olefin, comprising blending (A2) a surface active component and (B2) a buffer into the ophthalmic composition.

Note that, in the present embodiment, the kinds and contents, etc. of the component (A2) and the component (B2), the kinds and contents, etc. of other components, and the dosage form and use, etc. of the ophthalmic composition are as explained in [1. Ophthalmic Composition].

[3. Suppression of Change in Smell]

Provided that the ophthalmic composition contained in a container formed from a resin containing a cyclic olefin according to the present embodiment contains two or more kinds of (A2) surface active components, change in smell is suppressed, for example, by suppressing the odor. Thus, as one embodiment of the second aspect of the present invention, provided is a method for imparting an effect of suppressing change in smell to an ophthalmic composition, comprising blending two or more kinds of (A2) surface active components and (B2) a buffer into the ophthalmic composition contained in a container fanned from a resin containing a cyclic olefin. As another embodiment of the second aspect of the present invention, provided is a method for suppressing change in smell of an ophthalmic composition, comprising blending two or more kinds of (A2) surface active components and (B2) a buffer into the ophthalmic composition contained in a container formed from a resin containing a cyclic olefin.

Note that, in the present embodiment, the kinds and contents, etc. of the component (A2) and the component (B2), the kinds and contents, etc. of other components, and the dosage form and use, etc. of the ophthalmic composition are as explained in [1. Ophthalmic Composition].

As one embodiment of the second aspect of the present invention, provided is a method for using an ophthalmic composition, the ophthalmic composition containing (A2) a surface active component and (B2) a buffer and contained in a container foiled from a resin containing a cyclic olefin, wherein the number of uses is a small number or a single use. Note that, while suppression of liquid residues and improvement in liquid cutting are required for exerting the desired pharmacological effect, particularly, in a small number of uses or a single use, the ophthalmic composition containing (A2) a surface active component and (B2) a buffer according to the present embodiment is contained in a container formed from a resin containing a cyclic olefin and thereby produces an effect of suppressing liquid residues and improving liquid cutting.

[Examples of Second Aspect of Present Invention]

Hereinafter, the second aspect of the present invention will be specifically explained based on Test Examples, however the second aspect of the present invention is not limited thereto.

[Testing Method: Method for Measuring Dynamic Contact Angle (Angle of Advance)]

The contact angle meter DM-501 (manufactured by Kyowa Interface Science Co., Ltd.) was used to measure the dynamic contact angle (angle of advance) of each test solution in accordance with the measurement procedure of the expansion and contraction method of the contact angle meter. The dynamic contact angle (angle of advance) is a contact angle when the interface between solid and liquid moves.

Specifically, each sheet-shaped container material (low-density polyethylene (LDPE), linear low-density polyethylene (LLDPE), polypropylene (PP), cyclic olefin copolymer (COC; TOPAS8007 (manufactured by Polyplastics Co., Ltd.)), or a resin containing two or more kinds thereof) of 0.2 mm in thickness was placed on the stage of the contact angle meter, and a test solution was placed in a dispenser. 1 µL of droplets of the test solution at room temperature was dropped onto each container material to form a hemispherical shape. Then, to the top of the hemispherical shape, the head of the liquid discharge unit of the dispenser was quickly attached. In the state, the test solution was continuously discharged at a discharge velocity of 6 µL/sec, and the shapes of the droplets were photographed from the side surface 15 times per 0.1 sec. In order to satisfy the same measurement conditions, test solutions to be paired in calculating the change rate of the dynamic contact angle employed each identical container material and were continuously measured under identical temperature conditions (at room temperature).

Then, the right and left contact angles were determined for each image using the analysis software FAMAS of the contact angle meter. Here, among angles foimed by the tangent line drawn from the contact point P of the surface of each sheet-shaped container material of 0.2 mm in thickness, the test solution, and the air to the test solution and the tangent line drawn on the surface of each sheet-shaped container material, the contact angle means an angle at the side including the test solution. The two contact points P are present at the right and left sides for each of the droplets. As the droplets were expanded according to the discharge of the test solution, the contact angles changed and subsequently exhibited a behavior of becoming almost constant. Accordingly, the average of the right and left contact angles was calculated for each image; the averages were arranged in the order of photographing the images; five consecutive averages were selected; and the first average (average of the right and left contact angles in the image taken earliest among the five averages) when the standard deviation of the five averages firstly reached 2.0° or less was defined as the measurement value of the dynamic contact angle in this measurement. Note that regarding all the test solutions, after the standard deviation firstly reached 2.0° or less, no standard deviation larger than 2.0° was observed. In the case where the contact angle did not change in the course where the droplets were expanded, the measurement value of the dynamic contact angle was also obtained in accordance with the standard described above.

The procedure described above was repetitively performed three times as to each test solution, and the average of 3 measurement values obtained was regarded as the dynamic contact angle of the test solution. The standard deviation of the 3 measurement values was 2.0° or less in all the test solutions.

[Test Example 1: Dynamic Contact Angle (Angle of Advance) Evaluation (1)]

Each prescription shown in Table 2-1 was prepared by a conventional method and used as a test solution. The unit of content of each component in Table 2-1 is w/v %. Note that the component (A2) solution in each test is a prescription containing the component (A2) shown in Table 2-1 at the content shown in Table 2-1 (the balance was purified water).

The dynamic contact angle of each test solution was determined (average of 3 measurement values) in accordance with the procedure shown in the testing method described above. The container material used was a cyclic olefin copolymer (COC; TOPAS8007 (manufactured by Polyplastics Co., Ltd.)) or low-density polyethylene (LDPE). Subsequently, the change rate of the dynamic contact angle of the component (A2) solution contacted with a cyclic olefin copolymer (COC) with respect to the component (A2) solution contacted with low-density polyethylene (LDPE) was calculated according to [Expression 1] given below. The calculated results are shown in Table 2-1.

Change rate of the dynamic contact angle (%)={
(dynamic contact angle of the component (A2)
solution to COC/dynamic contact angle of the
component (A2) solution to LDPE)−1}×100  [Expression 1]

TABLE 2-1

| Test Example | Component (A2) Component name | Content | Change rate of dynamic contact angle (%) |
|---|---|---|---|
| 1-1 | Polysorbate 80 | 0.08 | −2.6% |
| 1-2 | Polyoxyethylene hydrogenated castor oil 60 | 0.08 | −2.8% |
| 1-3 | Polyoxyethylene castor oil 35 | 0.08 | −7.7% |
| 1-4 | Polyoxyethylene castor oil 10 | 0.016 | −9.1% |
| 1-5 | Polyoxyl 40 stearate | 0.08 | −5.5% |
| 1-6 | POE(200)POP(20) glycol | 0.1 | −11.7% |
| 1-7 | POE(196)POP(67) glycol | 0.1 | −8.0% |
| 1-8 | POE(160)POP(30) glycol | 0.1 | −8.6% |
| 1-9 | Propylene glycol | 0.1 | −4.8% |
| 1-10 | Polyethylene glycol 4000 | 0.1 | −4.4% |
| 1-11 | Glycerin | 0.1 | −2.3% |
| 1-12 | D-Mannitol | 0.1 | −3.8% |
| 1-13 | Sorbitol | 0.1 | −8.9% |
| 1-14 | Xylitol | 0.1 | −6.9% |

As shown in Table 2-1, when a cyclic olefin copolymer (COC) is used as a container material, the dynamic contact angle of the test solution containing the component (A2) is smaller as compared with the case of using low-density polyethylene (LDPE); thus there is a problem that wetting occurs easily to a cyclic olefin copolymer (COC).

[Test Example 2: Dynamic Contact Angle (Angle of Advance) Evaluation (2)]

The test solution of each Test Example shown in Tables 2-2 to 2-7 was prepared by a conventional method. The unit of each component in Tables 2-2 to 2-7 is w/v %. Note that the corresponding prescribed solution is a prescription in which components other than the component (A2) were excluded from the prescription of each test solution, and the pH was adjusted with appropriate amounts of hydrochloric acid and sodium hydroxide (the balance was purified water). The container material was a cyclic olefin copolymer (COC; TOPAS8007 (manufactured by Polyplastics Co., Ltd.)) or a container material containing 90 w/w % of COC and 10 w/w % of low-density polyethylene (LDPE).

The dynamic contact angle of each test solution was determined (average of 3 measurement values) in accordance with the procedure shown in the testing method described above. Subsequently, the change rate of the dynamic contact angle of the test solution of Test Example with respect to the corresponding prescribed solution was calculated according to [Expression 2] given below. The calculated results are shown in Tables 2-2 to 2-7.

Change rate of the dynamic contact angle (%)=
{(dynamic contact angle of the test solution of
Test Example/dynamic contact angle of the corresponding prescribed solution to COC)−1}×
100  [Expression 2]

TABLE 2-2

| | Test Example 2-1 | Test Example 2-2 | Test Example 2-3 | Test Example 2-4 | Test Example 2-5 | Test Example 2-6 | Test Example 2-7 | Test Example 2-8 | Test Example 2-9 | Test Example 2-10 | Test Example 2-11 | Test Example 2-12 |
|---|---|---|---|---|---|---|---|---|---|---|---|---|
| (A2) Polysorbate 80 | 0.08 | 0.08 | 0.08 | 0.08 | 0.08 | 0.08 | — | — | — | — | — | — |
| (A2) Polyoxyethylene hydrogenated castor oil 60 | — | — | — | — | — | — | 0.08 | 0.08 | 0.08 | 0.08 | 0.08 | 0.08 |
| (B2) Boric acid | 1 | — | — | — | — | — | 1.3 | — | — | — | — | — |
| (B2) Borax | 0.2 | — | — | — | — | — | 0.2 | — | — | — | — | — |
| (B2) Sodium hydrogen phosphate | — | 1.2 | — | — | — | — | — | 1 | — | — | — | — |
| (B2) Sodium dihydrogen phosphate | — | 0.1 | — | — | — | — | — | 0.22 | — | — | — | — |
| (B2) Trometamol | — | — | 0.2 | — | — | — | — | — | 0.05 | — | — | — |

TABLE 2-2-continued

|  | Test Example 2-1 | Test Example 2-2 | Test Example 2-3 | Test Example 2-4 | Test Example 2-5 | Test Example 2-6 | Test Example 2-7 | Test Example 2-8 | Test Example 2-9 | Test Example 2-10 | Test Example 2-11 | Test Example 2-12 |
|---|---|---|---|---|---|---|---|---|---|---|---|---|
| (B2) Citric acid | — | — | — | 0.01 | — | — | — | — | — | 0.08 | — | — |
| (B2) Sodium citrate | — | — | — | 0.5 | — | — | — | — | — | 1.1 | — | — |
| (B2) Epsilon aminocaproic acid | — | — | — | — | 3 | — | — | — | — | — | 1.5 | — |
| (B2) 2-Amino-2-methyl-1,3-propanediol | — | — | — | — | — | 0.7 | — | — | — | — | — | 0.5 |
| Hydrochloric acid | q.s. | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance | Balance |
| pH | 7.5 | 7.5 | 7.5 | 7.5 | 7.5 | 7.5 | 6.5 | 6.5 | 6.5 | 6.5 | 6.5 | 6.5 |
| Change rate of dynamic contact angle (container material: COC) | 3.1% | 2.7% | 2.6% | 5.0% | 5.0% | 4.2% | 4.4% | 5.8% | 3.7% | 2.9% | 3.9% | 4.0% |
| Change rate of dynamic contact angle (container material: COC and LDPE) | 10.3% | 9.4% | 8.6% | 7.6% | 8.7% | 8.5% | 7.8% | 8.5% | 4.5% | 6.1% | 10.5% | 6.4% |

TABLE 2-3

|  | Test Example 2-13 | Test Example 2-14 | Test Example 2-15 | Test Example 2-16 | Test Example 2-17 | Test Example 2-18 | Test Example 2-19 | Test Example 2-20 | Test Example 2-21 | Test Example 2-22 | Test Example 2-23 |
|---|---|---|---|---|---|---|---|---|---|---|---|
| (A2) Polyoxyethylene castor oil 35 | 0.08 | 0.08 | — | — | — | — | — | — | — | — | — |
| (A2) Polyoxyethylene castor oil 10 | — | — | 0.016 | 0.016 | 0.016 | — | — | — | — | — | — |
| (A2) Polyoxyethylene hydrogenated castor oil 60 | — | — | 0.08 | 0.08 | 0.08 | — | — | — | — | — | — |
| (A2) Polyoxyl 40 stearate | — | — | — | — | — | 0.08 | 0.08 | 0.08 | 0.08 | 0.08 | 0.08 |
| (B2) Boric acid | 1 | — | 1.5 | — | — | 1.2 | — | — | — | — | — |
| (B2) Borax | 0.2 | — | 0.35 | — | — | 0.2 | — | — | — | — | — |
| (B2) Sodium hydrogen phosphate | — | — | — | — | — | — | 1 | — | — | — | — |
| (B2) Sodium dihydrogen phosphate | — | — | — | — | — | — | 0.25 | — | — | — | — |
| (B2) Trometamol | — | 0.2 | — | 0.01 | — | — | — | 0.1 | — | — | — |
| (B2) Citric acid | — | — | — | — | — | — | — | — | 0.02 | — | — |
| (B2) Sodium citrate | — | — | — | — | — | — | — | — | 0.5 | — | — |
| (B2) Epsilon aminocaproic acid | — | — | — | — | 0.5 | — | — | — | — | 3.5 | — |
| (B2) 2-Amino-2-methyl-1,3-propanediol | — | — | — | — | — | — | — | — | — | — | 0.1 |
| Hydrochloric acid | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance |
| pH | 7.5 | 7.5 | 5.2 | 5.2 | 5.2 | 7.0 | 7.0 | 7.0 | 7.0 | 7.0 | 7.0 |
| Change rate of dynamic contact angle (container material: COC) | 10.1% | 6.8% | 9.0% | 7.3% | 7.8% | 3.7% | 3.5% | 3.8% | 3.0% | 3.1% | 5.1% |
| Change rate of dynamic contact angle (container material: COC and LDPE) | 16.6% | 14.6% | 17.7% | 17.4% | 14.2% | 8.2% | 8.0% | 13.1% | 9.2% | 5.9% | 10.6% |

TABLE 2-4

|  | Test Example 2-24 | Test Example 2-25 | Test Example 2-26 | Test Example 2-27 | Test Example 2-28 | Test Example 2-29 | Test Example 2-30 | Test Example 2-31 | Test Example 2-32 | Test Example 2-33 | Test Example 2-34 | Test Example 2-35 |
|---|---|---|---|---|---|---|---|---|---|---|---|---|
| (A2) POE(200)POP(20) glycol | 0.1 | 0.1 | 0.1 | — | — | — | — | — | — | — | — | — |
| (A2) POE(196)POP(67) glycol | — | — | — | 0.1 | 0.1 | 0.1 | 0.1 | 0.1 | 0.1 | — | — | — |
| (A2) POE(160)POP(30) glycol | — | — | — | — | — | — | — | — | — | 0.1 | 0.1 | 0.1 |
| (B2) Boric acid | 1.2 | — | — | 1.3 | — | — | — | — | — | 1.5 | — | — |
| (B2) Borax | 0.2 | — | — | 0.2 | — | — | — | — | — | 0.35 | — | — |
| (B2) Sodium hydrogen phosphate | — | — | — | — | 1 | — | — | — | — | — | — | — |
| (B2) Sodium dihydrogen phosphate | — | — | — | — | 0.22 | — | — | — | — | — | — | — |
| (B2) Trometamol | — | 0.1 | — | — | — | 0.05 | — | — | — | — | 0.01 | — |
| (B2) Citric acid | — | — | — | — | — | — | 0.08 | — | — | — | — | — |
| (B2) Sodium citrate | — | — | — | — | — | — | 1.1 | — | — | — | — | — |
| (B2) Epsilon aminocaproic acid | — | — | — | — | — | — | — | 1.5 | — | — | — | 0.5 |
| (B2) 2-Amino-2-methyl-1,3-propanediol | — | — | 0.1 | — | — | — | — | — | 0.5 | — | — | — |
| Hydrochloric acid | q.s. | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance | Balance |
| pH | 7.0 | 7.0 | 7.0 | 6.5 | 6.5 | 6.5 | 6.5 | 6.5 | 6.5 | 5.2 | 5.2 | 5.2 |

TABLE 2-4-continued

|  | Test Example 2-24 | Test Example 2-25 | Test Example 2-26 | Test Example 2-27 | Test Example 2-28 | Test Example 2-29 | Test Example 2-30 | Test Example 2-31 | Test Example 2-32 | Test Example 2-33 | Test Example 2-34 | Test Example 2-35 |
|---|---|---|---|---|---|---|---|---|---|---|---|---|
| Change rate of dynamic contact angle (container material: COC) | 4.3% | 5.2% | 5.2% | 5.0% | 4.6% | 4.0% | 2.6% | 2.2% | 4.6% | 3.1% | 3.1% | 2.9% |
| Change rate of dynamic contact angle (container material: COC and LDPE) | 11.3% | 12.2% | 12.9% | 7.5% | 7.2% | 9.1% | 7.1% | 7.9% | 6.6% | 13.3% | 8.7% | 8.9% |

TABLE 2-5

|  | Test Example 2-36 | Test Example 2-37 | Test Example 2-38 | Test Example 2-39 | Test Example 2-40 | Test Example 2-41 | Test Example 2-42 | Test Example 2-43 | Test Example 2-44 | Test Example 2-45 | Test Example 2-46 | Test Example 2-47 |
|---|---|---|---|---|---|---|---|---|---|---|---|---|
| (A2) Propylene glycol | 0.1 | 0.1 | 0.1 | 0.1 | 0.1 | 0.1 | — | — | — | — | — | — |
| (A2) Polyethylene glycol 4000 | — | — | — | — | — | — | 0.1 | 0.1 | 0.1 | 0.1 | 0.1 | 0.1 |
| (B2) Boric acid | 1.8 | — | — | — | — | — | 1.8 | — | — | — | — | — |
| (B2) Borax | 0.4 | — | — | — | — | — | 0.4 | — | — | — | — | — |
| (B2) Sodium hydrogen phosphate | — | 0.8 | — | — | — | — | — | 0.8 | — | — | — | — |
| (B2) Sodium dihydrogen phosphate | — | 0.3 | — | — | — | — | — | 0.3 | — | — | — | — |
| (B2) Trometamol | — | — | 1.5 | — | — | — | — | — | 1.5 | — | — | — |
| (B2) Citric acid | — | — | — | 0.02 | — | — | — | — | — | 0.02 | — | — |
| (B2) Sodium citrate | — | — | — | 0.6 | — | — | — | — | — | 0.6 | — | — |
| (B2) Epsilon aminocaproic acid | — | — | — | — | 5 | — | — | — | — | — | 5 | — |
| (B2) 2-Amino-2-methyl-1,3-propanediol | — | — | — | — | — | 0.05 | — | — | — | — | — | 0.05 |
| Hydrochloric acid | q.s. | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance | Balance |
| pH | 8.0 | 8.0 | 8.0 | 8.0 | 8.0 | 8.0 | 8.0 | 8.0 | 8.0 | 8.0 | 8.0 | 8.0 |
| Change rate of dynamic contact angle (container material: COC) | 3.0% | 2.5% | 6.5% | 5.1% | 3.6% | 3.6% | 4.1% | 3.0% | 5.2% | 3.3% | 3.0% | 3.3% |
| Change rate of dynamic contact angle (container material: COC and LDPE) | 10.6% | 11.0% | 9.6% | 7.7% | 8.5% | 8.5% | 9.0% | 8.1% | 8.5% | 5.9% | 6.5% | 8.6% |

TABLE 2-6

|  | Test Example 2-48 | Test Example 2-49 | Test Example 2-50 | Test Example 2-51 | Test Example 2-52 | Test Example 2-53 | Test Example 2-54 | Test Example 2-55 | Test Example 2-56 |
|---|---|---|---|---|---|---|---|---|---|
| (A2) Glycerin | 0.1 | 0.1 | 0.1 | — | — | — | — | — | — |
| (A2) D-mannitol | — | — | — | 0.1 | 0.1 | 0.1 | 0.1 | 0.1 | 0.1 |
| (B2) Boric acid | 0.5 | — | — | 0.8 | — | — | — | — | — |
| (B2) Borax | 0.008 | — | — | 0.12 | — | — | — | — | — |
| (B2) Sodium hydrogen phosphate | — | 0.5 | — | — | 0.4 | — | — | — | — |
| (B2) Sodium dihydrogen phosphate | — | 0.08 | — | — | 0.02 | — | — | — | — |
| (B2) Trometamol | — | — | 0.01 | — | — | 0.3 | — | — | — |
| (B2) Citric acid | — | — | — | — | — | — | 0.005 | — | — |
| (B2) Sodium citrate | — | — | — | — | — | — | 0.45 | — | — |
| (B2) Epsilon aminocaproic acid | — | — | — | — | — | — | — | 4 | — |
| (B2) 2-Amino-2-methyl-1,3-propanediol | — | — | — | — | — | — | — | — | 0.01 |
| Hydrochloric acid | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. |
| Purified water | Balance | Balance | Balance | Balance | Balance | Balance | Balance | Balance | Balance |
| pH | 5.0 | 5.0 | 5.0 | 7.2 | 7.2 | 7.2 | 7.2 | 7.2 | 7.2 |
| Change rate of dynamic contact angle (container material: COC) | 5.8% | 5.7% | 4.6% | 3.9% | 4.6% | 3.1% | 2.9% | 3.6% | 3.4% |
| Change rate of dynamic contact angle (container material: COC and LDPE) | 10.3% | 10.0% | 7.9% | 7.1% | 6.4% | 6.1% | 5.6% | 6.0% | 6.3% |

TABLE 2-7

|  | Test Example 2-57 | Test Example 2-58 | Test Example 2-59 | Test Example 2-60 | Test Example 2-61 | Test Example 2-62 | Test Example 2-63 | Test Example 2-64 |
|---|---|---|---|---|---|---|---|---|
| (A2) D-Sorbitol | 0.1 | 0.1 | 0.1 | 0.1 | 0.1 | 0.1 | — | — |
| (A2) Xylitol | — | — | — | — | — | — | 0.1 | 0.1 |
| (B2) Boric acid | 0.8 | — | — | — | — | — | 0.5 | — |
| (B2) Borax | 0.12 | — | — | — | — | — | 0.008 | — |
| (B2) Sodium hydrogen phosphate | — | 0.4 | — | — | — | — | — | — |
| (B2) Sodium dihydrogen phosphate | — | 0.02 | — | — | — | — | — | — |
| (B2) Trometamol | — | — | 0.3 | — | — | — | — | 0.01 |
| (B2) Citric acid | — | — | — | 0.02 | — | — | — | — |
| (B2) Sodium citrate | — | — | — | 0.45 | — | — | — | — |
| (B2) Epsilon aminocaproic acid | — | — | — | — | 4 | — | — | — |
| (B2) 2-Amino-2-methyl-1,3-propanediol | — | — | — | — | — | 0.01 | — | — |
| Hydrochloric acid | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. |
| Purified water | Balance | Balance | Balance | Balance | Balance | Balance | Balance | Balance |
| pH | 7.2 | 7.2 | 7.2 | 7.2 | 7.2 | 7.2 | 5.0 | 5.0 |
| Change rate of dynamic contact angle (container material: COC) | 5.4% | 3.3% | 3.4% | 4.1% | 3.0% | 3.7% | 4.2% | 3.5% |
| Change rate of dynamic contact angle (container material: COC and LDPE) | 9.4% | 8.5% | 10.3% | 9.0% | 8.8% | 8.2% | 10.3% | 8.6% |

As shown in Tables 2-2 to 2-7, when a cyclic olefin copolymer (COC) is used as a container material, the dynamic contact angle of the test solution containing the component (A2) and the component (B2) is larger than the dynamic contact angle of the test solution containing no component (B2), and wetting to the container can be suppressed (Test Examples 2-1 to 2-64). When a resin further containing low-density polyethylene (LDPE) in addition to the cyclic olefin copolymer (COC) is used as a container material, the dynamic contact angle of the test solution containing the component (A2) and the component (B2) is larger than the dynamic contact angle of the test solution containing no component (B2), and wetting to the container can be suppressed (Test Examples 2-1 to 2-64).

[Test Example 3: Dynamic Contact Angle (Angle of Advance) Evaluation (3)]

The test solution of each Test Example shown in Tables 2-8 to 2-13 was prepared by a conventional method. The unit of each component in Tables 2-8 to 2-13 is w/v % The container material was a container material containing a cyclic olefin copolymer (COC; TOPAS8007 (manufactured by Polyplastics Co., Ltd.)).

The dynamic contact angle of each test solution was determined (average of 3 measurement values) in accordance with the procedure shown in the testing method described above. Subsequently, the change rate of the dynamic contact angle of Test Example with respect to the corresponding test solution was calculated according to [Expression 3] given below. The calculated results are shown in Tables 2-8 to 2-13.

Change rate of the dynamic contact angle (%)=
{(dynamic contact angle of the test solution of Test Example/dynamic contact angle of the corresponding test solution)−1}×100  [Expression 3]

Note that the corresponding test solution is Test Example 3-1 as to Test Examples 3-2 to 3-11, Test Example 3-12 as to Test Examples 3-13 to 3-17, Test Example 3-18 as to Test Examples 3-19 to 3-22, Test Example 3-23 as to Test Examples 3-24 to 3-29, Test Example 3-30 as to Test Examples 3-31 to 3-35, Test Example 3-36 as to Test Examples 3-37 to 3-39, Test Example 3-40 as to Test Examples 3-41 to 3-43, Test Example 3-44 as to Test Examples 3-45 to 3-47, Test Example 3-48 as to Test Examples 3-49 to 3-55, Test Example 3-56 as to Test Examples 3-57 to 3-63, and Test Example 3-64 as to Test Examples 3-65 and 3-66.

TABLE 2-8

|  | Test Example 3-1 | Test Example 3-2 | Test Example 3-3 | Test Example 3-4 | Test Example 3-5 | Test Example 3-6 | Test Example 3-7 | Test Example 3-8 | Test Example 3-9 | Test Example 3-10 | Test Example 3-11 |
|---|---|---|---|---|---|---|---|---|---|---|---|
| (A2) Polysorbate 80 | 0.3 | 0.3 | 0.3 | 0.3 | 0.3 | 0.3 | 0.3 | 0.3 | 0.3 | 0.3 | 0.3 |
| (A2) Polyoxyethylene hydrogenated castor oil 60 | — | 0.3 | — | — | — | — | — | — | — | — | 0.4 |
| (A2) Polyoxyethylene castor oil 10 | — | — | 0.01 | — | — | — | — | — | — | — | — |
| (A2) Polyoxyl 40 stearate | — | — | — | 0.05 | — | — | — | — | — | — | — |
| (A2) POE(200)POP(20) glycol | — | — | — | — | 0.5 | — | — | — | — | — | — |
| (A2) POE(196)POP(67) glycol | — | — | — | — | — | 0.01 | — | — | — | — | 0.05 |
| (A2) Propylene glycol | — | — | — | — | — | — | 0.1 | — | — | — | — |
| (A2) Polyethylene glycol 4000 | — | — | — | — | — | — | — | 0.5 | — | — | — |
| (A2) Glycerin | — | — | — | — | — | — | — | — | 0.01 | — | — |
| (A2) D-Mannitol | — | — | — | — | — | — | — | — | — | 0.5 | — |
| (B2) Boric acid | 1.8 | 1.8 | 1.8 | 1.8 | 1.8 | 1.8 | 1.8 | 1.8 | 1.8 | 1.8 | 1.8 |
| (B2) Borax | 0.2 | 0.2 | 0.2 | 0.2 | 0.2 | 0.2 | 0.2 | 0.2 | 0.2 | 0.2 | 0.2 |

TABLE 2-8-continued

|  | Test Example 3-1 | Test Example 3-2 | Test Example 3-3 | Test Example 3-4 | Test Example 3-5 | Test Example 3-6 | Test Example 3-7 | Test Example 3-8 | Test Example 3-9 | Test Example 3-10 | Test Example 3-11 |
|---|---|---|---|---|---|---|---|---|---|---|---|
| Hydrochloric acid | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance |
| pH | 6 | 6 | 6 | 6 | 6 | 6 | 6 | 6 | 6 | 6 | 6 |
| Change rate of dynamic contact angle | — | 8.4% | 6.4% | 7.6% | 3.1% | 7.5% | 8.2% | 3.3% | 6.2% | 6.6% | 10.5% |

TABLE 2-9

|  | Test Example 3-12 | Test Example 3-13 | Test Example 3-14 | Test Example 3-15 | Test Example 3-16 | Test Example 3-17 | Test Example 3-18 | Test Example 3-19 | Test Example 3-20 | Test Example 3-21 | Test Example 3-22 |
|---|---|---|---|---|---|---|---|---|---|---|---|
| (A2) Polysorbate 80 | 0.02 | 0.02 | 0.02 | 0.02 | 0.02 | 0.02 | 0.5 | 0.5 | 0.5 | 0.5 | 0.5 |
| (A2) Polyoxyethylene hydrogenated castor oil 60 | — | 0.05 | — | — | — | — | — | 0.01 | — | — | — |
| (A2) Polyoxyethylene castor oil 10 | — | — | 0.005 | — | — | — | — | — | 0.03 | — | — |
| (A2) Polyoxyl 40 stearate | — | — | — | 0.01 | — | — | — | — | — | 0.8 | — |
| (A2) POE(200)POP(20) glycol | — | — | — | — | 2 | — | — | — | — | — | 0.1 |
| (A2) POE(196)POP(67) glycol | — | — | — | — | — | 0.1 | — | — | — | — | — |
| (B2) Epsilon aminocaproic acid | 1 | 1 | 1 | 1 | 1 | 1 | — | — | — | — | — |
| (B2) Trometamol | — | — | — | — | — | — | 0.5 | 0.5 | 0.5 | 0.5 | 0.5 |
| Hydrochloric acid | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance |
| pH | 5 | 5 | 5 | 5 | 5 | 5 | 8 | 8 | 8 | 8 | 8 |
| Change rate of dynamic contact angle | — | 9.8% | 8.2% | 9.0% | 9.1% | 6.5% | — | 4.1% | 5.1% | 4.3% | 3.2% |

TABLE 2-10

|  | Test Example 3-23 | Test Example 3-24 | Test Example 3-25 | Test Example 3-26 | Test Example 3-27 | Test Example 3-28 | Test Example 3-29 | Test Example 3-30 | Test Example 3-31 | Test Example 3-32 | Test Example 3-33 | Test Example 3-34 | Test Example 3-35 |
|---|---|---|---|---|---|---|---|---|---|---|---|---|---|
| (A2) Polyoxyethylene hydrogenated castor oil 60 | 1 | 1 | 1 | 1 | 1 | 1 | 1 | 0.15 | 0.15 | 0.15 | 0.15 | 0.15 | 0.15 |
| (A2) Polyoxyl 40 stearate | — | 0.02 | — | — | — | — | — | — | — | — | — | — | — |
| (A2) POE(200)POP(20) glycol | — | — | 1 | — | — | — | — | — | — | 1.5 | — | — | — |
| (A2) POE(196)POP(67) glycol | — | — | — | 0.05 | — | — | — | — | — | — | 0.07 | — | — |
| (A2) Propylene glycol | — | — | — | — | 1.5 | — | — | — | — | — | — | 0.2 | — |
| (A2) Polyethylene glycol 400 | — | — | — | — | — | 0.2 | — | — | — | — | — | 0.2 | — |
| (A2) Glycerin | — | — | — | — | — | — | 0.15 | — | — | — | — | — | 0.03 |
| (B2) Epsilon aminocaproic acid | 3 | 3 | 3 | 3 | 3 | 3 | 3 | — | — | — | — | — | — |
| (B2) Trometamol | — | — | — | — | — | — | — | 0.8 | 0.8 | 0.8 | 0.8 | 0.8 | 0.8 |
| Hydrochloric acid | q.s. | q.s. | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance | Balance | Balance |
| pH | 5 | 5 | 5 | 5 | 5 | 5 | 5 | 8 | 8 | 8 | 8 | 8 | 8 |
| Change rate of dynamic contact angle | — | 9.0% | 10.9% | 10.6% | 9.6% | 9.4% | 9.9% | — | 10.4% | 3.5% | 4.5% | 3.3% | 3.2% |

TABLE 2-11

|  | Test Example 3-36 | Test Example 3-37 | Test Example 3-38 | Test Example 3-39 | Test Example 3-40 | Test Example 3-41 | Test Example 3-42 | Test Example 3-43 | Test Example 3-44 | Test Example 3-45 | Test Example 3-46 | Test Example 3-47 |
|---|---|---|---|---|---|---|---|---|---|---|---|---|
| (A2) POE(200)POP(20) glycol | 0.5 | 0.5 | 0.5 | 0.5 | 0.05 | 0.05 | 0.05 | 0.05 | 3 | 3 | 3 | 3 |
| (A2) Propylene glycol | — | 0.2 | — | — | — | 0.8 | — | — | — | 2 | — | — |
| (A2) Polyethylene glycol 4000 | — | — | 0.5 | — | — | — | 2 | — | — | — | 0.1 | — |
| (A2) Glycerin | — | — | — | 0.15 | — | — | — | 0.4 | — | — | — | 0.3 |
| (B2) Boric acid | 0.6 | 0.6 | 0.6 | 0.6 | — | — | — | — | — | — | — | — |
| (B2) Borax | 0.1 | 0.1 | 0.1 | 0.1 | — | — | — | — | — | — | — | — |
| (B2) Epsilon aminocaproic acid | — | — | — | — | 1 | 1 | 1 | 1 | — | — | — | — |
| (B2) Trometamol | — | — | — | — | — | — | — | — | 1.2 | 1.2 | 1.2 | 1.2 |
| Hydrochloric acid | q.s. | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance | Balance |
| pH | 6 | 6 | 6 | 6 | 5 | 5 | 5 | 5 | 8 | 8 | 8 | 8 |
| Change rate of dynamic contact angle | — | 3.1% | 3.2% | 6.6% | — | 9.2% | 8.1% | 6.4% | — | 9.0% | 9.0% | 8.1% |

TABLE 2-12

|  | Test Example 3-48 | Test Example 3-49 | Test Example 3-50 | Test Example 3-51 | Test Example 3-52 | Test Example 3-53 | Test Example 3-54 | Test Example 3-55 |
|---|---|---|---|---|---|---|---|---|
| (A2) Polyoxyethylene hydrogenated castor oil 60 | 0.35 | 0.35 | 0.35 | 0.35 | 0.35 | 0.35 | 0.35 | 0.35 |
| (A2) Polyoxyethylene castor oil 10 | — | 0.02 | — | — | — | — | — | — |
| (A2) Polyoxyl 40 stearate | — | — | 0.15 | — | — | — | — | — |
| (A2) POE(196)POP(67) glycol | — | — | — | 0.05 | — | — | — | — |
| (A2) Propylene glycol | — | — | — | — | 0.2 | — | — | — |
| (A2) Polyethylene glycol 4000 | — | — | — | — | — | 0.035 | — | — |
| (A2) Glycerin | — | — | — | — | — | — | 0.08 | — |
| (A2) D-Mannitol | — | — | — | — | — | — | — | 0.8 |
| (B2) Boric acid | 1 | 1 | 1 | 1 | 1 | 1 | 1 | 1 |
| (B2) Borax | 0.07 | 0.07 | 0.07 | 0.07 | 0.07 | 0.07 | 0.07 | 0.07 |
| Hydrochloric acid | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. |
| Purified water | Balance | Balance | Balance | Balance | Balance | Balance | Balance | Balance |
| pH | 5 | 5 | 5 | 5 | 5 | 5 | 5 | 5 |
| Change rate of dynamic contact angle | — | 6.4% | 8.2% | 7.5% | 10.6% | 6.5% | 7.3% | 9.5% |

TABLE 2-13

|  | Test Example 3-56 | Test Example 3-57 | Test Example 3-58 | Test Example 3-59 | Test Example 3-60 | Test Example 3-61 | Test Example 3-62 | Test Example 3-63 | Test Example 3-64 | Test Example 3-65 | Test Example 3-66 |
|---|---|---|---|---|---|---|---|---|---|---|---|
| (A2) Polyoxyl 40 stearate | 0.2 | 0.2 | 0.2 | 0.2 | 0.2 | 0.2 | 0.2 | 0.2 | — | — | — |
| (A2) POE(196)POP(67) glycol | — | 0.1 | — | — | — | 0.1 | — | 0.1 | 0.08 | 0.08 | 0.08 |
| (A2) Propylene glycol | — | — | 0.4 | — | — | 0.3 | 0.4 | — | — | 0.08 | — |
| (A2) Sorbitol | — | — | — | 0.1 | — | — | — | — | — | — | 0.05 |
| (A2) Polyoxyethylene castor oil 10 | — | — | — | — | 0.01 | — | 0.3 | 0.005 | — | — | — |
| (B2) Boric acid | 1.5 | 1.5 | 1.5 | 1.5 | 1.5 | 1.5 | 1.5 | 1.5 | 1.5 | 1.5 | 1.5 |
| (B2) Borax | 0.15 | 0.15 | 0.15 | 0.15 | 0.15 | 0.15 | 0.15 | 0.15 | 0.15 | 0.15 | 0.15 |
| Hydrochloric acid | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance |
| pH | 6.8 | 6.8 | 6.8 | 6.8 | 6.8 | 6.8 | 6.8 | 6.8 | 6.8 | 6.8 | 6.8 |
| Change rate of dynamic contact angle | — | 7.1% | 7.3% | 8.2% | 7.0% | 12.0% | 15.6% | 10.3% | — | 6.9% | 6.0% |

As shown in Tables 2-8 to 2-13, the test solution containing two or more kinds of components (A2), and the component (B2) has a larger dynamic contact angle than that of the test solution containing one kind of component (A2) and the component (B2) and can further suppress wetting to the container.

[Test Example 4: Sensory Evaluation (1)]

The test solution of each Test Example shown in Table 2-14 was prepared by a conventional method and filled in 1 mL each in 5 mL glass ampules. The unit of each component in Table 2-14 is w/v %. Note that the corresponding prescribed solution is a prescription in which components other than the component (A2) were excluded from the prescription of each test solution, and the pH was adjusted with appropriate amounts of hydrochloric acid and sodium hydroxide (the balance was purified water). Further, container material strips of 2 mm in width, 20 mm in length, and 0.2 mm in thickness were dipped therein one by one and immediately sealed hermetically. The container material was a cyclic olefin copolymer (COC; TOPAS8007 (manufactured by Polyplastics Co., Ltd.)). Then, heat treatment of still standing at 60° C. was performed in a thermostat. The period of the heat treatment was as shown in Table 2-14. Thereafter, 20 μL of each test solution before and after the heat treatment was dropped onto the arms of four subjects sensitive to smell, spread in a circle of approximately 2 cm in diameter with their fingers, and evaluated by the VAS (visual analog scale) method after sniffing. Specifically, as to "odor", the subjects pointed at one point on a straight line corresponding to the smell of each test solution when "not felt" was defined as 0 mm and "very felt" was defined as 100 mm on both ends of the 10 cm straight line. The distance (mm) from the point of 0 mm was measured, and the average from the four subjects was calculated and regarded as the VAS value of the test solution. Subsequently, the value of change in VAS between before and after the heat treatment was calculated according to [Expression 4-1] given below. Thereafter, the improvement rate of smell of the test solution of Test Example with respect to the corresponding prescribed solution was calculated according to [Expression 4-2] given below. The calculated results are shown in Table 2-14.

Value of change in VAS=VAS value of the test solution before the heat treatment−VAS value of the test solution after the heat treatment [Expression 4-1]

Improvement rate of smell (%)={1−(value of change in VAS of each Test Example/value of change in VAS of the corresponding prescribed solution)}×100 [Expression 4-2]

As shown in Table 2-14, it was revealed that Test Example in which the COC-containing resin container material was dipped in the test solution containing the component (A2) and the component (B2) has a problem that the smell was deteriorated, as compared with Test Example in which the COC-containing resin container material was dipped in the test solution containing the component (A2).

[Test Example 5: Sensory Evaluation (2)]

The test solution of each Test Example shown in Tables 2-15 to 2-17 was prepared by a conventional method and filled in 1 mL each in 5 mL glass ampules. The unit of each component in Tables 2-15 to 2-17 is w/v %. Container material strips of 2 mm in width, 20 mm in length, and 0.2 mm in thickness were dipped one by one in each test solution and immediately sealed hermetically. The container material was a cyclic olefin copolymer (COC; TOPAS 8007 (manufactured by Polyplastics Co., Ltd.)). Then, heat treatment of still standing at 60° C. was performed in a thermostat. The period of the heat treatment was as shown in Tables 2-15 to 2-17. Thereafter, 20 μL of each test solution after the heat treatment was dropped onto the arms of four subjects sensitive to smell, spread in a circle of approximately 2 cm in diameter with their fingers, and evaluated by the VAS (visual analog scale) method after sniffing. Specifically, as to "odor", the subjects pointed at one point on a straight line corresponding to the smell of each test solution when "not felt" was defined as 0 mm and "very felt" was defined as 100 mm on both ends of the 10 cm straight line. The distance (mm) from the point of 0 mm was measured, and the average from the four subjects was calculated and regarded as the VAS value of the test solution. Subsequently, the improvement rate of smell of the test solution of Test Example with respect to the corresponding Test Example was calculated according to [Expression 5] given below. The calculated results are shown in Tables 2-15 to 2-17.

Improvement rate of smell (%)={1−(VAS value of Test Example after the heat treatment/VAS value of the corresponding test solution after the heat treatment)}×100 [Expression 5]

Note that the corresponding test solution is test solution 4-1 as to Test Examples 5-1 to 5-6, test solution 4-2 as to Test Examples 5-7 to 5-11, test solution 4-3 as to Test Examples 5-12 to 5-19, test solution 4-4 as to Test Examples 5-20 to 5-26, and test solution 4-5 as to Test Examples 5-27 to 5-32.

TABLE 2-14

|  | Test Example 4-1 | Test Example 4-2 | Test Example 4-3 | Test Example 4-4 | Test Example 4-5 |
|---|---|---|---|---|---|
| (A2) Polysorbate 80 | 0.8 | 0.8 | — | — | — |
| (A2) Polyoxyethylene hydrogenated castor oil 60 | — | — | 0.5 | 0.2 | 0.2 |
| (B2) Sodium hydrogen phosphate | 0.3 | 0.3 | — | — | — |
| (B2) Sodium dihydrogen phosphate | 0.2 | 0.2 | — | — | — |
| (B2) Citric acid | — | — | 0.01 | — | — |
| (B2) Sodium citrate | — | — | 0.4 | — | — |
| (B2) Boric acid | — | — | — | 0.4 | 0.4 |
| (B2) Borax | — | — | — | 0.15 | 0.15 |
| Hydrochloric acid | q.s. | q.s. | q.s. | q.s. | q.s. |
| Sodium hydroxide | q.s. | q.s. | q.s. | q.s. | q.s. |
| Purified water | Balance | Balance | Balance | Balance | Balance |
| pH | 7.0 | 7.0 | 6.0 | 7.2 | 7.2 |
| Heat treatment period | 2 days | 5 days | 2 days | 3 days | 4 days |
| Improvement rate of smell (%) | −201% | −96% | −114% | −129% | −27% |

TABLE 2-15

|  | Test Example 5-1 | Test Example 5-2 | Test Example 5-3 | Test Example 5-4 | Test Example 5-5 | Test Example 5-6 | Test Example 5-7 | Test Example 5-8 | Test Example 5-9 | Test Example 5-10 | Test Example 5-11 |
|---|---|---|---|---|---|---|---|---|---|---|---|
| (A2) Polysorbate 80 | 0.8 | 0.8 | 0.8 | 0.8 | 0.8 | 0.8 | 0.8 | 0.8 | 0.8 | 0.8 | 0.8 |
| (A2) Polyoxyethylene hydrogenated castor oil 60 | 0.1 | — | — | — | — | — | 0.1 | — | — | — | — |
| (A2) Polyoxyethylene castor oil 10 | — | 0.008 | — | — | — | — | — | — | — | — | — |
| (A2) Polyoxyl 40 stearate | — | — | 0.15 | — | — | — | — | — | — | — | — |
| (A2) POE(200)POP(20) glycol | — | — | — | 1 | — | — | — | — | — | — | — |
| (A2) POE(196)POP(67) glycol | — | — | — | — | 0.1 | — | — | — | — | — | — |
| (A2) POE(160)POP(30) glycol | — | — | — | — | — | 0.5 | — | — | — | — | — |
| (A2) Propylene glycol | — | — | — | — | — | — | — | 0.8 | — | — | — |
| (A2) Polyethylene glycol 4000 | — | — | — | — | — | — | — | — | 1 | — | — |
| (A2) Glycerin | — | — | — | — | — | — | — | — | — | 0.6 | — |
| (A2) D-Mannitol | — | — | — | — | — | — | — | — | — | — | 2 |
| (B2) Sodium hydrogen phosphate | 0.3 | 0.3 | 0.3 | 0.3 | 0.3 | 0.3 | 0.3 | 0.3 | 0.3 | 0.3 | 0.3 |
| (B2) Sodium dihydrogen phosphate | 0.2 | 0.2 | 0.2 | 0.2 | 0.2 | 0.2 | 0.2 | 0.2 | 0.2 | 0.2 | 0.2 |
| Hydrochloric acid | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance |
| pH | 7.0 | 7.0 | 7.0 | 7.0 | 7.0 | 7.0 | 7.0 | 7.0 | 7.0 | 7.0 | 7.0 |
| Heat treatment period | 2 days | 2 days | 2 days | 2 days | 2 days | 2 days | 5 days | 5 days | 5 days | 5 days | 5 days |
| Improvement rate of smell (%) | 57% | 54% | 55% | 29% | 43% | 52% | 58% | 36% | 24% | 38% | 24% |

TABLE 2-16

|  | Test Example 5-12 | Test Example 5-13 | Test Example 5-14 | Test Example 5-15 | Test Example 5-16 | Test Example 5-17 | Test Example 5-18 | Test Example 5-19 |
|---|---|---|---|---|---|---|---|---|
| (A2) Polyoxyethylene hydrogenated castor oil 60 | 0.5 | 0.5 | 0.5 | 0.5 | 0.5 | 0.5 | 0.5 | 0.5 |
| (A2) Polyoxyethylene castor oil 10 | 0.001 | — | — | — | — | — | — | — |
| (A2) Polyoxyl 40 stearate | — | 1 | — | — | — | — | — | — |
| (A2) POE(196)POP(67) glycol | — | — | 0.5 | — | — | — | — | — |
| (A2) Propylene glycol | — | — | — | 0.2 | — | — | — | — |
| (A2) Polyethylene glycol 4000 | — | — | — | — | 0.6 | — | — | — |
| (A2) Glycerin | — | — | — | — | — | 0.7 | — | — |
| (A2) D-Mannitol | — | — | — | — | — | — | 0.8 | — |
| (A2) Polysorbate 80 | — | — | — | — | — | — | — | 1 |
| (B2) Citric acid | 0.01 | 0.01 | 0.01 | 0.01 | 0.01 | 0.01 | 0.01 | 0.01 |
| (B2) Sodium citrate | 0.4 | 0.4 | 0.4 | 0.4 | 0.4 | 0.4 | 0.4 | 0.4 |
| Hydrochloric acid | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. |
| Purified water | Balance | Balance | Balance | Balance | Balance | Balance | Balance | Balance |
| pH | 6.0 | 6.0 | 6.0 | 6.0 | 6.0 | 6.0 | 6.0 | 6.0 |
| Heat treatment period | 2 days | 2 days | 2 days | 2 days | 2 days | 2 days | 2 days | 2 days |
| Improvement rate of smell (%) | 45% | 53% | 52% | 23% | 26% | 65% | 45% | 70% |

TABLE 2-17

|  | Test Example 5-20 | Test Example 5-21 | Test Example 5-22 | Test Example 5-23 | Test Example 5-24 | Test Example 5-25 | Test Example 5-26 | Test Example 5-27 | Test Example 5-28 | Test Example 5-29 | Test Example 5-30 | Test Example 5-31 | Test Example 5-32 |
|---|---|---|---|---|---|---|---|---|---|---|---|---|---|
| (A2) Polyoxyethylene hydrogenated castor oil 60 | 0.2 | 0.2 | 0.2 | 0.2 | 0.2 | 0.2 | 0.2 | 0.2 | 0.2 | 0.2 | 0.2 | 0.2 | 0.2 |
| (A2) Polyoxyethylene castor oil 10 | 0.04 | — | — | — | — | — | — | — | — | — | — | — | — |
| (A2) Polyoxyl 40 stearate | — | 0.5 | — | — | — | — | — | — | — | — | — | — | — |

TABLE 2-17-continued

|  | Test Example 5-20 | Test Example 5-21 | Test Example 5-22 | Test Example 5-23 | Test Example 5-24 | Test Example 5-25 | Test Example 5-26 | Test Example 5-27 | Test Example 5-28 | Test Example 5-29 | Test Example 5-30 | Test Example 5-31 | Test Example 5-32 |
|---|---|---|---|---|---|---|---|---|---|---|---|---|---|
| (A2) POE(160)POP(30) glycol | — | — | 0.8 | — | — | — | — | — | — | — | — | — | — |
| (A2) Polyethylene glycol 4000 | — | — | — | 2 | — | — | — | — | — | — | — | — | — |
| (A2) Glycerin | — | — | — | — | 1 | — | — | — | — | — | — | — | — |
| (A2) D-Mannitol | — | — | — | — | — | 1.2 | — | — | — | — | — | — | — |
| (A2) Polysorbate 80 | — | — | — | — | — | — | 0.8 | — | — | — | — | — | — |
| (A2) Polyoxyethylene castor oil 35 | — | — | — | — | — | — | — | 0.2 | — | — | — | — | — |
| (A2) POE(200)POP(20) | — | — | — | — | — | — | — | — | 2 | — | — | — | — |
| (A2) POE(196)POP(67) | — | — | — | — | — | — | — | — | — | 0.05 | — | — | — |
| (A2) Propylene glycol | — | — | — | — | — | — | — | — | — | — | 0.5 | — | — |
| (A2) D-Sorbitol | — | — | — | — | — | — | — | — | — | — | — | 0.5 | — |
| (A2) Xylitol | — | — | — | — | — | — | — | — | — | — | — | — | 0.05 |
| (B2) Boric acid | 0.4 | 0.4 | 0.4 | 0.4 | 0.4 | 0.4 | 0.4 | 0.4 | 0.4 | 0.4 | 0.4 | 0.4 | 0.4 |
| (B2) Borax | 0.15 | 0.15 | 0.15 | 0.15 | 0.15 | 0.15 | 0.15 | 0.15 | 0.15 | 0.15 | 0.15 | 0.15 | 0.15 |
| Hydrochloric acid | q.s. | q.s. | q.s. | q.s. | q.s. | q.s. | q.s. | q.s. | q.s. | q.s. | q.s. | q.s. | q.s. |
| Sodium hydroxide | q.s. | q.s. | q.s. | q.s. | q.s. | q.s. | q.s. | q.s. | q.s. | q.s. | q.s. | q.s. | q.s. |
| Purified water | Balance | Balance | Balance | Balance | Balance | Balance | Balance | Balance | Balance | Balance | Balance | Balance | Balance |
| pH | 7.2 | 7.2 | 7.2 | 7.2 | 7.2 | 7.2 | 7.2 | 7.2 | 7.2 | 7.2 | 7.2 | 7.2 | 7.2 |
| Heat treatment period | 3 days | 3 days | 3 days | 3 days | 3 days | 3 days | 3 days | 4 days | 4 days | 4 days | 4 days | 4 days | 4 days |
| Improvement rate of smell (%) | 24% | 38% | 29% | 53% | 94% | 53% | 35% | 65% | 65% | 65% | 45% | 65% | 65% |

As shown in Tables 2-15 to 2-17, the test solution containing two kinds of components (A2) and the component (B2) improved the improvement rate of smell as compared with the test solution containing one kind of component (A2) and the component (B2).

[Test Example 6: Dynamic Contact Angle (Angle of Advance) Evaluation (4)]

The test solution of each Test Example shown in Table 2-19 was prepared by a conventional method. The unit of each component in Table 2-19 is w/v %. A resin containing a cyclic olefin copolymer (COC; TOPAS8007 (manufactured by Polyplastics Co., Ltd.)) (container material A), and resins containing COC and low-density polyethylene (LDPE) or linear low-density polyethylene (LLDPE) (container materials B, C, D and E) shown in Table 2-18 were used as container materials. The unit of each constituent contained in the container materials in Table 2-18 is w/w %.

TABLE 2-18

|  | COC | LDPE | LLDPE |
|---|---|---|---|
| Container material A | 100 | — | — |
| Container material B | 70 | 30 | — |
| Container material C | 90 | — | 10 |
| Container material D | 70 | — | 30 |
| Container material E | 55 | — | 45 |

The dynamic contact angle of each test solution was determined (average of 3 measurement values) in accordance with the procedure shown in the testing method described above. Subsequently, the change rate of the dynamic contact angle of the test solution of Test Example with respect to the corresponding prescribed solution was calculated according to [Expression 6] given below. The calculated results are shown in Table 2-19.

Change rate of the dynamic contact angle (%)=
{(dynamic contact angle of the test solution of Test Example/dynamic contact angle of the corresponding prescribed solution contacted with the container material A)−1}×100  [Expression 6]

Note that the corresponding test solution is Test Example 3-1 as to Test Examples 6-1 and 6-2, Test Example 3-48 as to Test Example 6-3, and Test Example 3-56 as to Test Examples 6-4 and 6-5. The container material A was used in determining the dynamic contact angle of the corresponding prescribed solution.

TABLE 2-19

|  | Test Example 6-1 | Test Example 6-2 | Test Example 6-3 | Test Example 6-4 | Test Example 6-5 |
|---|---|---|---|---|---|
| (A2) Polysorbate 80 | 0.3 | 0.3 | — | — | — |
| (A2) Polyoxyethylene hydrogenated castor oil 60 | 0.3 | — | 0.35 | — | — |
| (A2) POE(196)POP(67) glycol | — | 0.01 | 0.05 | — | — |
| (A2) Polyoxyl 40 stearate | — | — | — | 0.2 | 0.2 |
| (A2) Propylene glycol | — | — | — | 0.4 | — |
| (A2) Polyoxyethylene castor oil 10 | — | — | — | — | 0.01 |
| (B2) Boric acid | 1.8 | 1.8 | 1 | 1.5 | 1.5 |
| (B2) Borax | 0.2 | 0.2 | 0.07 | 0.15 | 0.15 |
| Hydrochloric acid | q.s. | q.s. | q.s. | q.s. | q.s. |
| Sodium hydroxide | q.s. | q.s. | q.s. | q.s. | q.s. |

TABLE 2-19-continued

|  |  | Test Example 6-1 | Test Example 6-2 | Test Example 6-3 | Test Example 6-4 | Test Example 6-5 |
|---|---|---|---|---|---|---|
|  | Purified water | Balance | Balance | Balance | Balance | Balance |
|  | pH | 6 | 6 | 5 | 6.8 | 6.8 |
| Change rate of dynamic contact angle (%) | Container material B | 12.5% | 11.3% | 9.7% | 9.8% | 9.1% |
|  | Container material D | 14.7% | 13.9% | 10.3% | 12.2% | 13.3% |
|  | Container material E | 16.9% | 15.7% | 12.7% | — | — |

When a resin containing COC and LDPE or COC and LLDPE is used as a container material, the test solution containing two or more kinds of components (A2) and the component (B2) has a larger dynamic contact angle than that of the test solution containing one kind of component (A2) and the component (B2) and can further suppress wetting to the container. The dynamic contact angle was much larger, particularly, for the resin containing COC and LLDPE.

[Test Example 7: Dynamic Contact Angle (Angle of Advance) Evaluation (5)]

The test solution of each Test Example shown in Table 2-20 was prepared by a conventional method. The unit of each component in Table 2-20 is w/v %. The container material employed the container material shown in Table 2-18 of Test Example 6.

The dynamic contact angle of each test solution was determined (average of 3 measurement values) in accordance with the procedure shown in the testing method described above. Subsequently, the change rate of the dynamic contact angle of the test solution of Test Example with respect to the corresponding prescribed solution was calculated according to [Expression 7] given below. The calculated results are shown in Table 2-20.

Change rate of the dynamic contact angle (%)=
{(dynamic contact angle of the test solution of Test Example/dynamic contact angle of the corresponding prescribed solution contacted with the container material C)−1}×100    [Expression 7]

Note that the corresponding prescribed solution is a prescription in which the component (B2) were excluded from the prescription of each test solution, and the pH was adjusted with appropriate amounts of hydrochloric acid and sodium hydroxide (the balance was purified water). The container material C was used in determining the dynamic contact angle of the corresponding prescribed solution.

TABLE 2-20

|  | Test Example 7-1 | Test Example 7-2 | Test Example 7-3 | Test Example 7-4 | Test Example 7-5 | Test Example 7-6 | Test Example 7-7 |
|---|---|---|---|---|---|---|---|
| (A2) Polysorbate 80 | 0.08 | — | — | — | — | — | — |
| (A2) Polyoxyethylene hydrogenated castor oil 60 | — | 0.08 | 0.08 | — | — | — | — |
| (A2) Polyoxyethylene castor oil 10 | — | — | 0.016 | — | — | — | — |
| (A2) Propylene glycol | — | — | — | 0.1 | — | — | — |
| (A2) Polyethylene glycol 4000 | — | — | — | — | 0.1 | — | — |
| (A2) Glycerin | — | — | — | — | — | 0.1 | — |
| (A2) D-Sorbitol | — | — | — | — | — | — | 0.1 |
| (B2) Boric acid | — | — | 1.5 | — | 1.8 | 0.5 | 0.8 |
| (B2) Borax | — | — | 0.35 | — | 0.4 | 0.008 | 0.12 |
| (B2) Trometamol | 0.2 | — | — | 1.5 | — | — | — |
| (B2) Epsilon aminocaproic acid | — | 1.5 | — | — | — | — | — |
| Hydrochloric acid | q.s. | q.s. | q.s. | q.s. | q.s. | q.s. | q.s. |
| Sodium hydroxide | q.s. | q.s. | q.s. | q.s. | q.s. | q.s. | q.s. |
| Purified water | Balance | Balance | Balance | Balance | Balance | Balance | Balance |
| pH | 7.5 | 7.5 | 5.2 | 8.0 | 8.0 | 5.0 | 7.2 |
| Change rate of dynamic contact angle (%) Container material C | 11.0% | 12.5% | 19.4% | 12.4% | 12.0% | 14.7% | 11.8% |

When a resin containing COC and LLDPE is used as a container material, the dynamic contact angle of the test solution containing the component (A2) and the component (B2) is larger than the dynamic contact angle of the test solution containing no component (B2), and wetting to the container can be suppressed.

[Test Example 8: Dynamic Contact Angle (Angle of Advance) Evaluation (6)]

The test solution of each Test Example shown in Table 2-21 was prepared by a conventional method. The unit of each component in Table 2-21 is w/v %. The container material employed the container material shown in Table 2-18 of Test Example 6.

The dynamic contact angle of each test solution was determined (average of 3 measurement values) in accordance with the procedure shown in the testing method described above. Subsequently, the change rate of the dynamic contact angle of the test solution of Test Example with respect to the corresponding prescribed solution was calculated according to [Expression 8] given below. The calculated results are shown in Table 2-21.

Change rate of the dynamic contact angle (%)=
{(dynamic contact angle of the test solution of
Test Example/dynamic contact angle of the corresponding prescribed solution contacted with
the container material A)−1}×100    [Expression 8]

Note that the corresponding prescribed solution is a prescription in which only the component (A2) and the component (B2) were contained in the prescription of each test solution, and the pH was adjusted with appropriate amounts of hydrochloric acid and sodium hydroxide (the balance was purified water). The container material A was used in determining the dynamic contact angle of the corresponding prescribed solution.

TABLE 2-21

|  |  | Test Example 8-1 | Test Example 8-2 | Test Example 8-3 | Test Example 8-4 | Test Example 8-5 | Test Example 8-6 | Test Example 8-7 | Test Example 8-8 |
|---|---|---|---|---|---|---|---|---|---|
| (A2) Polysorbate 80 | | 0.08 | 0.08 | 0.08 | 0.08 | 0.25 | 0.25 | — | — |
| (A2) Polyoxyethylene hydrogenated castor oil 60 | | — | — | — | — | — | — | 0.08 | 0.08 |
| (B2) Boric acid | | 1 | 1 | — | — | 1.5 | 1.5 | 1.3 | 1.3 |
| (B2) Borax | | 0.2 | 0.2 | — | — | 0.08 | 0.08 | 0.2 | 0.2 |
| (B2) Sodium hydrogen phosphate | | — | — | 1.2 | 1.2 | — | — | — | — |
| (B2) Sodium dihydrogen phosphate | | — | — | 0.1 | 0.1 | — | — | — | — |
| Hydroxypropylmethylcellulose | | 0.5 | — | — | — | — | — | — | — |
| Polyvinylpyrrolidone K30 | | — | — | 0.8 | — | — | — | — | — |
| Sesame oil | | — | — | — | 0.005 | — | — | — | — |
| White Vaseline | | — | — | — | — | 0.006 | — | — | — |
| Tranilast | | — | 0.5 | — | — | — | — | — | — |
| Pranoprofen | | — | — | — | — | — | — | 0.05 | — |
| Zinc sulfate | | — | — | — | — | — | 0.25 | — | — |
| Chlorpheniramine maleate | | — | — | — | — | — | — | — | 0.03 |
| Hydrochloric acid | | q.s. | q.s. | q.s. | q.s. | q.s. | q.s. | q.s. | q.s. |
| Sodium hydroxide | | q.s. | q.s. | q.s. | q.s. | q.s. | q.s. | q.s. | q.s. |
| Purified water | | Balance | Balance | Balance | Balance | Balance | Balance | Balance | Balance |
| pH | | 7.5 | 7.5 | 7.5 | 7.5 | 5.0 | 5.0 | 6.5 | 6.5 |
| Change rate of dynamic contact angle (%) | Container material A | 11.8% | 7.6% | 7.0% | 8.4% | 7.9% | 7.3% | 12.4% | 7.0% |
| | Container material B | 13.3% | 9.5% | 8.5% | 9.5% | 10.5% | 8.7% | 14.9% | 10.4% |
| | Container material D | 15.6% | 11.9% | 10.4% | 10.9% | 12.3% | 11.5% | 16.5% | 13.6% |

Hydroxypropylmethylcellulose: Hydroxypropylmethylcellulose 2906 (trade name: Metolose 65SH-50 (manufactured by Shin-Etsu Chemical Co., Ltd.))

When COC is used as a container material, the dynamic contact angle of the test solution containing an oil, a polysaccharide, a vinyl compound, or a pharmacologically active component in addition to the component (A2) and the component (B2) is larger than the dynamic contact angle of the test solution containing only the component (A2) and the component (B2), and wetting to the container can be further suppressed. When a resin containing COC and LDPE or COC and LLDPE is used as a container material, the dynamic contact angle is larger, and wetting to the container can be yet further suppressed, as compared with the case of using, as a container material, a resin containing only COC. The dynamic contact angle was much larger, particularly, for the resin containing COC and LLDPE.

[Test Example 9: Sensory Evaluation (3)]

The test solution of each Test Example shown in Table 2-22 was prepared by a conventional method and filled in 1 mL each in 5 mL glass ampules. The unit of each component in Table 2-22 is w/v %. Container material strips of 2 mm in width, 20 mm in length, and 0.2 mm in thickness were dipped one by one in each test solution and immediately sealed hermetically. The container material employed the container material shown in Table 2-18 of Test Example 6. Then, heat treatment of still standing at 60° C. was performed in a thermostat. The period of the heat treatment was as shown in Table 2-22. Thereafter, 20 μL of each test solution after the heat treatment was dropped onto the arms of four subjects sensitive to smell, spread in a circle of approximately 2 cm in diameter with their fingers, and evaluated by the VAS (visual analog scale) method after sniffing. Specifically, as to "odor", the subjects pointed at one point on a straight line corresponding to the smell of each test solution when "not felt" was defined as 0 mm and "very felt" was defined as 100 mm on both ends of the 10 cm straight line. The distance (mm) from the point of 0 mm was measured, and the average from the four subjects was calculated and regarded as the VAS value of the test solution. Subsequently, the improvement rate of smell of the test solution of Test Example with respect to the corresponding Test Example was calculated according to [Expression 9] given below. The calculated results are shown in Table 2-22.

Improvement rate of smell (%)={1−(VAS value of
Test Example after the heat treatment/VAS
value of the corresponding test solution after
the heat treatment)}×100    [Expression 9]

Note that the corresponding test solution is Test Example 4-1 as to Test Example 9-1, Test Example 4-3 as to Test Example 9-2, and Test Example 4-4 as to Test Example 9-3. The container material A was used in determining the VAS value of the corresponding test solution.

TABLE 2-22

|  | Test Example 9-1 | Test Example 9-2 | Test Example 9-3 |
|---|---|---|---|
| (A2) Polysorbate 80 | 0.8 | — | — |
| (A2) Polyoxyethylene hydrogenated castor oil 60 | 0.1 | 0.5 | 0.2 |

TABLE 2-22-continued

|  | | Test Example 9-1 | Test Example 9-2 | Test Example 9-3 |
|---|---|---|---|---|
| (A2) Glycerin | | — | 0.7 | — |
| (A2) Polyethylene glycol 4000 | | — | — | 2 |
| (B2) Sodium hydrogen phosphate | | 0.3 | — | — |
| (B2) Sodium dihydrogen phosphate | | 0.2 | — | — |
| (B2) Citric acid | | — | 0.01 | — |
| (B2) Sodium citrate | | — | 0.4 | — |
| (B2) Boric acid | | — | — | 0.4 |
| (B2) Borax | | — | — | 0.15 |
| Hydrochloric acid | | q.s. | q.s. | q.s. |
| Sodium hydroxide | | q.s. | q.s. | q.s. |
| Purified water | | Balance | Balance | Balance |
| pH | | 7.0 | 6.0 | 7.2 |
| Heat treatment period | | 2 days | 2 days | 3 days |
| Improvement rate of smell (%) | Container material B | 66% | 72% | 63% |
| | Container material D | 77% | 81% | 74% |

Test Examples 9-1 to 9-3 using the test solution containing the component (A2) and the component (B2) and, as a container material, a resin containing COC and LDPE or COC and LLDPE all improved the smell. Particularly, when the resin containing COC and LLDPE (container material D of Test Examples 9-1 to 9-3) was used as a container material, the smell was further improved.

From these results, the ophthalmic composition according to the present embodiment produces an effect of suppressing wetting; thus liquid residues are suppressed. This suppresses contamination attributed to mixing of bacteria or foreign substances, etc. and can achieve high sanitary quality required for delicate ocular mucosal tissues. Furthermore, the ophthalmic composition according to the present embodiment produces an effect of suppressing wetting; thus liquid cutting is improved. This can decrease variations in the amount of dropping required for the eyes, which are relatively small sites, or use in contact lenses. Moreover, the ophthalmic composition according to the present embodiment produces an effect of suppressing change in smell; thus, the generation of offensive smell by contact with a container can be suppressed.

The invention claimed is:

1. An ophthalmic composition comprising terpenoid and a salt thereof, wherein the ophthalmic composition is contained in a container in which a portion or the whole of a part coming into contact with the ophthalmic composition is formed from a resin comprising a cyclic olefin copolymer and polyethylene, wherein:
the cyclic olefin copolymer is a copolymer of norbornene and ethylene,
the polyethylene comprises low-density polyethylene and/or linear low-density polyethylene, and
the content of polyethylene is from 10 to 50% by weight based on a total amount of the resin forming the container.

2. The ophthalmic composition according to claim 1, wherein the resin forming the container further contains polyethylene.

3. The ophthalmic composition according to claim 1, further comprising (B) a buffer.

4. The ophthalmic composition according to claim 1, wherein a content of water is 80 w/v % or more and less than 100 w/v % based on the total amount of the ophthalmic composition.

5. The ophthalmic composition according to claim 1, wherein a maximum value of light transmittance in a visible light region of wavelengths from 400 to 700 nm of the container formed from the resin containing the cyclic olefin polymer and/or the cyclic olefin copolymer is 50% or more.

6. The ophthalmic composition according to claim 1, exhibiting suppressed wetting to a resin containing a cyclic olefin.

7. The ophthalmic composition according to claim 1, wherein the terpenoid is menthol.

8. The ophthalmic composition according to claim 1, wherein the total content of the terpenoid is from 0.00005 to 1 w/v % based on the total amount of the ophthalmic composition.

9. The ophthalmic composition according to claim 3, wherein (B) the buffer is selected from the group consisting of boric acid buffers, phosphoric acid buffers, carbonic acid buffers, citric acid buffers, acetic acid buffers, Tris buffers, epsilon aminocaproic acid buffers, and AMPD (2-amino-2-methyl-1,3-propanediol) buffers.

10. The ophthalmic composition according to claim 1, wherein the container is a container with a composition containment part and a bung hole integrally formed.

* * * * *